(12) United States Patent
Wang et al.

(10) Patent No.: US 7,811,562 B2
(45) Date of Patent: Oct. 12, 2010

(54) BIOMARKERS FOR PRE-SELECTION OF PATIENTS FOR ANTI-IGF1R THERAPY

(75) Inventors: Yan Wang, Scotch Plains, NJ (US); Jonathan A. Pachter, Setauket, NY (US); Yaolin Wang, Edison, NJ (US); Ming Liu, Fanwood, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/290,687

(22) Filed: Nov. 30, 2005

(65) Prior Publication Data

US 2006/0140960 A1 Jun. 29, 2006

Related U.S. Application Data

(60) Provisional application No. 60/633,156, filed on Dec. 3, 2004.

(51) Int. Cl.
*A61K 39/395* (2006.01)
(52) U.S. Cl. .................. 424/133.1; 424/155.1
(58) Field of Classification Search .............. 424/133.1, 424/155.1
See application file for complete search history.

(56) References Cited

U.S. PATENT DOCUMENTS

| | | | |
|---|---|---|---|
| 4,543,439 A | 9/1985 | Frackelton, Jr. et al. | |
| 5,198,340 A | 3/1993 | Mukku | |
| 5,262,308 A | 11/1993 | Baserga | |
| 5,942,412 A | 8/1999 | Prager et al. | |
| 5,958,872 A | 9/1999 | O'Connor et al. | |
| 5,977,307 A | 11/1999 | Friden et al. | |
| 6,022,711 A | 2/2000 | Cunningham et al. | |
| 6,084,085 A | 7/2000 | Baserga et al. | |
| 6,294,330 B1 | 9/2001 | Michnick et al. | |
| 6,300,129 B1 | 10/2001 | Lonberg et al. | |
| 6,316,462 B1 | 11/2001 | Bishop et al. | |
| 6,333,031 B1 | 12/2001 | Olsson et al. | |
| 6,346,390 B1 | 2/2002 | Olsson et al. | |
| 6,372,250 B1 | 4/2002 | Pardridge | |
| 6,537,988 B2 | 3/2003 | Lee | |
| 6,645,775 B1 | 11/2003 | Clark et al. | |
| 7,037,498 B2 | 5/2006 | Cohen et al. | |
| 7,217,796 B2 | 5/2007 | Wang et al. | |
| 7,326,567 B2 | 2/2008 | Saha | |
| 2002/0022023 A1 | 2/2002 | Ullrich et al. | |
| 2002/0025313 A1 | 2/2002 | Micklus et al. | |
| 2002/0107187 A1 | 8/2002 | Kingston et al. | |
| 2002/0132275 A1 | 9/2002 | Fidler et al. | |
| 2002/0155095 A1 | 10/2002 | Nagabhushan et al. | |
| 2002/0164333 A1 | 11/2002 | Nemerow et al. | |
| 2002/0169116 A1 | 11/2002 | Kingston et al. | |
| 2002/0187925 A1 | 12/2002 | Kingston et al. | |
| 2002/0197262 A1 | 12/2002 | Hasan et al. | |
| 2003/0021780 A1 | 1/2003 | Smith et al. | |
| 2003/0031658 A1 | 2/2003 | Brodt et al. | |
| 2003/0045676 A1 | 3/2003 | Kingston et al. | |
| 2003/0087342 A1 | 5/2003 | Mermod et al. | |
| 2003/0088061 A1 | 5/2003 | Staunton | |
| 2003/0092631 A1 | 5/2003 | Deshayes et al. | |
| 2003/0138430 A1 | 7/2003 | Stimmel et al. | |
| 2003/0165502 A1 | 9/2003 | Fujita-Yamaguchi | |
| 2003/0195147 A1 | 10/2003 | Pillutla et al. | |
| 2003/0235582 A1 | 12/2003 | Singh et al. | |
| 2003/0236190 A1 | 12/2003 | Pillutla et al. | |
| 2004/0009154 A1 | 1/2004 | Khan et al. | |
| 2004/0009906 A1 | 1/2004 | Kakkis et al. | |
| 2004/0018191 A1* | 1/2004 | Wang et al. .............. | 424/143.1 |
| 2004/0023887 A1 | 2/2004 | Pillutla et al. | |
| 2004/0047835 A1 | 3/2004 | Bianco | |
| 2004/0057950 A1 | 3/2004 | Waksal et al. | |
| 2004/0086503 A1 | 5/2004 | Cohen et al. | |
| 2004/0086511 A1 | 5/2004 | Zack et al. | |
| 2004/0102360 A1 | 5/2004 | Barnett et al. | |
| 2004/0116330 A1 | 6/2004 | Naito et al. | |
| 2004/0142381 A1 | 7/2004 | Hubbard et al. | |
| 2004/0202651 A1* | 10/2004 | Cohen et al. .............. | 424/131.1 |
| 2004/0228859 A1 | 11/2004 | Graus et al. | |
| 2004/0265307 A1 | 12/2004 | Singh et al. | |
| 2005/0008642 A1 | 1/2005 | Graus et al. | |
| 2005/0048050 A1 | 3/2005 | Fujita-Yamaguchi | |
| 2005/0069539 A1 | 3/2005 | Cohen et al. | |
| 2005/0081812 A1 | 4/2005 | Toedter et al. | |
| 2005/0084906 A1 | 4/2005 | Goetsch et al. | |
| 2005/0136063 A1* | 6/2005 | Wang et al. .............. | 424/178.1 |
| 2005/0176099 A1 | 8/2005 | Saha | |

(Continued)

FOREIGN PATENT DOCUMENTS

DE 197 19 001 C2 5/2001

(Continued)

OTHER PUBLICATIONS

Tonini et al. (Curr. Pharm. Design 12:2303-2317 (2006)).*

(Continued)

*Primary Examiner*—Lynn Bristol

(57) ABSTRACT

The present invention provides methods for identifying patients whose cancers are likely to be responsive to IGF1R inhibitory anti-cancer therapy along with methods for treating such patients. Patients identified by a method of the present invention can be treated with any of several known IGF1R inhibitory agents including antibodies, small molecule inhibitors and anti-sense nucleic acids.

16 Claims, 5 Drawing Sheets

U.S. PATENT DOCUMENTS

| | | | |
|---|---|---|---|
| 2005/0186203 A1 | 8/2005 | Singh et al. | |
| 2005/0244408 A1 | 11/2005 | Cohen et al. | |
| 2005/0249728 A1 | 11/2005 | Singh et al. | |
| 2005/0249730 A1 | 11/2005 | Goetsch et al. | |
| 2005/0272637 A1 | 12/2005 | Clinton et al. | |
| 2005/0272755 A1 | 12/2005 | Denis et al. | |
| 2005/0281812 A1 | 12/2005 | Cohen et al. | |
| 2006/0018910 A1 | 1/2006 | Gualberto et al. | |
| 2006/0205810 A1 | 9/2006 | Zong et al. | |
| 2006/0233810 A1* | 10/2006 | Wang et al. | 424/155.1 |
| 2006/0233814 A1 | 10/2006 | Goldmakher et al. | |
| 2006/0286103 A1 | 12/2006 | Kolhe et al. | |
| 2007/0059241 A1* | 3/2007 | Wang et al. | 424/1.49 |
| 2007/0059305 A1* | 3/2007 | Wang et al. | 424/143.1 |
| 2007/0071675 A1 | 3/2007 | Wu et al. | |
| 2008/0014197 A1 | 1/2008 | Wang et al. | |
| 2008/0112888 A1 | 5/2008 | Wang | |

FOREIGN PATENT DOCUMENTS

| | | |
|---|---|---|
| FR | 2 834 900 | 7/2003 |
| FR | 2 834 990 | 7/2003 |
| FR | 2 834 991 | 7/2003 |
| WO | WO 91/04014 | 4/1991 |
| WO | WO 91/14438 | 10/1991 |
| WO | WO 97/44352 | 11/1997 |
| WO | WO98/17801 | 4/1998 |
| WO | WO 98/22092 | 5/1998 |
| WO | WO 98/45427 | 10/1998 |
| WO | WO 99/25378 | 5/1999 |
| WO | WO 99/28347 | 6/1999 |
| WO | WO 99/42127 | 8/1999 |
| WO | WO 99/60023 | 11/1999 |
| WO | WO 00/22130 | 4/2000 |
| WO | WO 00/50067 | 8/2000 |
| WO | WO 00/69454 | 11/2000 |
| WO | WO 01/07084 A1 | 2/2001 |
| WO | WO 01/30964 A2 | 5/2001 |
| WO | WO 01/36632 A3 | 5/2001 |
| WO | WO 01/70268 A1 | 9/2001 |
| WO | WO 01/70930 A2 | 9/2001 |
| WO | WO 01/72771 A2 | 10/2001 |
| WO | WO 01/75064 A2 | 10/2001 |
| WO | WO 02/04522 A2 | 1/2002 |
| WO | WO 02/07783 A2 | 1/2002 |
| WO | WO 02/27017 A2 | 4/2002 |
| WO | WO 02/31500 A2 | 4/2002 |
| WO | WO 02/43758 A2 | 6/2002 |
| WO | WO 02/053596 A2 | 7/2002 |
| WO | WO 02/054066 A2 | 7/2002 |
| WO | WO 02/072780 A2 | 9/2002 |
| WO | WO 2004/087756 A2 | 10/2002 |
| WO | WO 02/088752 A2 | 11/2002 |
| WO | WO 02/092599 A1 | 11/2002 |
| WO | WO 02/102854 A2 | 12/2002 |
| WO | WO 02/102972 A2 | 12/2002 |
| WO | WO 02/102973 A2 | 12/2002 |
| WO | WO 03/000928 A2 | 1/2003 |
| WO | WO 03/14696 A2 | 2/2003 |
| WO | WO 03/027246 A2 | 4/2003 |
| WO | WO 03/039538 A1 | 5/2003 |
| WO | WO 03/059951 A2 | 7/2003 |
| WO | WO 03/088910 A2 | 10/2003 |
| WO | WO 03/100008 A2 | 12/2003 |
| WO | WO 03/100059 A2 | 12/2003 |
| WO | WO 03/106621 A2 | 12/2003 |
| WO | WO 03/106621 A2 | 12/2003 |
| WO | WO 2004/030625 A2 | 4/2004 |
| WO | WO 2004/030627 A2 | 4/2004 |
| WO | WO 2004/056865 A2 | 7/2004 |
| WO | WO 2004/071529 A2 | 8/2004 |
| WO | WO 2004/083248 A1 | 9/2004 |
| WO | WO2004/096224 A2 | 11/2004 |
| WO | WO2004/096224 A3 | 11/2004 |
| WO | WO 2005/005635 A2 | 1/2005 |
| WO | WO 2005/016967 A2 | 2/2005 |
| WO | WO 2005/016970 A2 | 2/2005 |
| WO | WO2005/052005 | 6/2005 |
| WO | WO 2005/061541 A1 | 7/2005 |
| WO | WO2005/117980 A1 | 12/2005 |
| WO | WO2006/013472 A2 | 2/2006 |
| WO | WO2006069202 | 6/2006 |
| WO | WO2006/020258 A2 | 12/2006 |
| WO | WO2007/093008 | 8/2007 |

OTHER PUBLICATIONS

Leventhal et al. (Exp. Cell. Res. 221:179-186 (1995)).*
Singleton et al. (Can. Res. 56:4522-4529 (1996)).*
Maloney et al. (Can. Res. 63:5073-5083 (2003)).*
Jain, Scientific American Jul. 1994 pp. 58-65.*
Chatterjee et al., Cancer Immunol. Imunother., 38:75-82, 1994.*
Dermer, Biotechnology 12: 320, 1994.*
Gura et al., Science vol. 278:1041-1042 (Nov. 1997).*
Seaver, 1994; Genetic Engineering vol. 14(14):10 and 21.*
Rudikoff et al., Proc Natl Acad Sci USA 1982 vol. 79 p. 1979.*
Casset et al. (2003) BBRC 307, 198-205.*
Vajdos et al. (2002) J. Mol. Biol. 320, 415-428.*
Holm et al., Mol. Immunol. 44, 1075-1084, 2007.*
Sequence search alignment for SEQ ID Nos. 2, 4, 6, 8, 10 and 12 against US 20040018191 (Wang et al.), pp. 1-6.*
Sequence search alignment for SEQ ID Nos. 2, 4, 6, 8, 10 and 12 against US 20070059241 (Wang et al.), pp. 1-6.*
Sequence search alignment for SEQ ID Nos. 2, 4, 6, 8, 10 and 12 against US 20070059305 (Wang et al.), pp. 1-6.*
Sequence search alignment for SEQ ID Nos. 8 and 10 against US 20050136063 (Wang et al.), pp. 1-2.*
Sequence search alignment output for SEQ ID No. 13 (see Cohen et al. US 20040202651) pp. 1-3.*
Sequence search alignment output for SEQ ID No. 14 (see Cohen et al. US 20040202651) pp. 1-5.*
Sequence search alignment output for SEQ ID No. 15 (see Cohen et al. US 20040202651) pp. 1-3.*
Sequence search alignment output for SEQ ID No. 19 (see Cohen et al. US 20040202651) pp. 1-5.*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Accession No. AAB27175 GenBank (pp. 1-3 (Nov. 17, 2009)).*
Stefania Benini et al., Inhibition of Insulin-like Growth Factor I Receptor Increases the Antitumor Activity of Doxorubicin and Vincristine Against Ewing's Sarcoma Cells, Clinical Cancer Research, vol. 7, 1790-1797, Jun. 2001.
V.M. Macaulay, Insulin-like Growth Factors and Cancer, Br. J. Cancer, 65, 311-320, 1992.
Mariana Resnicoff et al., The Role of the Insulin-like Growth Factor I Receptor in Transformation and Apoptosis, Kimmel Cancer Institute, Thomas Jefferson University pp. 76-81.
Xiangdang Liu et al., Inhibition of Insulin-like Growth Factor I Receptor Expression in Neuroblastoma Cells Induces the Regression of Established Tumors in Mice, Cancer Research 58, 5432-5438, Dec. 1, 1998.
Jamie L. Resnik et al., Elevated Insulin-like Growth Factor I Receptor Autophosphorylation and Kinase Activity in Human Breast Cancer, Cancer Research 58, 1159-1164, Mar. 15, 1998.
Fredrika Pekonen et al., Receptors for Epidermal Growth Factor and Insulin-like Growth Factor I and Their Relation to Steroid Receptors in Human Breast Cancer, Cancer Research 48, 1343-1347, Mar. 1, 1988.
Quynh T. Rohlik et al., An Antibody to the Receptor for Insulin-like Growth Factor I Inhibits the Growth of MCF-7 Cells in Tissue Culture, Biochemical and Biophysical Research Communications, vol. 149, No. 1, 276-281, 1987.

Carlos L. Arteaga et al., Blockade of the Type I Somatomedin Receptor Inhibits Growth of Human Breast Cancer Cells in Athymic Mice, J. Clin. Invest., vol. 84, 1418-1423, Nov. 1989.

Ted Gansler et al., Rapid Communication Antibody to Type I insulin-like Growth Factor Receptor Inhibits Growth of Wilms' Tumor in Culture and in Athymic Mice, American Journal of Pathology, vol. 135, No. 6, 961-966, Dec. 1989.

Krzysztof Reiss et al., Inhibition of Tumor Growth by a Dominant Negative Mutant of the Insulin-like Growth Factor I Receptor with a Bystander Effect, Clinical Cancer Research, vol. 4, 2647-2655, Nov. 1998.

Carlos L. Arteaga et al., Growth Inhibition of Human Breast Cancer Cells in Vitro with an Antibody Against the Type I Somatomedin Receptor, Cancer Research, 49, 6237-6241, Nov. 15, 1989.

Sandra E. Dunn et al., A Dominant Negative Mutant of the Insulin-like Growth Factor-I Receptor Inhibits the Adhesion, Invasion, and Metastasis of Breast Cancer, Cancer Research, 58, 3353-3361, Aug. 1, 1998.

Peter Burfeind, Antisense RNA to the Type I Insulin-like Growth Factor Receptor Suppresses Tumor Growth and Prevents Invasion by Rate Prostate Cancer Cells In Vivo, Proc. Natl. Acad. Sci. USA, vol. 93 7263-7268, Jul. 1996.

Diane Prager et al., Dominant Negative Inhibition of Tumorigenesis In Vivo by Human Insulin-like Growth Factor I Receptor Mutant, Proc. Natl. Acad. Sci. USA, vol. 91, 2181-2185, Mar. 1994.

Deepali Sachdev, A Chimeric Humanized Single-Chain Antibody Against the Type I Insulin-like Growth Factor (IGF) Receptor Renders Breast Cancer Cells Refractory to the Mitogenic Effects of IGF-1, Cancer Research 63, 627-635, 2003.

Hakam et al., Human Pathology (1999) 30(10): 1128-1133.

Sepp-Lorenzino, Breast Cancer Research and Treatment (1998) 47: 235-253.

R&D Systems catalogue pages—monoclonal Anti-human IGF-IR Antibody MAB391.

Xiong et al., "Growth-stimulatory monoclonal antibodies against human insulin-like growth factor I receptor" Proc. Nat. Acad. Sci. 89: 5356-5360 (1992).

Li et al., "Two new monoclonal antibodies against the α subunit of the human insulin-like growth factor-I receptor" Biochem. Biophys. Res. Comm. 196(1):92-98 (1993).

Kull et al., "Monoclonal antibodies to receptors for insulin and somatomedin-C" J. Biol. Chem. 258(10):6561-6566 (1983).

Butler et al., "Insulin-like growth factor-I receptor signal transduction: at the interface between physiology and cell biology" Comp. Biochem. Physiol. Part (B) 121(1):19-26 (1998).

Chan et al., "Plasma insulin-like growth factor-I and prostate cancer risk: a prospective study" Science. 279(5350):563-566 (1998).

Xie et al., "Expression of insulin-like growth factor-1 receptor in synovial sarcoma: association with an aggressive phenotype" Cancer Res. 59(15):3588-3591 (1999).

Steller et al., "Overexpression of the insulin-like growth factor-1 receptor and autocrine stimulation in human cervical cancer cells" Cancer Res. 56(8):1761-1765 (1996).

Pandini et al., "Insulin and insulin-like growth factor-I (IGF-I) receptor overexpression in breast cancers leads to Insulin/IGF-I hybrid receptor overexpression: evidence for a second mechanism of IGF-I signaling" Clin. Cancer Res. 5(7):1935-1944 (1999).

Webster et al., "Repression of the insulin receptor promoter by the tumor suppressor gene product p53: a possible mechanism for receptor overexpression in breast cancer" Cancer Res. 56(12):2781-2788 (1996).

Ben-Schlomo et al., "Acromegaly" Endocrin. Metab. Clin. N. America 30(3):565-583 (2001).

Li et al., "Single-chain antibodies against human Insulin-like growth factor I receptor: expression, purification, and effect on tumor growth", Cancer Immunol. Immunother. 49: 243-252 (2000).

Burtrum et al., "A fully human monoclonal antibody to the insulin-like growth factor I receptor blocks ligand-dependent signaling and Inhibits human tumor growth in vivo." Cancer Res. Dec. 15, 2003;63(24):8912-21.

Business Wire, "Imclone systems incorporated reports advancements in several pipeline programs" (Jul. 14, 2003).

Zhu, "Monoclonal Antibodies in Cancer-Fourth International Congress (Part II), Colorado Springs, CO, USA" Investigational Drug Database Meeting Report (Sep. 3-6, 2004).

Williams, "American Association for Cancer Research-94th Annual Meeting (Part III)—Overnight Report, Washington, D.C., USA" Investigational Drug Database Meeting Report (Jul. 11-14, 2003).

Imclone Systems, Inc. Form 10-K (filed Mar. 15, 2004).

Holt et al., Domain antibodies: proteins for therapy, Trends in Biotechnology 21(11): 484-490 (2003).

Maloney et al., An Anti-Insulin-like Growth Factor I Receptor Antibody That Is a Potent Inhibitor of Cancer Cell Proliferation, Cancer Research 63, 5073-5083 (2003).

Lu et al., Simultaneous Blockade of Both the Epidermal Growth Factor Receptor and the Insulin-like Growth factor receptor signaling pathways in cancer cells with a XXX human recombinant XXX antibody, J. Bio. Chem.279(4): 2856-65 (2004).

Tang et al., Use of a peptide mimotope to guide the humanization of MRK-16, an anti-P-glycoprotein monoclonal antibody. J Biol Chem. Sep. 24, 1999;274(39):27371-8.

Boylan et al., The anti-proliferative effect of suramin towards tamoxifen-sensitive and resistant human breast cancer cell lines in relation to expression of receptors for epidermal growth factor and insulin-like growth factor-I: growth stimulation in the presence of tamoxifen. Ann Oncol. Feb. 1998;9(2):205-11.

Happerfield et al., The localization of the insulin-like growth factor receptor 1 (IGFR-1) in benign and malignant breast tissue. J Pathol. Dec. 1997;183(4):412-7.

Clarke et al., Type I insulin-like growth factor receptor gene expression in normal human breast tissue treated with oestrogen and progesterone. Br J Cancer. 1997;75(2):251-7.

Van Den Berg et al., Expression of receptors for epidermal growth factor and insulin-like growth factor I by ZR-75-1 human breast cancer cell variants is inversely related: the effect of steroid hormones on Insulin-like growth factor I receptor expression. Br J Cancer. Feb. 1996;73(4):477-81.

Lebon et al., Purification of insulin-like growth factor I receptor from human placental membranes. J Biol Chem. Jun. 15, 1986;261(17):7685-9.

Warren et al., Induction of vascular endothelial growth factor by insulin-like growth factor 1 in colorectal carcinoma. J Biol Chem. Nov. 15, 1996;271(46):29483-8.

Auclair et al., Antiinsulin receptor autoantibodies induce insulin receptors to constitutively associate with insulin receptor substrate-1 and -2 and cause severe cell resistance to both insulin and insulin-like growth factor I. J Clin Endocrinol Metab. Sep. 1999;84(9):3197-3206.

Gori et al., Effects of androgens on the insulin-like growth factor system in an androgen-responsive human osteoblastic cell line. Endocrinology. Dec. 1999;140(12):5579-86.

Kasprzyk et al., Therapy of an animal model of human gastric cancer using a combination of anti-erbB-2 monoclonal antibodies. Cancer Res. May 15, 1992;52(10):2771-6.

Drebin et al., Monoclonal antibodies reactive with distinct domains of the neu oncogene-encoded p185 molecule exert synergistic antitumor effects in vivo. Oncogene. Mar. 1988;2(3):273-7.

Shin et al., Proapoptotic activity of cell-permeable anti-Akt single-chain antibodies. Cancer Res. Apr. 1, 2005;65(7):2815-24.

Lu et al., A fully human recombinant IgG-like bispecific antibody to both the epidermal growth factor receptor and the insulin-like growth factor receptor for enhanced antitumor activity. J Biol Chem. May 20, 2005;280(20):19665-72.

Cohen et al., Combination therapy enhances the inhibition of tumor growth with the fully human anti-type 1 insulin-like growth factor receptor monoclonal antibody CP-751,871. Clin Cancer Res. Mar. 1, 2005;11(5):2063-73.

Wu et al., In vivo effects of the human type I insulin-like growth factor receptor antibody A12 on androgen-dependent and androgen-independent xenograft human prostate tumors. Clin Cancer Res. Apr. 15, 2005;11(8):3065-74.

Goetsch et al., A recombinant humanized anti-insulin-like growth factor receptor type 1 antibody (h7C10) enhances the antitumor activity of vinorelbine and anti-epidermal growth factor receptor therapy against human cancer xenografts. Int J Cancer. Jan. 10, 2005;113(2):316-28.

Granerus et al., Effects of insulin-like growth factor-binding protein 2 and an IGF-type I receptor-blocking antibody on apoptosis in human teratocarcinoma cells in vitro. Cell Biol Int. 2001;25(8):825-8.

Kaliman et al., Antipeptide antibody to the insulin-like growth factor-I receptor sequence 1232-1246 inhibits the receptor kinase activity. J Biol Chem. May 25, 1992;267(15):10645-51.

Rodeck et al., Interactions between growth factor receptors and corresponding monoclonal antibodies in human tumors. J Cell Biochem. Dec. 1987;35(4):315-20.

Iwakiri et al., Autocrine growth of Epstein-Barr virus-positive gastric carcinoma cells mediated by an Epstein-Barr virus-encoded small RNA. Cancer Res. Nov. 1, 2003;63(21):7062-7.

Kiess et al., Human neuroblastoma cells use either insulin-like growth factor-I or insulin-like growth factor-II in an autocrine pathway via the IGF-I receptor: variability of IGF, IGF binding protein (IGFBP) and IGF receptor gene expression and IGF and IGFBP secretion in human neuroblastoma cells in relation to cellular proliferation. Regul Pept. Sep. 26, 1997;72(1):19-29.

Pritchard et al., Synovial fibroblasts from patients with rheumatoid arthritis, like fibroblasts from Graves' disease, express high levels of IL-16 when treated with Igs against insulin-like growth factor-1 receptor. J Immunol. Sep. 1, 2004;173(5):3564-9.

Jackson-Booth et al., Inhibition of the biologic response to insulin-like growth factor I in MCF-7 breast cancer cells by a new monoclonal antibody to the insulin-like growth factor-I receptor. The importance of receptor down-regulation. Horm Metab Res. Nov.-Dec. 2003;35(11-12):850-6.

Carboni et al., Tumor development by transgenic expression of a constitutively active insulin-like growth factor I receptor. Cancer Res. May 1, 2005;65(9):3781-7.

Remacle-Bonnet et al., Insulin-like growth factor-I protects colon cancer cells from death factor-induced apoptosis by potentiating tumor necrosis factor alpha-induced mitogen-activated protein kinase and nuclear factor kappaB signaling pathways. Cancer Res. Apr. 1, 2000;60(7):2007-17.

Lahm et al., Blockade of the insulin-like growth-factor-I receptor inhibits growth of human colorectal cancer cells: evidence of a functional IGF-II-mediated autocrine loop. Int J Cancer. Aug. 1, 1994;58(3):452-9.

Steele-Perkins et al., Monoclonal antibody alpha IR-3 inhibits the ability of insulin-like growth factor II to stimulate a signal from the type I receptor without inhibiting its binding. Biochem Biophys Res Commun. Sep. 28, 1990;171(3):1244-51.

Scotlandi et al., Prognostic and therapeutic relevance of HER2 expression in osteosarcoma and Ewing's sarcoma. Eur J Cancer. Jun. 2005;41(9):1349-61.

Agus et al., Response of prostate cancer to anti-Her-2/neu antibody in androgen-dependent and -independent human xenograft models. Cancer Res. Oct. 1, 1999;59(19):4761-4.

Pietras et al., Monoclonal antibody to HER-2/neureceptor modulates repair of radiation-induced DNA damage and enhances radiosensitivity of human breast cancer cells overexpressing this oncogene. Cancer Res. Mar. 15, 1999;59(6):1347-55.

Goldenberg, Trastuzumab, a recombinant DNA-derived humanized monoclonal antibody, a novel agent for the treatment of metastatic breast cancer. Clin Ther. Feb. 1999;21(2):309-18. Review.

Seely et al., Retroviral expression of a kinase-defective IGF-I receptor suppresses growth and causes apoptosis of CHO and U87 cells in-vivo. BMC Cancer. May 31, 2002;2:15.

Soos et al., A panel of monoclonal antibodies for the type I insulin-like growth factor receptor. Epitope mapping, effects on ligand binding, and biological activity. J Biol Chem. Jun. 25, 1992;267(18):12955-63.

Kalebic et al., In vivo treatment with antibody against IGF-1 receptor suppresses growth of human rhabdomyosarcoma and down-regulates p34cdc2. Cancer Res. Nov. 1, 1994;54(21):5531-4.

Baserga, The insulin-like growth factor I receptor: a key to tumor growth? Cancer Res. Jan. 15, 1995;55(2):249-52.

Rubini et al., Characterization of an antibody that can detect an activated IGF-I receptor in human cancers. Exp Cell Res. Aug. 25, 1999;251(1):22-32.

Lin et al., Structure-function relationships in glucagon: properties of highly purified des-His-1-, monoiodo-, and (des-Asn- 28, Thr-29)(homoserine lactone -27)-glucagon, Biochemistry. Apr. 22, 1975;14(8):1559-63.

Acland et al., Subcellular fate of the int-2 oncoprotein is determined by choice of initiation codon, Nature. Feb. 15, 1990;343(6259):662-5.

Cordera et al., Inhibition of insulin and epidermal growth factor (EGF) receptor autophosphorylation by a human polyclonal 1gG, Biochem Biophys Res Commun. Nov. 15, 1985;132(3):991-1000.

Freund et al., Functional insulin and insulin-like growth factor-1 receptors are preferentially expressed in multiple myeloma cell lines as compared to B-lymphoblastoid cell lines, Cancer Res. Jun. 15, 1994;54(12):3179-85.

Rudikoff et al., Single amino acid substitution altering antigen-binding specificity, Proc Natl Acad Sci U S A. Mar. 1982;79(6):1979-83.

Burgess et al., Possible dissociation of the heparin-binding and mitogenic activities of heparin-binding (acidic fibroblast) growth factor-1 from its receptor-binding activities by site-directed mutagenesis of a single lysine residue, J Cell Biol. Nov. 1990;111:2129-38.

Lazar et al., Transforming growth factor alpha: mutation of aspartic acid 47 and leucine 48 results in different biological activities, Mol Cell Biol. Mar. 1988;8(3):1247-52.

Schwartz et al., A superactive insulin: [B10-aspartic acid]insulin(human), Proc Natl Acad Sci U S A. Sep. 1987;84(18):6408-11.

Jackson et al., Insulin receptor substrate-1 is the predominant signaling molecule activated by insulin-like growth factor-I, insulin, and interleukin-4 in estrogen receptor-positive human breast cancer cells. J Biol Chem. Apr. 17, 1998;273(16):9994-10003.

Desnoyers et al., Novel non-isotopic method for the localization of receptors in tissue sections. J Histochem Cytochem. Dec. 2001;49(12):1509-18.

Ricort et al. Insulin-like growth factor (IGF) binding protein-3 inhibits type 1 IGF receptor activation independently of its IGF binding affinity, Endocrinology. Jan. 2001;142(1):108-13.

International Search Report for application No. PCT/US2005/043184.

Hailey et al., Neutralizing anti-insulin-like growth factor receptor 1 antibodies inhibit receptor function and induce receptor degradation in tumor cells. Mol. Cancer Therap. 1:1349-1353 (2002).

Bagatell et al., Hsp90 inhibitors deplete key anti-apoptotic proteins in pediatric solid tumor cells and demonstrate synergistic anticancer activity with cisplatin. Int J Cancer. Jan. 10, 2005;113(2):179-88.

Baserga, Targeting the IGF-1 receptor: from rags to riches. Eur. J. Cancer. Sep. 2004;40(14):2013-5.

García-Echeverría et al., In vivo antitumor activity of NVP-AEW541—A novel, potent, and selective inhibitor of the IGF-IR kinase. Cancer Cell. Mar. 2004;5(3):231-9.

Resnicoff et al., Rat glioblastoma cells expressing an antisense RNA to the insulin-like growth factor-1 (IGF-1) receptor are nontumorigenic and induce regression of wild-type tumors.Cancer Res. Apr. 15, 1994;54(8):2218-22.

Wittman et al., Discovery of a (1H-benzoimidazol-2-y1)-1H-pyridin-2-one (BMS-536924) inhibitor of insulin-like growth factor I receptor kinase with in vivo antitumor activity.J Med Chem. Sep. 8, 2005;48(18):5639-43.

Clemmons, Modifying IGF1 activity: an approach to treat endocrine disorders, atherosclerosis and cancer.Nat Rev Drug Discov. Oct. 2007;6(10):821-33.

Noble et al., Gemcitabine. A review of its pharmacology and clinical potential in non-small cell lung cancer and pancreatic cancer. Drugs. Sep. 1997;54(3):447-72.

Maloney et al., An anti-insulin-like growth factor I receptor antibody that is a potent inhibitor of cancer cell proliferation. Cancer Res. Aug. 15, 2003;63(16):5073-83.

Pandini et al., Functional responses and in vivo anti-tumour activity of h7c10: a humanised monoclonal antibody with neutralising activity against the insulin-like growth factor-1 (IGF-1) receptor and insulin/IGF-1 hybrid receptors. Eur J Cancer. May 2007;43(8):1318-27.

Burtrum et al., A fully human monoclonal antibody to the insulin-like growth factor I receptor blocks ligand-dependent signaling and inhibits human tumor growth in vivo.Cancer Res. Dec. 15, 2003;63(24):8912-21.

Cohen et al., Combination therapy enhances the inhibition of tumor growth with the fully human anti-type 1 insulin-like growth factor receptor monoclonal antibody CP-751,871.Clin Cancer Res. Mar. 1, 2005;11(5):2063-73.

Ji et al., A novel, potent, and selective insulin-like growth factor-I receptor kinase inhibitor blocks insulin-like growth factor-I receptor signaling in vitro and inhibits insulin-like growth factor-I receptor dependent tumor growth in vivo.Mol Cancer Ther. Aug. 2007;6(8):2158-67.

Yang et al., Thrombospondin-1 peptide ABT-510 combined with valproic acid is an effective antiangiogenesis strategy in neuroblastoma.Cancer Res. Feb. 15, 2007;67(4):1716-24.

Yeo et al., YC-1: a potential anticancer drug targeting hypoxia-inducible factor 1.J Natl Cancer Inst. Apr. 2, 2003;95(7):516-25.

Albert et al., Responsiveness of human retinoblastoma and neuroblastoma models to a non-calcemic 19-nor Vitamin D analog. J Steroid Biochem Mol Biol. Oct. 2005;97(1-2):165-72.

Wagner et al., Targeting methylguanine-DNA methyltransferase in the treatment of neuroblastoma. Clin Cancer Res. Sep. 15, 2007;13(18 Pt 1):5418-25.

Armstrong et al., Molecular targeting of retinoic acid metabolism in neuroblastoma: the role of the CYP26 inhibitor R116010 in vitro and in vivo. Br J Cancer. Jun. 4, 2007;96(11):1675-83.

Beech et al., Insulin-like growth factor-I receptor antagonism results in increased cytotoxicity of breast cancer cells to doxorubicin and taxol, Oncology Reports (2001) 8:325-329.

Pollak et al., Insulin-like growth factors and neoplasiaNat Rev Cancer. Jul. 2004;4(7):505-18.

Herceptin®: US BLA supplement.

Clinicaltrials.gov entry: A phase 2 study of AMG479 in relapsed or refractory Ewing's family tumor and desmoplastic small round cell tumors.

Clinicaltrials.gov entry: Phase 2 study of CP-751871 in combination with docetaxel and prednisone in patients with hormone insensitive prostate cancer (HRPC).

Clinicaltrials.gov entry: Study using IMC-A12 with or without cetuximab in patients with metastatic colorectal cancer who have failed a treatment regimen that consisted of a prior anti-EGFr therapy.

Clinicaltrials.gov entry: A study of R1507 in patients with recurrent or refractory sarcoma.

Clinicaltrials.gov entry: A study to determine the activity of SCH717454 in subjects with relapsed osteosarcoma or Ewing's sarcoma (Study P04720).

Clinicaltrials.gov entry: Preoperative Octreotide Treatment of Acromegaly (POTA).

Clinicaltrials.gov entry: Study of XL228 Administered Intravenously to Subjects With Advanced Malignancies.

Niu T, Rosen CJ. The insulin-like growth factor-I gene and osteoporosis: a critical appraisal. Gene. Nov. 21, 2005;361:38-56.

Steele-Perkins G, Turner J, Edman JC, Hari J, Pierce SB, Stover C, Rutter WJ, Roth RA. Expression and characterization of a functional human insulin-like growth factor I receptor. J Biol Chem. Aug. 15, 1988;263(23):11486-11492.

Chang Q, Li Y, White MF, Fletcher JA, Xiao S. Constitutive activation of insulin receptor substrate 1 is a frequent event in human tumors: therapeutic implications. Cancer Res. Nov. 1, 2002;62(21):6035-6038.

Kolb EA, Gorlick R, Houghton PJ, Morton CL, Lock R, Carol H, Reynolds CP, Maris JM, Keir ST, Billups CA, Smith MA. Initial testing (stage 1) of a monoclonal antibody (SCH 717454) against the IGF-1 receptor by the pediatric preclinical testing program. Pediatr Blood Cancer. Jun. 2008;50(6):1190-1197.

Lopaczynski W, Terry C. Insulin-like growth factor I activates insulin receptor substrate 1 and Ras in human osteosarcoma cells. Acta Biochim Pol. 1999;46(1):117-123.

Wang et al. Inhibition of insulin-like growth factor-I receptor (IGF-IR) signaling and tumor cell growth by a fully human neutralizing anti-IGF-IR antibody. Mol Cancer Ther. Aug. 2005;4(8):1214-21.

International Non-proprietary Names for Pharmaceutical Substances (INN), Cumulative list No. 12, 2007.

Statement on a Nonproprietary Name Adopted by the USAN Council (2008).

* cited by examiner

Fig. 2

| Tumor Type | Cell Line | Maximal Tumor Growth Inhibition |
|---|---|---|
| NSCLC | H322 | 64-102% |
| NSCLC | H838 | 24% |
| Ovarian | A2780 | 56-63% |
| Ovarian | ES2 | 30% |
| Breast (ER+) | MCF7 | 68% |
| Breast (ER-) | SW-527 | 56% |
| Neuroblastoma | SK-N-AS | 82-87% |
| Neuroblastoma | SK-N-MC | 59% |

BIOMARKERS FOR PRE-SELECTION OF PATIENTS FOR ANTI-IGF1R THERAPY

The present application claims the benefit of U.S. provisional patent application No. 60/633,156; filed Dec. 3, 2004, which is herein incorporated by reference in its entirety.

FIELD OF THE INVENTION

The present invention relates to methods for selecting patients for anti-cancer therapy.

BACKGROUND OF THE INVENTION

The insulin-like growth factors, also known as somatomedins, include insulin-like growth factor-I (IGF-I) and insulin-like growth factor-II (IGF-II) (Klapper, et al., (1983) Endocrinol. 112:2215 and Rinderknecht, et al., (1978) Febs. Lett. 89:283). These growth factors exert mitogenic activity on various cell types, including tumor cells (Macaulay, (1992) Br. J. Cancer 65:311), by binding to a common receptor named the insulin-like growth factor receptor-1 (IGF1R) (Sepp-Lorenzino, (1998) Breast Cancer Research and Treatment 47:235). Interaction of IGFs with IGF1R activates the receptor by triggering autophosphorylation of the receptor on tyrosine residues (Butler, et al., (1998) Comparative Biochemistry and Physiology 121:19). Once activated, IGF1R, in turn, phosphorylates intracellular targets to activate cellular signaling pathways. This receptor activation is critical for stimulation of tumor cell growth and survival. Therefore, inhibition of IGF1R activity represents a valuable potential method to treat or prevent growth of human cancers and other proliferative diseases.

Several lines of evidence indicate that IGF-I, IGF-II and their receptor IGF1R are important mediators of the malignant phenotype. Plasma levels of IGF-I have been found to be the strongest predictor of prostate cancer risk (Chan, et al., (1998) Science 279:563) and similar epidemiological studies strongly link plasma IGF-I levels with breast, colon and lung cancer risk.

Overexpression of Insulin-like Growth Factor Receptor-1 has also been demonstrated in several cancer cell lines and tumor tissues. IGF1R is overexpressed in 40% of all breast cancer cell lines (Pandini, et al., (1999) Cancer Res. 5:1935) and in 15% of lung cancer cell lines. In breast cancer tumor tissue, IGF1R is overexpressed 6-14 fold and IGF1R exhibits 2-4 fold higher kinase activity as compared to normal tissue (Webster, et al., (1996) Cancer Res. 56:2781 and Pekonen, et al., (1998) Cancer Res. 48:1343). Ninety percent of colorectal cancer tissue biopsies exhibit elevated IGF1R levels wherein the extent of IGF1R expression is correlated with the severity of the disease. Analysis of primary cervical cancer cell cultures and cervical cancer cell lines revealed 3- and 5-fold overexpression of IGF1R, respectively, as compared to normal ectocervical cells (Steller, et al., (1996) Cancer Res. 56:1762). Expression of IGF1R in synovial sarcoma cells also correlated with an aggressive phenotype (i.e., metastasis and high rate of proliferation; Xie, et al., (1999) Cancer Res. 59:3588).

Currently, there are several known anti-cancer therapies that target IGF1R. For example, anti-IGF1R antibodies are owned by Schering Corp (see WO 2003/100008); Pfizer (see WO 2002/53596 or WO 2004/71529); Pierre Fabre medicament (see WO 2003/59951), Pharmacia Corp. (see WO 2004/83248), Immunogen, Inc. (see WO 2003/106621), Hoffman La Roche (see WO 2004/87756) and Imclone Systems Inc. (IMC-A12; see Burtrum et. al Cancer Research 63:8912-8921(2003)). Additionally, Novartis owns a small molecule IGFR inhibitor, NVP-ADW-742 (see WO 2002/92599) as does Biotech Research Ventures PTE Ltd (see WO 2003/39538). Antisense Therapeutics Ltd. also owns an anti-sense therapy that inhibits IGF1R expression, ATL-1101.

Agents that decrease IGF1R function and/or expression are effective in the treatment of some cancer patients. However, it is expected that a portion of cancer patients may not respond to such treatments. Therefore, a need exists in the art for a method to identify specific cancer populations and/or specific cancer patients who are most likely to respond to one or more anti-cancer therapies that target IGF1R.

SUMMARY OF THE INVENTION

The present invention provides, inter alia, a method for treating cancers by pre-selecting patients whose tumors express appreciable levels of IGF-II and/or phosphorylated IRS-1 (insulin receptor substrate-1), thereby increasing the likelihood of a response, in the patient, to therapeutics targeting IGF1R.

The present invention provides a method for treating a tumor in a patient comprising (a) selecting a patient or patient population having a tumor known to express one or more of the following:
 (i) IRS-1 phosphorylation on tyrosine 896;
 (ii) IRS-1 phosphorylation on tyrosine 612;
 (iii) IRS-1 phosphorylation on any tyrosine;
 (iv) IGF-II;
 (v) IGF1R phosphorylation on any tyrosine; or
 (vi) IGF1R; and (b) administering to said patient a therapeutically effective amount of an IGF1R inhibitory agent.

The present invention comprises a method for treating a tumor in a patient comprising: (a) selecting a patient having a tumor expressing one or more of the following:
 (i) IRS-1 phosphorylation on tyrosine 896;
 (ii) IRS-1 phosphorylation on tyrosine 612;
 (iii) IRS-1 phosphorylation on any tyrosine;
 (iv) IGF-II;
 (v) IGF1R phosphorylation on any tyrosine; or
 (vi) IGF1R; and (b) administering to said patient a therapeutically effective amount of an IGF1R inhibitory agent. In an embodiment of the invention, the cancer is selected from the group consisting of bladder cancer, Wilm's cancer, bone cancer, prostate cancer, lung cancer, non-small cell lung cancer (NSCLC), colon cancer, rectal cancer, colorectal cancer, endometrial cancer, multiple myeloma, estrogen receptor-positive breast cancer, estrogen receptor-negative breast cancer, cervical cancer, synovial sarcoma, ovarian cancer, pancreatic cancer, neuroblastoma, rhabdomyosarcoma, osteosarcoma and vasoactive intestinal peptide secreting tumors. In an embodiment of the invention, the agent is selected from the group consisting of an isolated antibody or antigen-binding fragment thereof that binds specifically to human IGF1R and is a member selected from the group consisting of: (i) an isolated antibody or antigen-binding fragment thereof that binds specifically to human IGF1R comprising one or more CDRs from a light chain variable region comprising amino acids 20-128 of SEQ ID NO: 8 and/or one or more CDRs from a heavy chain variable region comprising amino acids 20-137 of SEQ ID NO: 10; (ii) an isolated antibody or antigen-binding fragment thereof comprising one or more CDRs from a heavy chain immunoglobulin comprising the amino acid sequence of SEQ ID NO: 2, 4, 6, 8, 19-28, 35-38, 43, 45 or 73-98;

(iii) an isolated antibody or antigen-binding fragment thereof comprising one or more CDRs from a light chain immunoglobulin comprising the amino acid sequence of SEQ ID NO: 10, 12-18, 29-34, 39, 40, 41, 42, 44 or 58-72; and (iv) an isolated single-chain antibody (scfv) comprising an amino acid sequence selected from the group consisting of SEQ ID NOs: 46-51; or (v)

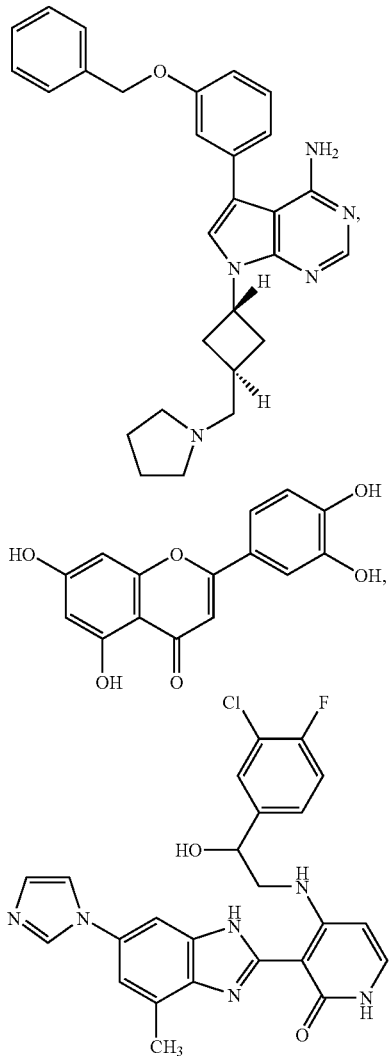

or ATL-1101. In an embodiment of the invention, the isolated antibody or antigen-binding fragment thereof comprises: (i) an isolated immunoglobulin heavy chain comprising an amino acid sequence selected from the group consisting of SEQ ID NOs: 2, 4, 6, 8, 19-28, 35-38, 43, 45 and 73-98; (ii) an isolated immunoglobulin light chain comprising an amino acid sequence selected from the group consisting of SEQ ID NOs: 10, 12-18, 29-34, 39, 40, 41, 42, 44 and 58-72; (iii) an isolated antibody produced by a hybridoma deposited at the American Type Culture Collection under deposit number PTA-2792, PTA-2788, PTA-2790, PTA-2791, PTA-2789 or PTA-2793; (iv) an isolated antibody or antigen-binding fragment thereof that binds specifically to human IGF1R comprising a light chain variable region comprising amino acids 20-128 of SEQ ID NO: 8 and/or a heavy chain variable region comprising amino acids 20-137 of SEQ ID NO: 10; and/or (v) an isolated antibody comprising an immunoglobulin light chain encoded by the plasmid contained in the cell line deposited at the American Type Culture Collection under deposit number PTA-5220 and an immunoglobulin heavy chain encoded by the plasmid contained in a cell line deposited at the American Type Culture Collection under deposit number PTA-5214 or PTA-5216. In an embodiment of the invention, phosphorylation of tyrosine on IRS-1 or IGF1R is determined by western blot analysis, ELISA or flow cytometry analysis. In an embodiment of the invention, IGF-II expression is determined by western blot analysis, ELISA, quantitative PCR or by northern blot analysis. In an embodiment of the invention, IGF1R expression is determined by western blot analysis or ELISA.

The present invention provides a method for selecting a therapy for a patient or a patient population with a tumor, comprising: (a) determining whether the patient's tumor is known to express one or more of the following:

(i) IRS-1 phosphorylation on tyrosine 896;
(ii) IRS-1 phosphorylation on tyrosine 612;
(iii) IRS-1 phosphorylation on any tyrosine;
(iv) IGF-II;
(v) IGF1R phosphorylation on any tyrosine; or
(vi) IGF1R; and/or (b) determining whether the patient's tumor expresses one or more of the following:

(i) IRS-1 phosphorylation on tyrosine 896;
(ii) IRS-1 phosphorylation on tyrosine 612;
(iii) IRS-1 phosphorylation on any tyrosine;
(iv) IGF-II;
(v) IGF1R phosphorylation on any tyrosine; or
(vi) IGF1R; and (c) selecting an IGF1R inhibitory agent as the therapy if the patient's tumor is known to express one or more of (i)-(vi) and/or if the patient's tumor expresses one or more of (i)-(vi). In an embodiment of the invention, the agent is selected from the group consisting of an isolated antibody or antigen-binding fragment thereof that binds specifically to human IGF1R and is a member selected from the group consisting of: (i) an isolated antibody or antigen-binding fragment thereof that binds specifically to human IGF1R comprising one or more CDRs from a light chain variable region comprising amino acids 20-128 of SEQ ID NO: 8 and/or a one or more CDRs from a heavy chain variable region comprising amino acids 20-137 of SEQ ID NO: 10; (ii) an isolated antibody or antigen-binding fragment thereof comprising one or more CDRs from a heavy chain immunoglobulin comprising the amino acid sequence of SEQ ID NO: 2, 4, 6, 8, 19-28, 35-38, 43, 45 or 73-98; (iii) an isolated antibody or antigen-binding fragment thereof comprising one or more CDRs from a light chain immunoglobulin comprising the amino acid sequence of SEQ ID NO: 10, 12-18, 29-34, 39, 40, 41, 42, 44 or 58-72; and (iv) an isolated single-chain antibody (scfv) comprising an amino acid sequence selected from the group consisting of SEQ ID NOs: 46-51; or

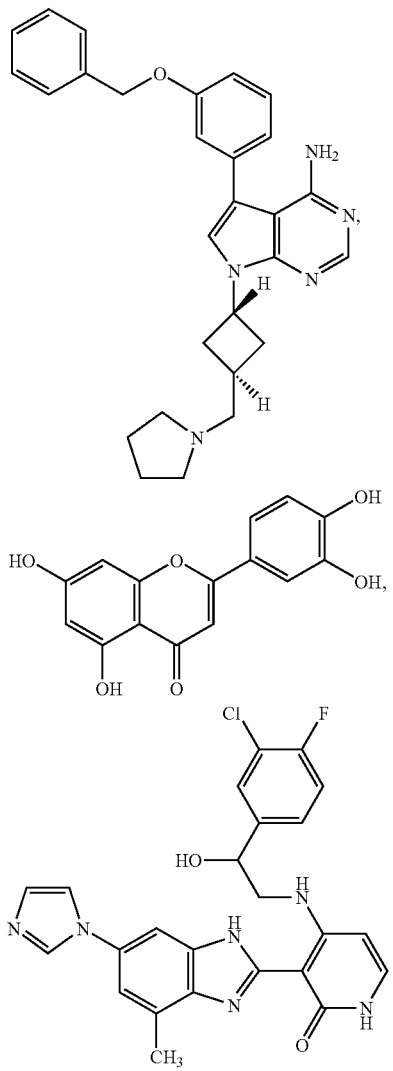

(V)

or ATL-1101. In an embodiment of the invention, the isolated antibody or antigen-binding fragment thereof comprises: (i) an isolated immunoglobulin heavy chain comprising an amino acid sequence selected from the group consisting of SEQ ID NOs: 2, 4, 6, 8, 19-28, 35-38, 43, 45 and 73-98; (ii) an isolated immunoglobulin light chain comprising an amino acid sequence selected from the group consisting of SEQ ID NOs: 10, 12-18, 29-34, 39, 40, 41, 42, 44 and 58-72; (iii) an isolated antibody produced by a hybridoma deposited at the American Type Culture Collection under deposit number PTA-2792, PTA-2788, PTA-2790, PTA-2791, PTA-2789 or PTA-2793; (iv) an isolated antibody or antigen-binding fragment thereof that binds specifically to human IGF1R comprising a light chain variable region comprising amino acids 20-128 of SEQ ID NO: 8 and/or a heavy chain variable region comprising amino acids 20-137 of SEQ ID NO: 10; and/or (v) an isolated antibody comprising an immunoglobulin light chain encoded by the plasmid contained in the cell line deposited at the American Type Culture Collection under deposit number PTA-5220 and an immunoglobulin heavy chain encoded by the plasmid contained in a cell line deposited at the American Type Culture Collection under deposit number PTA-5214 or PTA-5216.

The present invention also provides a method for advertising an IGF1R inhibitory agent or a pharmaceutically acceptable composition thereof comprising promoting, to a target audience, the use of the agent or pharmaceutical composition thereof for treating a patient or patient population whose tumors express or are known to express one or more of the following:

(i) IRS-1 phosphorylation on tyrosine 896;
(ii) IRS-1 phosphorylation on tyrosine 612;
(iii) IRS-1 phosphorylation on any tyrosine;
(iv) IGF-II;
(v) IGF1R phosphorylation on any tyrosine; or
(vi) IGF1R.

In an embodiment of the invention, the agent is selected from the group consisting of an isolated antibody or antigen-binding fragment thereof that binds specifically to human IGF1R and is a member selected from the group consisting of: (i) an isolated antibody or antigen-binding fragment thereof that binds specifically to human IGF1R comprising one or more CDRs from a light chain variable region comprising amino acids 20-128 of SEQ ID NO: 8 and/or one or more CDRs from a heavy chain variable region comprising amino acids 20-137 of SEQ ID NO: 10; (ii) an isolated antibody or antigen-binding fragment thereof comprising one or more CDRs from a heavy chain immunoglobulin comprising the amino acid sequence of SEQ ID NO: 2, 4, 6, 8, 19-28, 35-38, 43, 45 or 73-98; (iii) an isolated antibody or antigen-binding fragment thereof comprising one or more CDRs from a light chain immunoglobulin comprising the amino acid sequence of SEQ ID NO: 10, 12-18, 29-34, 39, 40, 41, 42, 44 or 58-72; and (iv) an isolated single-chain antibody (scfv) comprising an amino acid sequence selected from the group consisting of SEQ ID NOs: 46-51; or (V)

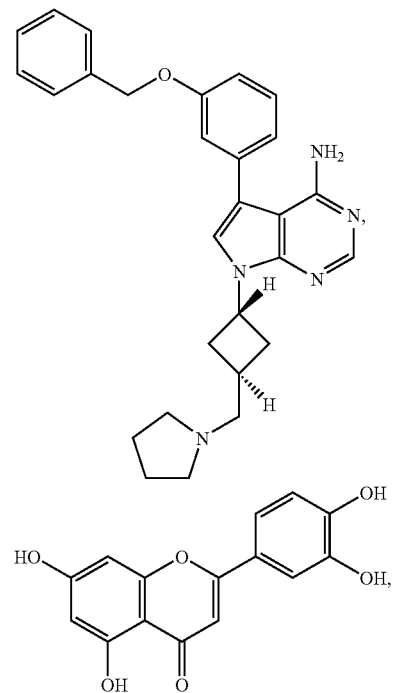

-continued

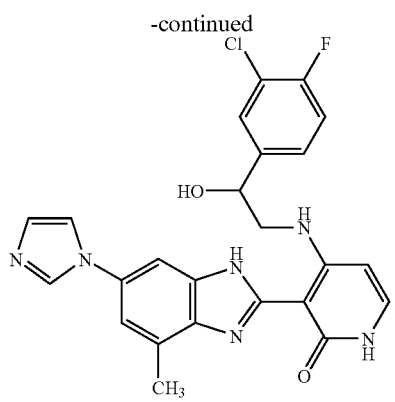

or ATL-1101. In an embodiment of the invention, the isolated antibody or antigen-binding fragment thereof comprises: (i) an isolated immunoglobulin heavy chain comprising an amino acid sequence selected from the group consisting of SEQ ID NOs: 2, 4, 6, 8, 19-28, 35-38, 43, 45 and 73-98; (ii) an isolated immunoglobulin light chain comprising an amino acid sequence selected from the group consisting of SEQ ID NOs: 10, 12-18, 29-34, 39, 40, 41, 42, 44 and 58-72; (iii) an isolated antibody produced by a hybridoma deposited at the American Type Culture Collection under deposit number PTA-2792, PTA-2788, PTA-2790, PTA-2791, PTA-2789 or PTA-2793; (iv) an isolated antibody or antigen-binding fragment thereof that binds specifically to human IGF1R comprising a light chain variable region comprising amino acids 20-128 of SEQ ID NO: 8 and/or a heavy chain variable region comprising amino acids 20-137 of SEQ ID NO: 10; and/or (v) an isolated antibody comprising an immunoglobulin light chain encoded by the plasmid contained in the cell line deposited at the American Type Culture Collection under deposit number PTA-5220 and an immunoglobulin heavy chain encoded by the plasmid contained in a cell line deposited at the American Type Culture Collection under deposit number PTA-5214 or PTA-5216.

The present invention also provides an article of manufacture comprising, packaged together, a pharmaceutical composition comprising an IGF1R inhibitory agent and a pharmaceutically acceptable carrier and a label stating that the agent or pharmaceutical composition is indicated for treating patients having a tumor expressing or known to express one or more of the following:
  (i) IRS-1 phosphorylation on tyrosine 896;
  (ii) IRS-1 phosphorylation on tyrosine 612;
  (iii) IRS-1 phosphorylation on any tyrosine;
  (iv) IGF-II;
  (v) IGF1R phosphorylation on any tyrosine; or
  (vi) IGF1R.

In an embodiment of the invention, the agent is selected from the group consisting of an isolated antibody or antigen-binding fragment thereof that binds specifically to human IGF1R and is a member selected from the group consisting of: (i) an isolated antibody or antigen-binding fragment thereof that binds specifically to human IGF1R comprising one or more CDRs from a light chain variable region comprising amino acids 20-128 of SEQ ID NO: 8 and/or a one or more CDRs from a heavy chain variable region comprising amino acids 20-137 of SEQ ID NO: 10; (ii) an isolated antibody or antigen-binding fragment thereof comprising one or more CDRs from a heavy chain immunoglobulin comprising the amino acid sequence of SEQ ID NO: 2, 4, 6, 8, 19-28, 35-38, 43, 45 or 73-98; (iii) an isolated antibody or antigen-binding fragment thereof comprising one or more CDRs from a light chain immunoglobulin comprising the amino acid sequence of SEQ ID NO: 10, 12-18, 29-34, 39, 40, 41, 42, 44 or 58-72; and (iv) an isolated single-chain antibody (scfv) comprising an amino acid sequence selected from the group consisting of SEQ ID NOs: 46-51; or (V)

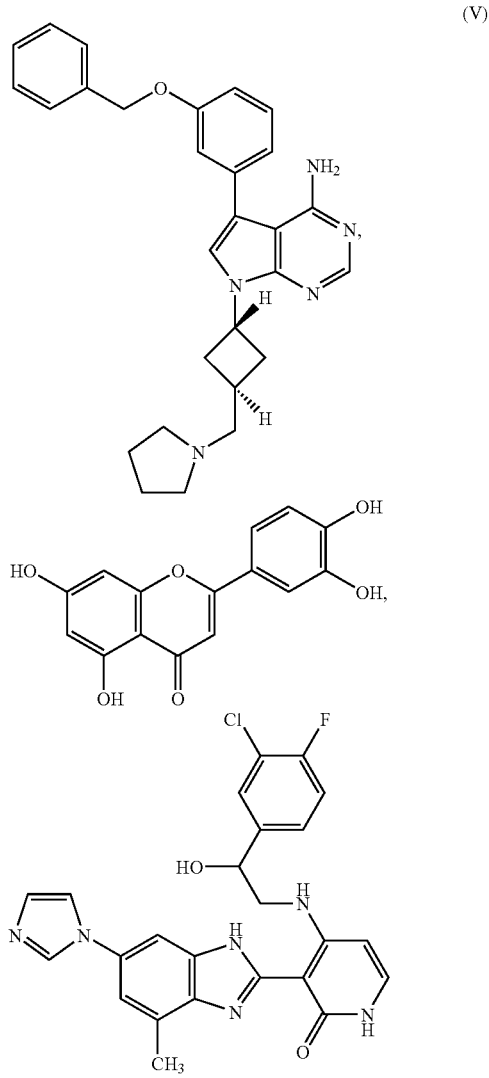

or ATL-1101. In an embodiment of the invention, the isolated antibody or antigen-binding fragment thereof comprises: (i) an isolated immunoglobulin heavy chain comprising an amino acid sequence selected from the group consisting of SEQ ID NOs: 2, 4, 6, 8, 19-28, 35-38, 43, 45 and 73-98; (ii) an isolated immunoglobulin light chain comprising an amino acid sequence selected from the group consisting of SEQ ID NOs: 10, 12-18, 29-34, 39, 40, 41, 42, 44 and 58-72; (iii) an isolated antibody produced by a hybridoma deposited at the American Type Culture Collection under deposit number PTA-2792, PTA-2788, PTA-2790, PTA-2791, PTA-2789 or PTA-2793; (iv) an isolated antibody or antigen-binding fragment thereof that binds specifically to human IGF1R comprising a light chain variable region comprising amino acids 20-128 of SEQ ID NO: 8 and/or a heavy chain variable region comprising amino acids 20-137 of SEQ ID NO: 10; and/or (v) an isolated antibody comprising an immunoglobulin light chain encoded by the plasmid contained in the cell line deposited at the American Type Culture Collection under deposit number PTA-5220 and an immunoglobulin heavy chain encoded by the plasmid contained in a cell line deposited at the American Type Culture Collection under deposit number PTA-5214 or PTA-5216.

The present invention further provides a method for manufacturing an IGF1R inhibitory agent or a pharmaceutical composition thereof comprising combining in a package the agent or pharmaceutical composition and a label stating that the agent or pharmaceutical composition is indicated for treating patients having a tumor expressing or known to express one or more of the following:

(i) IRS-1 phosphorylation on tyrosine 896;

(ii) IRS-1 phosphorylation on tyrosine 612;

(iii) IRS-1 phosphorylation on any tyrosine;

(iv) IGF-II;

(v) IGF1R phosphorylation on any tyrosine; or (vi) IGF1R.

In an embodiment of the invention, the agent is selected from the group consisting of an isolated antibody or antigen-binding fragment thereof that binds specifically to human IGF1R and is a member selected from the group consisting of: (i) an isolated antibody or antigen-binding fragment thereof that binds specifically to human IGF1R comprising one or more CDRs from a light chain variable region comprising amino acids 20-128 of SEQ ID NO: 8 and/or a one or more CDRs from a heavy chain variable region comprising amino acids 20-137 of SEQ ID NO: 10; (ii) an isolated antibody or antigen-binding fragment thereof comprising one or more CDRs from a heavy chain immunoglobulin comprising the amino acid sequence of SEQ ID NO: 2, 4, 6, 8, 19-28, 35-38, 43, 45 or 73-98; (iii) an isolated antibody or antigen-binding fragment thereof comprising one or more CDRs from a light chain immunoglobulin comprising the amino acid sequence of SEQ ID NO: 10, 12-18, 29-34, 39, 40, 41, 42, 44 or 58-72; and (iv) an isolated single-chain antibody (scfv) comprising an amino acid sequence selected from the group consisting of SEQ ID NOs: 46-51;

(V)

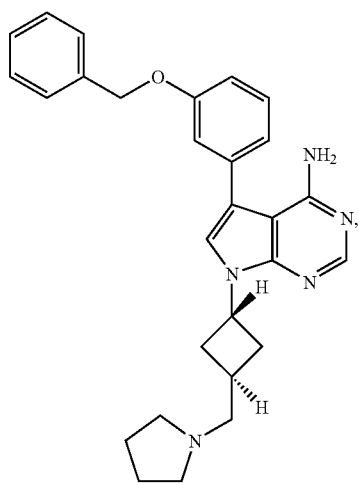

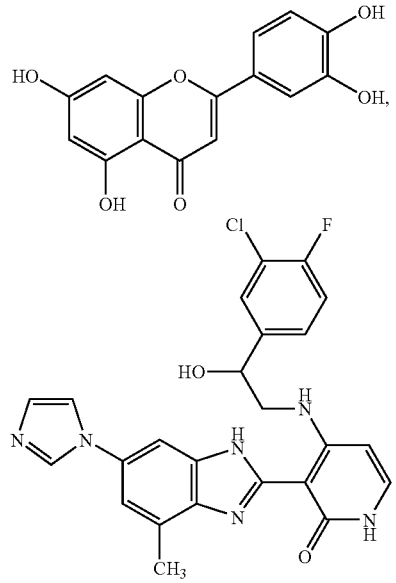

or ATL-1101. In an embodiment of the invention, the isolated antibody or antigen-binding fragment thereof comprises: (i) an isolated immunoglobulin heavy chain comprising an amino acid sequence selected from the group consisting of SEQ ID NOs: 2, 4, 6, 8, 19-28, 35-38, 43, 45 and 73-98; (ii) an isolated immunoglobulin light chain comprising an amino acid sequence selected from the group consisting of SEQ ID NOs: 10, 12-18, 29-34, 39, 40, 41, 42, 44 and 58-72; (iii) an isolated antibody produced by a hybridoma deposited at the American Type Culture Collection under deposit number PTA-2792, PTA-2788, PTA-2790, PTA-2791, PTA-2789 or PTA-2793; (iv) an isolated antibody or antigen-binding fragment thereof that binds specifically to human IGF1R comprising a light chain variable region comprising amino acids 20-128 of SEQ ID NO: 8 and/or a heavy chain variable region comprising amino acids 20-137 of SEQ ID NO: 10; and/or (v) an isolated antibody comprising an immunoglobulin light chain encoded by the plasmid contained in the cell line deposited at the American Type Culture Collection under deposit number PTA-5220 and an immunoglobulin heavy chain encoded by the plasmid contained in a cell line deposited at the American Type Culture Collection under deposit number PTA-5214 or PTA-5216.

The present invention also provides a method for identifying a patient whose tumor is likely to be responsive to an IGF1R inhibitory agent comprising: (a) determining whether the patient has a tumor known to express one or more of the following:

(i) IRS-1 phosphorylation on tyrosine 896;

(ii) IRS-1 phosphorylation on tyrosine 612;

(iii) IRS-1 phosphorylation on any tyrosine;

(iv) IGF-II;

(v) IGF1R phosphorylation on any tyrosine; or (vi) IGF1R; and/or (b) determining whether the patient has a tumor expressing one or more of the following:

(i) IRS-1 phosphorylation on tyrosine 896;

(ii) IRS-1 phosphorylation on tyrosine 612;

(iii) IRS-1 phosphorylation on any tyrosine;

(iv) IGF-II;

(v) IGF1R phosphorylation on any tyrosine; or
(vi) IGF1R.

In an embodiment of the invention, the agent is selected from the group consisting of an isolated antibody or antigen-binding fragment thereof that binds specifically to IGF1R and is a member selected from the group consisting of: (i) an isolated antibody or antigen-binding fragment thereof that binds specifically to human IGF1R comprising one or more CDRs from a light chain variable region comprising amino acids 20-128 of SEQ ID NO: 8 and/or a one or more CDRs from a heavy chain variable region comprising amino acids 20-137 of SEQ ID NO: 10; (ii) an isolated antibody or antigen-binding fragment thereof comprising one or more CDRs from a heavy chain immunoglobulin comprising the amino acid sequence of SEQ ID NO: 2, 4, 6, 8, 19-28, 35-38, 43, 45 or 73-98; (iii) an isolated antibody or antigen-binding fragment thereof comprising one or more CDRs from a light chain immunoglobulin comprising the amino acid sequence of SEQ ID NO: 10, 12-18, 29-34, 39, 40, 41, 42, 44 or 58-72; and (iv) an isolated single-chain antibody (scfv) comprising an amino acid sequence selected from the group consisting of SEQ ID NOs: 46-51; or (v)

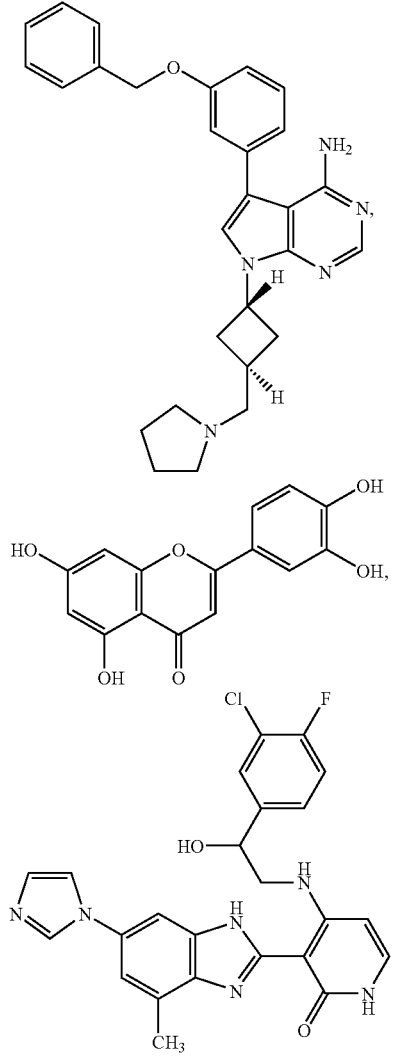

or ATL-1101. In an embodiment of the invention, the isolated antibody or antigen-binding fragment thereof comprises: (i) an isolated immunoglobulin heavy chain comprising an amino acid sequence selected from the group consisting of SEQ ID NOs: 2, 4, 6, 8, 19-28, 35-38, 43, 45 and 73-98; (ii) an isolated immunoglobulin light chain comprising an amino acid sequence selected from the group consisting of SEQ ID NOs: 10, 12-18, 29-34, 39, 40, 41, 42, 44 and 58-72; (iii) an isolated antibody produced by a hybridoma deposited at the American Type Culture Collection under deposit number PTA-2792, PTA-2788, PTA-2790, PTA-2791, PTA-2789 or PTA-2793; (iv) an isolated antibody or antigen-binding fragment thereof that binds specifically to human IGF1R comprising a light chain variable region comprising amino acids 20-128 of SEQ ID NO: 8 and/or a heavy chain variable region comprising amino acids 20-137 of SEQ ID NO: 10; and/or (v) an isolated antibody comprising an immunoglobulin light chain encoded by the plasmid contained in the cell line deposited at the American Type Culture Collection under deposit number PTA-5220 and an immunoglobulin heavy chain encoded by the plasmid contained in a cell line deposited at the American Type Culture Collection under deposit number PTA-5214 or PTA-5216.

BRIEF DESCRIPTION OF THE FIGURES

FIG. 2. Antibody 19D12/15H12 LCF/HCA: In Vivo Efficacy. The level of tumor growth inhibition observed in xenograft mice administered antibody 19D12/15H12 LCF/HCA is indicated along with the type of tumor evaluated and the cell line used to establish each tumor.

DETAILED DESCRIPTION OF THE INVENTION

Figure 1:
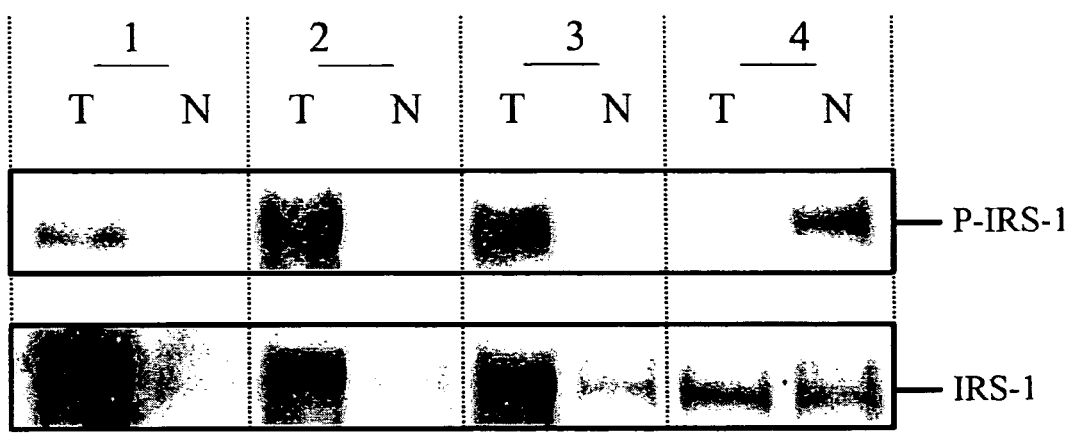
FIG. 1. IRS-1 Phosphorylation is Higher in Human Lung Tumor vs. Normal Tissue Samples. Western blot analysis results for normal and tumor tissue samples from four different patients. Lanes marked "T" contained tumor tissue and lanes marked "N" contained normal tissue.

The present invention provides a method for treating cancer or for identifying patients whose cancer is likely to be responsive to an IGF1R inhibitory agent. The method is useful, inter alia, for increasing the likelihood that administration of an IGF1R inhibitory anti-cancer therapy to a patient will be efficacious.

The terms "IGF1R", "IGFR1", "Insulin-like Growth Factor Receptor-I" and "Insulin-like Growth Factor Receptor, type I" are well known in the art. Although IGF1R may be from any organism, it is preferably from an animal, more preferably from a mammal (e.g., mouse, rat, rabbit, sheep or dog) and most preferably from a human. The nucleotide and amino acid sequence of a typical human IGF1R precursor has the Genbank Accession No. X04434 or NM_000875. Cleavage of the precursor (e.g., between amino acids 710 and 711) produces an α-subunit and a β-subunit which associate to form a mature receptor.

The terms "IGF-I" "Insulin-like Growth Factor-I" and "Insulin-like Growth Factor, type I" are also well known in the art. The terms "IGF-II" "Insulin-like Growth Factor-II" and "Insulin-like Growth Factor, type II" are also well known in the art. Although IGF-I or IGF-II may be from any organism, they are preferably from an animal, more preferably from a mammal (e.g., mouse, rat, rabbit, sheep or dog) and most preferably from a human. The nucleic acid and amino acid sequence of typical, human IGF-I and IGF-II have the Genbank Accession No. XM_052648 and NM_000612, respectively.

IGF1R Inhibitory Agents

The term "IGF1R inhibitory agent" includes any substance that decreases the expression, ligand binding, kinase activity or any other biological activity of IGF1R that will elicit a biological or medical response of a tissue, system, subject or patient that is being sought by the administrator (such as a researcher, doctor or veterinarian) which includes any measurable alleviation of the signs, symptoms and/or clinical indicia of cancer (e.g., tumor growth) and/or the prevention, slowing or halting of progression or metastasis of cancer to any degree.

In an embodiment of the invention, an IGF1R inhibitory agent that can be administered to a patient in a method according to the invention is any isolated anti-insulin-like growth factor receptor-1 (IGF1R) antibody or fragment thereof (e.g., monoclonal antibodies (e.g., fully human monoclonal antibodies), polyclonal antibodies, bispecific antibodies, Fab antibody fragments, F(ab)₂ antibody fragments, Fv antibody fragments (e.g., VH or VL), single chain Fv antibody fragments, dsFv antibody fragments, humanized antibodies, chimeric antibodies or anti-idiotypic antibodies) such as any of those disclosed in any of Burtrum et. al Cancer Research 63:8912-8921(2003); in French Patent Applications FR2834990, FR2834991 and FR2834900 and in PCT Application Publication Nos. WO 03/100008; WO 03/59951; WO 04/71529; WO 03/106621; WO 04/83248; WO 04/87756 and WO 02/53596.

In an embodiment of the invention, an IGF1R inhibitory agent that can be administered to a patient in a method according to the invention is an isolated anti-insulin-like growth factor receptor-1 (IGF1R) antibody comprising a mature or unprocessed 19D12/15H12 Light Chain-C, D, E or F and a mature 19D12/15H12 heavy chain-A or B. In an embodiment of the invention, an IGF1R inhibitory agent that can be administered to a patient in a method according to the invention is an isolated antibody that specifically binds to IGF1R that comprises one or more complementarity determining regions (CDRs) of 19D12/15H12 Light Chain-F and/or 19D12/15H12 heavy chain-A (e.g., all 3 light chain CDRs and all 3 heavy chain CDRs).

The amino acid and nucleotide sequences of the 19D12/15H12 antibody chains are shown below. Dotted, underscored type indicates the signal peptide. Solid underscored type indicates the CDRs. Plain type indicates the framework regions. Mature fragments lack the signal peptide.

```
Modified 19D12/15H12 Light Chain-C (SEQ ID NO: 1)

ATG TCG CCA TCA CAA CTC ATT GGG TTT CTG CTG CTC TGG GTT CCA GCC TCC
AGG GGT GAA ATT GTG CTG ACT CAG AGC CCA GAC TCT CTG TCT GTG ACT CCA
GGC GAG AGA GTC ACC ATC ACC TGC CGG GCC AGT CAG AGC ATT GGT AGT AGC
TTA CAC TGG TAC CAG CAG AAA CCA GGT CAG TCT CCA AAG CTT CTC ATC AAG
TAT GCA TCC CAG TCC CTC TCA GGG GTC CCC TCG AGG TTC AGT GGC AGT GGA
TCT GGG ACA GAT TTC ACC CTC ACC ATC AGT AGC CTC GAG GCT GAA GAT GCT
GCA GCG TAT TAC TGT CAT CAG AGT AGT CGT TTA CCT CAC ACT TTC GGC CAA
GGG ACC AAG GTG GAG ATC AAA CGT ACG
```

```
(SEQ ID NO: 2)

M  S  P  S  Q  L  I  G  F  L  L  L  W  V  P  A  S
R  G  E  I  V  L  T  Q  S  P  D  S  L  S  V  T  P
G  E  R  V  T  I  T  C  R  A  S  Q  S  I  G  S  S
L  H  W  Y  Q  Q  K  P  G  Q  S  P  K  L  L  I  K
Y  A  S  Q  S  L  S  G  V  P  S  R  F  S  G  S  G
S  G  T  D  F  T  L  T  I  S  S  L  E  A  E  D  A
A  A  Y  Y  C  H  Q  S  S  R  L  P  H  T  F  G  Q
G  T  K  V  E  I  K  R  T
```

-continued

Modified 19D12/15H12 Light Chain-D (SEQ ID NO: 3)

ATG TCG CCA TCA CAA CTC ATT GGG TTT CTG CTG CTC TGG GTT CCA GCC TCC
AGG GGT GAA ATT GTG CTG ACT CAG AGC CCA GAC TCT CTG TCT GTG ACT CCA
GGC GAG AGA GTC ACC ATC ACC TGC CGG GCC AGT CAG AGC ATT GGT AGT AGC
TTA CAC TGG TAC CAG CAG AAA CCA GGT CAG TCT CCA AAG CTT CTC ATC AAG
TAT GCA TCC CAG TCC CTC TCA GGG GTC CCC TCG AGG TTC AGT GGC AGT GGA
TCT GGG ACA GAT TTC ACC CTC ACC ATC AGT AGC CTC GAG GCT GAA GAT TTC
GCA GTG TAT TAC TGT CAT CAG AGT AGT CGT TTA CCT CAC ACT TTC GGC CAA
GGG ACC AAG GTG GAG ATC AAA CGT ACG (SEQ ID NO: 4)

M S P S Q L I G F L L L W V P A S
R G E I V L T Q S P D S L S V T P
G E R V T I T C R A S Q S I G S S
L H W Y Q Q K P G Q S P K L L I K
Y A S Q S L S G V P S R F S G S G
S G T D F T L T I S S L E A E D F
A V Y Y C H Q S S R L P H T F G Q
G T K V E I K R T

Modified 19D12/15H12 Light Chain-E (SEQ ID NO: 5)

ATG TCG CCA TCA CAA CTC ATT GGG TTT CTG CTG CTC TGG GTT CCA GCC TCC
AGG GGT GAA ATT GTG CTG ACT CAG AGC CCA GGT ACC CTG TCT GTG ACT CCA
GGC GAG AGA GCC ACC CTC TCC TGC CGG GCC AGT CAG AGC ATT GGT AGT AGC
TTA CAC TGG TAC CAG CAG AAA CCA GGT CAG GCT CCA AGG CTT CTC ATC AAG
TAT GCA TCC CAG TCC CTC TCA GGG ATC CCC GAT AGG TTC AGT GGC AGT GGA
TCT GGG ACA GAT TTC ACC CTC ACC ATC AGT AGA CTG GAG CCT GAA GAT GCT
GCA GCG TAT TAC TGT CAT CAG AGT AGT CGT TTA CCT CAC ACT TTC GGC CAA
GGG ACC AAG GTG GAG ATC AAA CGT ACA (SEQ ID NO: 6)

M S P S Q L I G F L L L W V P A S
R G E I V L T Q S P G T L S V T P
G E R A T L S C R A S Q S I G S S
L H W Y Q Q K P G Q A P R L L I K
Y A S Q S L S G I P D R F S G S G
S G T D F T L T I S R L E P E D A
A A Y Y C H Q S S R L P H T F G Q
G T K V E I K R T

19D12/15H12 Light Chain-F (LCF; SEQ ID NO: 7)

ATG TCG CCA TCA CAA CTC ATT GGG TTT CTG CTG CTC TGG GTT CCA GCC TCC
AGG GGT GAA ATT GTG CTG ACT CAG AGC CCA GGT ACC CTG TCT GTG ACT CCA
GGC GAG AGA GCC ACC CTC TCC TGC CGG GCC AGT CAG AGC ATT GGT AGT AGC
TTA CAC TGG TAC CAG CAG AAA CCA GGT CAG GCT CCA AGG CTT CTC ATC AAG
TAT GCA TCC CAG TCC CTC TCA GGG ATC CCC GAT AGG TTC AGT GGC AGT GGA
TCT GGG ACA GAT TTC ACC CTC ACC ATC AGT AGA CTG GAG CCT GAA GAT TTC
GCA GTG TAT TAC TGT CAT CAG AGT AGT CGT TTA CCT CAC ACT TTC GGC CAA
GGG ACC AAG GTG GAG ATC AAA CGT ACA (SEQ ID NO: 8)

<u>M S P S Q L I G F L L L W V P A S</u>
<u>R G</u> E I V L T Q S P G T L S V T P
G E R A T L S C <u>R A S Q S I G S S</u>
<u>L H</u> W Y Q Q K P G Q A P R L L I K
<u>Y A S Q S L S</u> G I P D R F S G S G
S G T D F T L T I S R L E P E D F
A V Y Y C <u>H Q S S R L P H T</u> F G Q
G T K V E I K R T

19D12/15H12 heavy chain-A (HCA; SEQ ID NO: 9)

<u>ATG GAG TTT GGG CTG AGC TGG GTT TTC CTT GTT GCT ATA TTA AAA GGT GTC</u>
<u>CAG TGT</u> GAG GTT CAG CTG GTG CAG TCT GGG GGA GGC TTG GTA AAG CCT GGG
GGG TCC CTG AGA CTC TCC TGT GCA GCC TCT GGA TTC ACC TTC AGT <u>AGC TTT</u>
<u>GCT ATG CAC</u> TGG GTT CGC CAG GCT CCA GGA AAA GGT CTG GAG TGG ATA TCA
<u>GTT ATT GAT ACT CGT GGT GCC ACA TAC TAT GCA GAC TCC GTG AAG GGC</u> CGA
TTC ACC ATC TCC AGA GAC AAT GCC AAG AAC TCC TTG TAT CTT CAA ATG AAC
AGC CTG AGA GCC GAG GAC ACT GCT GTG TAT TAC TGT GCA AGA <u>CTG GGG AAC</u>
<u>TTC TAC TAC GGT ATG GAC GTC</u> TGG GGC CAA GGG ACC ACG GTC ACC GTC TCC
TCA (SEQ ID NO: 10)

<u>Met Glu Phe Gly Leu Ser Trp Val Phe Leu Val Ala Ile Leu Lys Gly Val</u>
<u>Gln Cys</u> Glu Val Gln Leu Val Gln Ser Gly Gly Gly Leu Val Lys Pro Gly
Gly Ser Leu Arg Leu Ser Cys Ala Ala Ser Gly Phe Thr Phe Ser <u>Ser Phe</u>
<u>Ala Met His</u> Trp Val Arg Gln Ala Pro Gly Lys Gly Leu Glu Trp Ile Ser
<u>Val Ile Asp Thr Arg Gly Ala Thr Tyr Tyr Ala Asp Ser Val Lys Gly</u> Arg
Phe Thr Ile Ser Arg Asp Asn Ala Lys Asn Ser Leu Tyr Leu Gln Met Asn
Ser Leu Arg Ala Glu Asp Thr Ala Val Tyr Tyr Cys Ala Arg <u>Leu Gly Asn</u>
<u>Phe Tyr Tyr Gly Met Asp Val</u> Trp Gly Gln Gly Thr Thr Val Thr Val Ser
Ser

Modified 19D12/15H12 heavy chain-B (SEQ ID NO: 11)

<u>ATG GAG TTT GGG CTG AGC TGG GTT TTC CTT GTT GCT ATA TTA AAA GGT GTC</u>
<u>CAG TGT</u> GAG GTT CAG CTG GTG CAG TCT GGG GGA GGC TTG GTA CAG CCC GGG
GGG TCC CTG AGA CTC TCC TGT GCA GCC TCT GGA TTC ACC TTC AGT <u>AGC TTT</u>
<u>GCT ATG CAC</u> TGG GTT CGC CAG GCT CCA GGA AAA GGT CTG GAG TGG ATA TCA
<u>GTT ATT GAT ACT CGT GGT GCC ACA TAC TAT GCA GAC TCC GTG AAG GGC</u> CGA
TTC ACC ATC TCC AGA GAC AAT GCC AAG AAC TCC TTG TAT CTT CAA ATG AAC
AGC CTG AGA GCC GAG GAC ACT GCT GTG TAT TAC TGT GCA AGA <u>CTG GGG AAC</u>
<u>TTC TAC TAC GGT ATG GAC GTC</u> TGG GGC CAA GGG ACC ACG GTC ACC GTC TCC
TCA (SEQ ID NO: 12)

<u>Met Glu Phe Gly Leu Ser Trp Val Phe Leu Val Ala Ile Leu Lys Gly Val</u>
<u>Gln Cys</u> Glu Val Gln Leu Val Gln Ser Gly Gly Gly Leu Val Gln Pro Gly
Gly Ser Leu Arg Leu Ser Cys Ala Ala Ser Gly Phe Thr Phe Ser <u>Ser Phe</u>
<u>Ala Met His</u> Trp Val Arg Gln Ala Pro Gly Lys Gly Leu Glu Trp Ile Ser
<u>Val Ile Asp Thr Arg Gly Ala Thr Tyr Tyr Ala Asp Ser Val Lys Gly</u> Arg
Phe Thr Ile Ser Arg Asp Asn Ala Lys Asn Ser Leu Tyr Leu Gln Met Asn
Ser Leu Arg Ala Glu Asp Thr Ala Val Tyr Tyr Cys Ala Arg <u>Leu Gly Asn</u>
<u>Phe Tyr Tyr Gly Met Asp Val</u> Trp Gly Gln Gly Thr Thr Val Thr Val Ser
Ser

Plasmids comprising a CMV promoter operably linked to the 15H12/19D12 LCC, LCD, LCE, LCF or to the 15H12/19D12 HCA or HCB have been deposited at the American Type Culture Collection (ATCC); 10801 University Boulevard; Manassas, Va. 20110-2209 on May 21, 2003. The deposit names and the ATCC accession numbers for the plasmids are set forth below:

(1) CMV promoter-15H12/19D12 HCA (γ4)—
    Deposit name: "15H12/19D12 HCA (γ4)"
    ATCC accession No.: PTA-5214

(2) CMV promoter-15H12/19D12 HCB (γ4)—
    Deposit name: "15H12/19D12 HCB (γ4)"
    ATCC accession No.: PTA-5215

(3) CMV promoter-15H12/19D12 HCA (γ1)—
    Deposit name: "15H12/19D12 HCA (γ1)";
    ATCC accession No.: PTA-5216

(4) CMV promoter-15H12/19D12 LCC (κ)—
    Deposit name: "15H12/19D12 LCC (κ)";
    ATCC accession No.: PTA-5217

(5) CMV promoter-15H12/19D12 LCD (κ)—
    Deposit name: "15H12/19D12 LCD (κ)";
    ATCC accession No.: PTA-5218

(6) CMV promoter-15H12/19D12 LCE (κ)—
    Deposit name: "15H12/19D12 LCE (κ)";
    ATCC accession No.: PTA-5219

(7) CMV promoter-15H12/19D12 LCF (κ)—
    Deposit name: "15H12/19D12 LCF (κ)";
    ATCC accession No.: PTA-5220

All restrictions on access to the plasmids deposited in ATCC will be removed upon grant of a patent. In an embodiment of the present invention, an anti-IGF1R antibody or antigen-binding fragment thereof of the invention comprises any of the CDRs or Ig heavy or light chains or variable regions thereof in any of PTA-5214-PTA-5220. In an embodiment of the invention, the antibody comprises a light chain encoded by the plasmid deposited under number PTA-5220 and a heavy chain encoded by the plasmid deposited under number PTA-5214 or PTA-5216.

In an embodiment, an antibody that binds "specifically" to human IGF1R binds with Kd of about $1.28 \times 10^{-10}$ M or less by Biacore measurement or with a Kd of about $2.05 \times 10^{-12}$ or less by KinExA measurement.

In an embodiment of the invention, an IGF1R inhibitory agent that can be administered to a patient in a method according to the invention comprises any light chain immunoglobulin and/or a heavy chain immunoglobulin as set forth in Published International Application No. WO 2002/53596 which is herein incorporated by reference in its entirety. For example, in an embodiment, the antibody comprises a light chain variable region comprising an amino acid sequence selected from the group consisting of SEQ ID NOs: 2, 6, 10, 14, 18, 22, 47 and 51 as set forth in WO 2002/53596 and/or a heavy chain variable region comprising an amino acid sequence selected from the group consisting of SEQ ID NOs: 4, 8, 12, 16, 20, 24, 45 and 49 as set forth in WO 2002/53596.

In an embodiment of the invention, an IGF1R inhibitory agent that can be administered to a patient in a method according to the invention comprises any light chain immunoglobulin and/or a heavy chain immunoglobulin as set forth in Published International Application No. WO 2003/59951 which is herein incorporated by reference in its entirety. For example, in an embodiment, the antibody comprises a light chain variable region comprising an amino acid sequence selected from the group consisting of SEQ ID NOs: 54, 61 and 65 as set forth in WO 2003/59951 and/or a heavy chain variable region comprising an amino acid sequence selected from the group consisting of SEQ ID NOs: 69, 75, 79 and 83 as set forth in WO 2003/59951.

In an embodiment of the invention, an IGF1R inhibitory agent that can be administered to a patient in a method according to the invention comprises any light chain immunoglobulin and/or a heavy chain immunoglobulin as set forth in Published International Application No. WO 2004/83248 which is herein incorporated by reference in its entirety. For example, in an embodiment, the antibody comprises a light chain variable region comprising an amino acid sequence selected from the group consisting of SEQ ID NOs: 109, 111, 113, 115, 117, 119, 121, 123, 125, 127, 129, 131, 133, 135, 137, 139, 141 and 143 as set forth in WO 2004/83248 and/or a heavy chain variable region comprising an amino acid sequence selected from the group consisting of SEQ ID NOs: 108, 110, 112, 114, 116, 118, 120, 122, 124, 126, 128, 130, 132, 134, 136, 138, 140 and 142 as set forth in WO 2004/83248.

In an embodiment of the invention, an IGF1R inhibitory agent that can be administered to a patient in a method according to the invention comprises any light chain immunoglobulin and/or a heavy chain immunoglobulin as set forth in Published International Application No. WO 2003/106621 which is herein incorporated by reference in its entirety. For example, in an embodiment, the antibody comprises a light chain variable region comprising an amino acid sequence selected from the group consisting of SEQ ID NOs: 8-12, 58-69, 82-86, 90, 94, 96, 98, as set forth in WO 2003/106621 and/or a heavy chain variable region comprising an amino acid sequence selected from the group consisting of SEQ ID NOs: 7, 13, 70-81, 87, 88, 92 as set forth in WO 2003/106621.

In an embodiment of the invention, an IGF1R inhibitory agent that can be administered to a patient in a method according to the invention comprises any light chain immunoglobulin and/or a heavy chain immunoglobulin as set forth in Published International Application No. WO 2004/87756 which is herein incorporated by reference in its entirety. For example, in an embodiment, the antibody comprises a light chain variable region comprising an amino acid sequence of SEQ ID NO: 2 as set forth in WO 2004/87756 and/or a heavy chain variable region comprising an amino acid sequence of SEQ ID NO: 1 as set forth in WO 2004/87756.

Furthermore, the scope of the present invention comprises any antibody or antibody fragment comprising one or more CDRs and/or framework regions of any of the light chain immunoglobulin or heavy chain immunoglobulins set forth in WO 2002/53596; WO 2003/59951; WO 2004/83248; WO 2003/106621 or WO 2004/87756 as identified by any of the methods set forth in Chothia et al., J. Mol. Biol. 186:651-663 (1985); Novotny and Haber, Proc. Natl. Acad. Sci. USA 82:4592-4596 (1985) or Kabat, E. A. et al., *Sequences of Proteins of Immunological Interest*, National Institutes of Health, Bethesda, Md., (1987)).

In an embodiment of the invention, anti-IGF1R antibody is produced by a hybridoma that is deposited at the American Type Culture Collection under deposit no. PTA-2792, PTA-2788, PTA-2790, PTA-2791, PTA-2789 or PTA-2793.

In an embodiment of the invention, an anti-IGF1R antibody of the invention comprises an immunoglobulin heavy chain variable region comprising an amino acid sequence selected from the group consisting of:

```
                                          (SEQ ID NO: 13)
  1 grlgqawrsl rlscaasgft fsdyymswir qapgkglewv syisssgstr
 51 dyadsvkgrf tisrdnakns lylqmnslra edtavyycvr dgvettfyyy
101 yygmdvwgqg ttvtvssast kgpsvfplap csrstsesta algclvkdyf
151 pepvtvswns galtsgvhtf psca (SEQ ID NO: 14)
  1 vqllesgggl vqpggslrls ctasgftfss yamnwvrqap gkglewvsai
 51 sgsggttfya dsvkgrftis rdnsrttlyl qmnslraedt avyycakdlg
101 wsdsyyyyyg mdvwgqgttv tvss (SEQ ID NO: 15)
  1 gpglvkpset lsltctvsgg sisnyywswi rqpagkglew igriytsgsp
 51 nynpslksrv tmsvdtsknq fslklnsvta adtavyycav tifgvviifd
101 ywgqgtlvtv ss (SEQ ID NO: 16)
  1 evqllesggg lvqpggslrl scaasgftfs syamswvrqa pgkglewvsa
 51 isgsggityy adsvkgrfti srdnskntly lqmnslraed tavyycakdl
101 gygdfyyyyy gmdvwgqgtt vtvss (SEQ ID NO: 17)
  1 pglvkpsetl sltctvsggs issyywswir qppgkglewi gyiyysgstn
 51 ynpslksrvt isvdtsknqf slklssvtaa dtavyycart ysssfyyygm
101 dvwgqgttvt vss (SEQ ID NO: 18)
  1 evqllesggg lvqpggslrl scaasgftfs syamswvrqa pgkglewvsg
 51 itgsggstyy adsvkgrfti srdnskntly lqmnslraed tavyycakdp
101 gttvimswfd pwgqgtlvtv ss
```

In an embodiment of the invention, an anti-IGF1R antibody of the invention comprises an immunoglobulin light chain variable region comprising an amino acid sequence selected from the group consisting of:

In an embodiment of the invention, the anti-IGF1R antibody comprises a light chain immunoglobulin, or a mature fragment thereof (i.e., lacking signal sequence), or variable region thereof, comprising the amino acid sequence of:

```
                                          (SEQ ID NO: 19)
  1 asvgdrvtft crasqdirrd lgwyqqkpgk apkrliyaas rlqsgvpsrf
 51 sgsgsgteft ltisslqped fatyyclqhn nyprtfgqgt eveiirtvaa
101 psvfifppsd eqlksgtasv vcllnnfypr eakvqw (SEQ ID NO: 20)
  1 diqmtqfpss lsasvgdrvt itcrasqgir ndlgwyqqkp gkapkrliya
 51 asrlhrgvps rfsgsgsgte ftltisslqp edfatyyclq hnsypcsfgq
101 gtkleik (SEQ ID NO: 21)
  1 sslsasvgdr vtftcrasqd irrdlgwyqq kpgkapkrli yaasrlqsgv
 51 psrfsgsgsg teftltissl qpedfatyyc lqhnnyprtf gqgteveiir (SEQ ID NO: 22)
  1 diqmtqspss lsasvgdrvt itcrasqgir sdlgwfqqkp gkapkrliya
 51 asklhrgvps rfsgsgsgte ftltisrlqp edfatyyclq hnsypltfgg
101 gtkveik (SEQ ID NO: 23)
  1 gdrvtitcra sqsistflnw yqqkpgkapk llihvasslq ggvpsrfsgs
 51 gsgtdftlti sslqpedfat yycqqsynap ltfgggtkve ik (SEQ ID NO: 24)
  1 ratlscrasq svrgrylawy qqkpgqaprl liygassrat gipdrfsgsg
 51 sgtdftltis rlepedfavf ycqqygsspr tfgqgtkvei k
```

(SEQ ID NO: 25)
```
  1 mdmrvpaqll glllwfpga rcdiqmtqsp sslsasvgdr vtitcrasqq
 51 irndlqwyqq kpgkapkrli yaasslqsqv psrfsqsgsq teftltissl
101 qpedfatyyc lqhnsypwtf gggtkveikr tvaapsvfif ppsdeqlksg
151 tasvvcllnn fypreakvqw kvdnalqsgn sqesvteqds kdstyslsst
201 ltlskadyek hkvyacevth qglsspvtks fnrgec;
```

(SEQ ID NO: 26)
```
  1 mdmrvpaqll glllwfpga rcdiqmtqsp sslsasvgdr vtftcrasqd
 51 irrdlqwyqq kpgkapkrli yaasrlqsqv psrfsqsgsq teftltissl
101 qpedfatyyc lqhnnyprtf gggteveiir tvaapsvfif ppsdeqlksg
151 tasvvcllnn fypreakvqw kvdnalqsgn sqesvteqds kdstyslsst
201 ltlskadyek hkvyacevth qglsspvtks fnrgec;
```

(SEQ ID NO: 27)
```
  1 mdmrvpaqll glllwfpga rcdiqmtqsp sslsasvgdr vtitcrasqq
 51 irndlqwyqq kpgkapkrli yaasslqsqv psrfsqsgsq teftltissl
101 qpedfatyyc lqhnsypytf gggtkleikr tvaapsvfif ppsdeqlksg
151 tasvvcllnn fypreakvqw kvdnalqsgn sqesvteqds kdstyslsst
201 ltlskadyek hkvyacevth qglsspvtks fnrgec;
or
```

(SEQ ID NO: 28)
```
  1 mdmrvpaqll glllwfpga rcdiqmtqfp sslsasvgdr vtitcrasqq
 51 irndlqwyqq kpgkapkrli yaasrlhrqv psrfsqsgsq teftltissl
101 qpedfatyyc lqhnsypcsf gggtkleikr tvaapsvfif ppsdeqlksg
151 tasvvcllnn fypreakvqw kvdnalqsgn sqesvteqds kdstyslsst
201 ltlskadyek hkvyacevth qglsspvtks fnrgec.
```

In an embodiment of the invention, the signal sequence is amino acids 1-22 of SEQ ID NOs: 25-28. In an embodiment of the invention, the mature variable region is underscored.

In an embodiment of the invention, the anti-IGF1R antibody comprises a heavy chain immunoglobulin or a mature fragment thereof (i.e., lacking signal sequence), or a variable region thereof, comprising the amino acid sequence of:

(SEQ ID NO: 29)
```
  1 mefglswvfl vaiikgvqcq vqlvesgggl vkpggslrls caasgftfsd
 51 yymswirqap gkglewvsyi sssgstiyya dsvkgrftis rdnaknslyl
101 qmnslraedt avyycarvlr flewllyyyy yyqmdvwgqg ttvtvssast
151 kgpsvfplap csrstsesta algclvkdyf pepvtvswns galtsgvhtf
201 pavlqssgly slssvvtvps snfgtqtytc nvdhkpsntk vdktverkcc
251 vecppcpapp vagpsvflfp pkpkdtlmis rtpevtcvvv dvshedpevq
301 fnwyvdgvev hnaktkpree qfnstfrvvs vltvvhqdwl ngkeykckvs
351 nkglpapiek tisktkgqpr epqvytlpps reemtknqvs ltclvkgfyp
401 sdiavewesn gqpennyktt ppmldsdgsf flyskltvdk srwqqgnvfs
451 csvmhealhn hytqkslsls pgk;
```

(SEQ ID NO: 30)
```
  1 mefglswvfl vaiikgvqcq aqlvesgggl vkpggslrls caasgftfsd
 51 yymswirqap gkglewvsyi sssgstrdya dsvkgrftis rdnaknslyl
101 qmnslraedt avyycvrdgv ettfyyyyg mdvwgqgttv tvssastkgp
151 svfplapcsr stsestaalg clvkdyfpep vtvswnsgal tsgvhtfpav
201 lqssglysls svvtvpssnf gtqtytcnvd hkpsntkvdk tverkccvec
251 ppcpappvag psvflfppkp kdtlmisrtp evtcvvvdvs hedpevqfnw
301 yvdgvevhna ktkpreeqfn stfrvvsvlt vvhqdwlngk eykcvsnkg
351 lpapiektis ktkgqprepq vytlppsree mtknqvsltc lvkgfypsdi
401 avewesngqp ennykttppm ldsdgsffly skltvdksrw qqgnvfscsv
451 mhealhnhyt qkslslspgk;
```

(SEQ ID NO: 31)
```
  1 mefglswlfl vailkgvqce vqllesgggl vqpggslrls caasgftfss
 51 yamswvrqap gkglewvsai sqsqgstyya dsvkgrftis rdnskntlyl
101 qmnslraedt avyycakgys sgwyyyyyg mdvwgqgttv tvssastkgp
151 svfplapcsr stsestaalg clvkdyfpep vtvswnsgal tsgvhtfpav
201 lqssglysls svvtvpssnf gtqtytcnvd hkpsntkvdk tverkccvec
251 ppcpappvag psvflfppkp kdtlmisrtp evtcvvvdvs hedpevqfnw
301 yvdgvevhna ktkpreeqfn stfrvvsvlt vvhqdwlngk eykcvsnkg
351 lpapiektis ktkgqprepq vytlppsree mtknqvsltc lvkgfypsdi
401 avewesngqp ennykttppm ldsdgsffly skltvdksrw qqgnvfscsv
451 mhealhnhyt qkslslspgk;
or
```

-continued (SEQ ID NO: 32)

```
  1 mefglswlfl vailkgvqce vqllesqggl vqpqgslrls ctasgftfss
 51 yamnwvrqap gkglewvsai sqsqgttfya dsvkgrftis rdnsrttlyl
101 qmnslraedt avyycakdlq wsdsyyyyyg mdvwgqgttv tvssastkgp
151 svfplapcsr stsestaalg clvkdyfpep vtvswnsgal tsgvhtfpav
201 lqssglysls svvtvpssnf gtqtytcnvd hkpsntkvdk tverkccvec
251 ppcpappvag psvflfppkp kdtlmisrtp evtcvvvdvs hedpevqfnw
301 yvdgvevhna ktkpreeqfn stfrvvsvlt vvhqdwlngk eykckvsnkg
351 lpapiektis ktkgqprepq vytlppsree mtknqvsltc lvkgfypsdi
401 avewesngqp ennykttppm ldsdgsffly skltvdksrw qqgnvfscsv
451 mhealhnhyt qkslslspgk.
```

In an embodiment of the invention, the signal sequence is amino acids 1-19 of SEQ ID NOs: 29-32. In an embodiment of the invention, the mature variable region is underscored.

In an embodiment of the invention, the anti-IGF1R antibody comprises a light chain variable region comprising the amino acid sequence of any of SEQ ID NOs: 19-24 paired with a heavy chain variable region comprising an amino acid sequence of any of SEQ ID NOs: 13-18, respectively. In an embodiment of the invention, the anti-IGF1R antibody comprises a mature light chain variable region comprising an amino acid sequence of any of SEQ ID NOs: 25 or 26 paired with a heavy chain variable region comprising an amino acid sequence of any of SEQ ID NOs: 29 or 30. In an embodiment of the invention, the anti-IGF1R antibody comprises a mature light chain variable region comprising an amino acid sequence of any of SEQ ID NOs: 27 or 28 paired with a heavy chain variable region comprising an amino acid sequence of any of SEQ ID NOs: 31 or 32.

In an embodiment of the invention, an anti-IGF1R antibody of the invention comprises an immunoglobulin heavy chain or mature fragment or variable region of 2.12.1 fx (SEQ ID NO: 33) (in an embodiment of the invention, the leader sequence is underscored):

```
  1 mefglswvfl vaiikgvqcq vqlvesgggl vkpggslrls caasgftfsd
 51 yymswirqap gkglewvsyi sssgstrdya dsvkgrftis rdnaknslyl
101 qmnslraedt avyycardgv ettfyyyyyg mdvwgqgttv tvssastkgp
151 svfplapcsr stsestaalg clvkdyfpep vtvswnsgal tsgvhtfpav
201 lqssglysls svvtvpssnf gtqtytcnvd hkpsntkvdk tverkccvec
251 ppcpappvag psvflfppkp kdtlmisrtp evtcvvvdvs hedpevqfnw
301 yvdgvevhna ktkpreeqfn stfrvvsvlt vvhqdwlngk eykckvsnkg
351 lpapiektis ktkgqprepq vytlppsree mtknqvsltc lvkgfypsdi
401 avewesngqp ennykttppm ldsdgsffly skltvdksrw qqgnvfscsv
451 mhealhnhyt qkslslspgk
```

In an embodiment of the invention, an anti-IGF1R antibody of the invention comprises mature immunoglobulin heavy chain variable region 2.12.1 fx (amino acids 20-144 or SEQ ID NO: 33; SEQ ID NO: 34):

q vqlvesgggl vkpggslrls caasgftfsd yymswirqap gkglewvsyi sssgstrdya dsvkgrftis rdnaknslyl qmnslraedt avyycardgv ettfyyyyg mdvwgqgttv tvss In an embodiment of the invention, an anti-IGF1R antibody of the invention comprises an immunoglobulin light chain or mature fragment or variable region 2.12.1 fx (SEQ ID NO: 35) (in an embodiment of the invention, the leader sequence is underscored):

```
  1 mdmrvpaqll qllllwfpga rcdiqmtqsp sslsasvgdr vtitcrasqd 51 irrdlgwyqq kpgkapkrli yaasrlqsgv psrfsgsgsg teftltissl 101 qpedfatyyc lqhnnyprtf gqgtkveikr tvaapsvfif ppsdeqlksg 151 tasvvcllnn fypreakvqw kvdnalqsgn sqesvteqds kdstyslsst 201 ltlskadyek hkvyacevth qglsspvtks fnrgec
```

In an embodiment of the invention, an anti-IGF1R antibody of the invention comprises mature immunoglobulin light chain variable region 2.12.1 fx (amino acids 23-130 of SEQ ID NO: 35; SEQ ID NO: 36):

diqmtqsp sslsasvgdr vtitcrasqd irrdlgwyqq kpgkapkrli yaasrlqsgv psrfsgsgsg teftltissl qpedfatyyc lqhnnyprtf gqgtkveikr In an embodiment of the invention, an anti-IGF1R antibody of the invention comprises a humanized 7C10 immunoglobulin light chain variable region; version 1 (SEQ ID NO: 37):

```
  1 dvvmtqspls lpvtpgepas iscrssqsiv hsngntylqw ylqkpgqspq 51 lliykvsnrl ygvpdrfsgs gsgtdftlki srveaedvgv yycfqgshvp 101 wtfgqgtkve ik
```

In an embodiment of the invention, an anti-IGF1R antibody of the invention comprises humanized 7C10 immunoglobulin light chain variable region; version 2 (SEQ ID NO: 38):

```
  1 divmtqspls lpvtpgepas iscrssqsiv hsngntylqw ylqkpgqspq 51 lliykvsnrl ygvpdrfsgs gsgtdftlki srveaedvgv yycfqgshvp 101 wtfgqgtkve ik
```

In an embodiment of the invention, an anti-IGF1R antibody of the invention comprises a humanized 7C10 immunoglobulin heavy chain variable region; version 1 (SEQ ID NO: 39):

```
  1 qvqlqesgpg lvkpsetlsl tctvsgysit ggylwnwirq ppgkglewmg
 51 yisydgtnny kpslkdriti srdtsknqfs lklssvtaad tavyycaryg
101 rvffdywgqg tlvtvss
```

In an embodiment of the invention, an anti-IGF1R antibody of the invention comprises the humanized 7C10 immunoglobulin heavy chain variable region; version 2 (SEQ ID NO: 40):

```
  1 qvqlqesgpg lvkpsetlsl tctvsgysit ggylwnwirq ppgkglewig
 51 yisydgtnny kpslkdrvti srdtsknqfs lklssvtaad tavyycaryg
101 rvffdywgqg tlvtvss
```

In an embodiment of the invention, an anti-IGF1R antibody of the invention comprises the humanized 7C10 immunoglobulin heavy chain variable region; version 3 (SEQ ID NO: 41):

```
  1 qvqlqesgpg lvkpsetlsl tctvsgysis ggylwnwirq ppgkglewig
 51 yisydgtnny kpslkdrvti svdtsknqfs lklssvtaad tavyycaryg
101 rvffdywgqg tlvtvss
```

In an embodiment of the invention, an anti-IGF1R antibody of the invention comprises A12 immunoglobulin heavy chain variable region (SEQ ID NO: 42):

```
  1 evqlvqsgae vkkpgssvkv sckasggtfs syaiswvrqa pgqglewmgg
 51 iipifgtany aqkfqgrvti tadkststay melsslrsed tavyycarap
101 lrflewstqd hyyyyymdvw gkgttvtvss
```

In an embodiment of the invention, an anti-IGF1R antibody of the invention comprises A12 immunoglobulin light chain variable region (SEQ ID NO: 43):

```
  1 sseltqdpav svalgqtvri tcqgdslrsy yaswyqqkpg qapvlviygk
 51 nnrpsgipdr fsgsssgnta sltitgaqae deadyycnsr dnsdnrlifg
101 ggtkltvls
``` or (SEQ ID NO: 105):

```
  1 sseltqdpav svalgqtvri tcqgdslrsy yatwyqqkpg qapilviyge
 51 nkrpsgipdr fsgsssgnta sltitgaqae deadyycksr dgsgqhlvfg
101 ggtkltvlg
```

In an embodiment of the invention, an anti-IGF1R antibody of the invention comprises 1A immunoglobulin heavy chain variable region (SEQ ID NO: 44):

```
  1 evqlvqsggg lvhpggslrl scagsgftfr nyamywvrqa pgkglewvsa
 51 igsgggtyya dsvkgrftis rdnaknslyl qmnslraedm avyycarapn
101 wgsdafdiwg qgtmvtvss;
``` optionally including one or more of the following mutations: R30, S30, N31, S31, Y94, H94, D104, E104.

In an embodiment of the invention, an anti-IGF1R antibody of the invention comprises 1A immunoglobulin light chain variable region (SEQ ID NO: 45):

```
  1 diqmtqspss lsasvgdrvt itcrasqgis swlawyqqkp ekapksliya
 51 asslqsgvps rfsgsgsgtd ftltisslqp edfatyycqq ynsypptfgp
101 gtkvdik;
``` optionally including one or more of the following mutations: P96, I96, P100, Q100, R103, K103, V104, L104, D105, E105

In an embodiment of the invention, an anti-IGF1R antibody of the invention comprises single chain antibody (fv) 8A1 (SEQ ID NO: 46):

```
  1 evqlvqsgae vkkpgeslti sckgpgynff nywigwvrqm pgkglewmgi
 51 iyptdsdtry spsfqgqvti svdksistay lqwsslkasd tamyycarsi
101 rycpggrcys gyygmdvwgq gtmvtvssgg ggsggggsgg ggsseltqdp
151 avsvalgqtv ritcqgdslr syyaswyqqk pgqapvlviy gknnrpsgip
201 drfsgsssgn tasltitgaq aedeadyycn srdssgnhvv fgggtkltvl
251 g
```

In an embodiment of the invention, an anti-IGF1R antibody of the invention comprises single chain antibody (fv) 9A2 (SEQ ID NO: 47):

```
  1 qvqlvqsgae vrkpgasvkv scktsgytfr nydinwvrqa pgqglewmgr
 51 isghygntdh aqkfqgrftm tkdtststay melrsltfdd tavyycarsq
101 wnvdywgrgt lvtvssgggg sggggsgggg salnfmltqp hsvsespgkt
151 vtisctrssg siasnyvqwy qqrpgsspt vifednrrps gvpdrfsgsi
201 dtssnsaslt isglktedea dyycqsfdst nlvvfgggtk vtvlg
```

In an embodiment of the invention, an anti-IGF1R antibody of the invention comprises single chain antibody (fv) 11A4 (SEQ ID NO: 48):

```
  1 evqllesggg lvqpggslrl scaasgftfs syamswvrqa pgkglewvsa
 51 isgsggstyy adsvkgrfti srdnskntly lqmnslraed tavyycassp
101 yssrwysfdp wgqgtmvtvs sggggsgggg sggggsalsy eltqppsvsv
151 spgqtatitc sgddlgnkyv swyqqkpgqs pvlviyqdtk rpsgiperfs
201 gsnsgniatl tisgtqavde adyycqvwdt gtvvfgggtk ltvlg
```

In an embodiment of the invention, an anti-IGF1R antibody of the invention comprises single chain antibody (fv) 7A4 (SEQ ID NO: 49):

```
  1 evqlvqsgae vkkpgeslti sckgsgynff nywigwvrqm pgkdlewmgi 51 iyptdsdtry spsfqgqvti svdksistay lqwsslkasd tamyycarsi 101 rycpggrcys gyygmdvwgq gtmvtvssgg gssggggsgg ggsseltqdp 151 avsvalgqtv ritcrgdslr nyyaswyqqk pgqapvlviy gknnrpsgip 201 drfsgsssgn tasltitgaq aedeadyycn srdssgnhmv fgggtkltvl 251 g
```

In an embodiment of the invention, an anti-IGF1R antibody of the invention comprises single chain antibody (fv) 11A1 (SEQ ID NO: 50):

```
  1 evqlvesggg vvqpgrslrl scaasgftfs dfamhwvrqi pgkglewlsg 51 lrhdgstayy agsvkgrfti srdnsrntvy lqmnslraed tatyycvtgs 101 gssgphafpv wgkgtlvtvs sggggsgggg sggggsalsy vltqppsasg 151 tpgqrvtisc sgsnsnigty tvnwfqqlpg tapklliysn nqrpsgvpdr 201 fsgsksgtsa slaisglqse deadyycaaw ddslngpvfg ggtkvtvlg
```

In an embodiment of the invention, an anti-IGF1R antibody of the invention comprises single chain antibody (fv) 7A6 (SEQ ID NO: 51)

```
  1 evqlvqsgae vkkpgeslti sckgsgynff nywigwvrqm pgkglewmgi 51 iyptdsdtry spsfqgqvti svdksistay lqwsslkasd tamyycarsi 101 rycpggrcys gyygmdvwgq gtlvtvssgg ggsggggsgg ggsseltqdp 151 avsvalgqtv ritcqgdslr syytnwfqqk pgqapllvvy aknkrpsgip 201 drfsgsssgn tasltitgaq aedeadyycn srdssgnhvv fgggtkltvl 251 g
```

In an embodiment of the invention, an anti-IGF1R antibody or an antigen-binding fragment thereof (e.g., a heavy chain or light chain immunoglobulin) of the invention comprises one or more complementarity determining regions (CDR) selected from the group consisting of:

| | |
|---|---|
| sywmh; | (SEQ ID NO: 52) |
| einpsngrtnynekfkr; | (SEQ ID NO: 53) |
| grpdyygsskwyfdv; | (SEQ ID NO: 54) |
| rssqsivhsnvntyle; | (SEQ ID NO: 55) |
| kvsnrfs; | (SEQ ID NO: 56) |
| and | |
| fqgshvppt. | (SEQ ID NO: 57) |

In an embodiment of the invention, an anti-IGF1R antibody or an antigen-binding fragment thereof of the invention comprises a heavy chain immunoglobulin variable region selected from the group consisting of:

```
                                                    (SEQ ID NO: 58)
  1 qvqlvqsgae vvkpgasvkl sckasgytft sywmhwvkqr pgqglewige
 51 inpsngrtny nqkfqgkatl tvdkssstay mqlssltsed savyyfargr
101 pdyygsskwy fdvwgqgttv tvs;

(SEQ ID NO: 59)
  1 qvqfqqsgae lvkpgasvkl sckasgytft sylmhwikqr pgrglewigr
 51 idpnnvvtkf nekfkskatl tvdkpsstay melssltsed savyycarya
101 ycrpmdywgq gttvtvss;

(SEQ ID NO: 60)
  1 qvqlqqsgae lvkpgasvkl sckasgytft sywmhwvkqr pgqglewige
 51 inpsngrtny nekfkrkatl tvdksssktay mqlssltsed savyyfargr
101 pdyygsskwy fdvwgagttv tvs;

(SEQ ID NO: 61)
  1 qvqlqqsgae lmkpgasvki sckatgytfs sfwiewvkqr pghglewige
 51 ilpgsggthy nekfkgkatf tadkssntay mqlssltsed savyycargh
101 syyfydgdyw gqgtsvtvss;

(SEQ ID NO: 62)
  1 qvqlqqpgsv lvrpgasvkl sckasgytft sswihwakqr pgqglewige
 51 ihpnsgntny nekfkgkatl tvdtssstay vdlssltsed savyycarwr
101 ygspyyfdyw gqgttltvss;

(SEQ ID NO: 63)
  1 qvqlqqpgae lvkpgasvkl sckasgytft sywmhwvkqr pgrglewigr
 51 idpnsggtky nekfkskatl tvdkpsstay mqlssltsed savyycaryd
101 yygssyfdyw gqgttltvss;

(SEQ ID NO: 64)
  1 qvqlvqsgae vvkpgasvkl sckasgytft sywmhwvkqr pgqglewige
 51 inpsngrtny nqkfqgkatl tvdkssstay mqlssltsed savyyfargr
101 pdyygsskwy fdvwgqgttv tvs;

(SEQ ID NO: 65)
  1 qvqlqqsgae lvkpgasvkl sckasgytft sywmhwvkqr pgqglewige
 51 inpsngrtny nekfkrkatl tvdkssstay mqlssltsed savyyfargr
101 pdyygsskwy fdvwgagttv tvss;

(SEQ ID NO: 66)
  1 qvqlvqsgae vvkpgasvkl sckasgytft sywmhwvkqr pgqglewige
 51 inpsngrtny nqkfqgkatl tvdkssstay mqlssltsed savyyfargr
101 pdyygsskwy fdvwgqgttv tvss;

(SEQ ID NO: 67)
  1 qvqlqqsgae lvkpgasvkl sckasgytft sywmhwvkqr pgrglewigr
 51 idpnsggtky nekfkskatl tvdkpsstay mqlssltsed savyycaryd
101 yygssyfdyw gqgttvtvss;

(SEQ ID NO: 68)
  1 qiqlqqsgpe lvrpgasvki sckasgytft dyyihwvkqr pgeglewigw
 51 iypgsgntky nekfkgkatl tvdtssstay mqlssltsed savyfcargg
101 kfamdywgqg tsvtvss;

(SEQ ID NO: 69)
  1 qvqlqqsgae lvkpgasvkl sckasgytft sywmhwvkqr pgqglewige
 51 inpsngrtny nekfkrkatl tvdkssstay mqlssltsed savyyfargr
101 pdyygsskwy fdvwgagttv tvs;

(SEQ ID NO: 70)
  1 qiqlqqsgpe lvkpgasvki sckasgytft dyyinwmkqk pgqglewigw
 51 idpgsgntky nekfkgkatl tvdtssstay mqlssltsed tavyfcarek
101 ttyyyamdyw gqgtsvtvsa;

(SEQ ID NO: 71)
  1 vqlqqsgael mkpgasvkis ckasgytfsd ywiewvkqrp ghglewigei
 51 lpgsgstnyh erfkgkatft adtssstaym qlnsltseds gvyyclhgny
101 dfdgwgqgtt ltvss;
and
                                                    (SEQ ID NO: 72)
  1 qvqllesgae lmkpgasvki sckatgytfs sfwiewvkqr pghglewige
 51 ilpgsggthy nekfkgkatf tadkssntay mqlssltsed savyycargh
101 syyfydgdyw gqgtsvtvss;
``` and/or a light chain immunoglobulin variable region selected from the group consisting of:

```
                                              (SEQ ID NO: 73)
  1 dvlmtqipvs lpvslgdqas iscrssqiiv hnngntylew ylqkpgqspq
 51 lliykvsnrf sgvpdrfsgs gsgtdftlki srveaedlgv yycfqgshvp
101 ftfgsgtkle ikr;

(SEQ ID NO: 74)
  1 dvlmtqtpls lpvslgdpas iscrssqsiv hsnvntylew ylqkpgqspk
 51 lliykvsnrf sgvpdrfsgs gagtdftlri srveaedlgi yycfqgshvp
101 ptfgggtkle ikr;

(SEQ ID NO: 75)
  1 dvlmtqtpls lpvslgdpas iscrssqsiv hsnvntylew ylqkpgqspr
 51 lliykvsnrf sgvpdrfsgs gagtdftlri srveaedlgi yycfqgshvp
101 ptfgggtkle ikr;

(SEQ ID NO: 76)
  1 dvlmtqtpls lpvslgdpas iscrssqsiv hsnvntylew ylqkpgqspk
 51 lliykvsnrf sgvpdrfsgs gagtdftlri srveaedlgi yycfqgshvp
101 ptfgggtkle ikr;

(SEQ ID NO: 77)
  1 dvlmtqtpls lpvslgdpas iscrssqsiv hsnvntylew ylqkpgqspr
 51 lliykvsnrf sgvpdrfsgs gagtdftlri srveaedlgi yycfqgshvp
101 ptfgggtkle ikr;

(SEQ ID NO: 78)
  1 dvlmtqtpls lpvslgdqas iscrssqxiv hsngntylew ylqkpgqspk
 51 lliykvsnrf sgvpdrfsgs gsgtdftlki srveaedlgv yycfqgshvp
101 xtfgggtkle ikr;

(SEQ ID NO: 79)
  1 dvvmtqtpls lpvslgdpas iscrssqsiv hsnvntylew ylqkpgqspk
 51 lliykvsnrf sgvpdrfsgs gagtdftlri srveaedlgi yycfqgshvp
101 ptfgggtkle ikr;

(SEQ ID NO: 80)
  1 dvvmtqtpls lpvslgdpas iscrssqsiv hsnvntylew ylqkpgqspr
 51 lliykvsnrf sgvpdrfsgs gagtdftlri srveaedlgi yycfqgshvp
101 ptfgggtkle ikr;

(SEQ ID NO: 81)
  1 dvlmtqtpls lpvslgdpas iscrssqsiv hsnvntylew ylqkpgqspr
 51 lliykvsnrf sgvpdrfsgs gagtdftlri srveaedlgi yycfqgshvp
101 ptfgggtkle ikr;

(SEQ ID NO: 82)
  1 dvlmtqipvs lpvslgdqas iscrssqiiv hnngntylew ylqkpgqspq
 51 lliykvsnrf sgvpdrfsgs gsgtdftlki srveaedlgv yycfqgshvp
101 ftfgsgtkle ikr;

(SEQ ID NO: 83)
  1 dvlmtqtpls lpvslgdqas iscrfsqsiv hsngntylew ylqksgqspk
 51 lliykvsnrf sgvpdrfsgs gsgtdftlki srveaedlgv yycfqgshvp
101 rtfgggtkle ikr;

(SEQ ID NO: 84)
  1 dvlmtqtpls lpvslgdqas iscrssqsiv hsnvntylew ylqkpgqspk
 51 lliykvsnrf sgvpdrfsgs gsgtdftlri srveaedlgi yycfqgshvp
101 ptfgggtkle ikr;

(SEQ ID NO: 85)
  1 dvvmtqtpls lpvslgdpas iscrssqsiv hsnvntylew ylqkpgqspk
 51 lliykvsnrf sgvpdrfsgs gagtdftlri srveaedlgi yycfqgshvp
101 ptfgggtkle ikr;

(SEQ ID NO: 86)
  1 elvmtqtpls lpvslgdqas iscrssqtiv hsngdtyldw flqkpgqspk
 51 lliykvsnrf sgvpdrfsgs gsgtdftlki srveaedlgv yycfqgshvp
101 ptfgggtkle ikr;

(SEQ ID NO: 87)
  1 dvlmtqtpls lpvslgdpas iscrssqsiv hsnvntylew ylqkpgqspk
 51 lliykvsnrf sgvpdrfsgs gagtdftlri srveaedlgi yycfqgshvp
101 ptfgggtkle ikr;
```

-continued

```
                                                  (SEQ ID NO: 88)
  1 dvvmtqtpls lpvslgdpas iscrssqsiv hsnvntylew ylqkpgqspr
 51 lliykvsnrf sgvpdrfsgs gagtdftlri srveaedlgi yycfqgshvp
101 ptfgggtkle ikr;

(SEQ ID NO: 89)
  1 dvlmtqtpvs lsvslgdqas iscrssqsiv hstgntylew ylqkpgqspk
 51 lliykisnrf sgvpdrfsgs gsgtdftlki srveaedlgv yycfqashap
101 rtfgggtkle ikr;

(SEQ ID NO: 90)
  1 dvlmtqtpls lpvslgdqas iscksssqsiv hssgntyfew ylqkpgqspk
 51 lliykvsnrf sgvpdrfsgs gsgtdftlki srveaedlgv yycfqgship
101 ftfgsgtkle ikr;

(SEQ ID NO: 91)
  1 dieltqtpls lpvslgdqas iscrssqsiv hsngntylew ylqkpgqspk
 51 lliykvsnrf sgvpdrfsgs gsgtdftlki srveaedlgv yycfqgshvp
101 ytfgggtkle ikr;

(SEQ ID NO: 92)
  1 dvlmtqtpls lpvslgdqas iscrssqsiv hsnvntylew ylqkpgqspk
 51 lliykvsnrf sgvpdrfsgs gsgtdftlri srveaedlgi yycfqgshvp
101 ptfgggtkle ikr;

(SEQ ID NO: 93)
  1 dvvmtqtpls lpvslgdpas iscrssqsiv hsnvntylew ylqkpgqspr
 51 lliykvsnrf sgvpdrfsgs gagtdftlri srveaedlgi yycfqgshvp
101 ptfgggtkle ikr;

(SEQ ID NO: 94)
  1 dvlmtqtpls lpvslgdqas iscrssqsiv hsnvntylew ylqkpgqspk
 51 lliykvsnrf sgvpdrfsgs gsgtdftlri srveaedlgi yycfqgshvp
101 ptfgggtkle ikr;

(SEQ ID NO: 95)
  1 dvvmtqtpls lpvslgdpas iscrssqsiv hsnvntylew ylqkpgqspk
 51 lliykvsnrf sgvpdrfsgs gagtdftlri srveaedlgi yycfqgshvp
101 ptfgggtkle ikr;

(SEQ ID NO: 96)
  1 dvlmtqtpls lpvslgdqas iscrsnqtil lsdgdtylew ylqkpgqspk
 51 lliykvsnrf sgvpdrfsgs gsgtdftlki srveaedlgv yycfqgshvp
101 ptfgggtkle ikr;

(SEQ ID NO: 97)
  1 dvlmtqtpls lpvslgdqas iscrssqtiv hsngntylew ylqkpgqspk
 51 lliykvtnrf sgvpdrfsgs gsgtdftlki srveaedlgv yycfqgthap
101 ytfgggtkle ikr;
and (SEQ ID NO: 98)
  1 dvlmtqtpls lpvslgdqas iscrssqsiv hsngntylew ylqkpgqspk
 51 lliysissrf sgvpdrfsgs gsgtdftlki srvqaedlgv yycfqgshvp
101 ytfgggtkle ikr.
```

The scope of the present invention includes methods wherein a patient is administered an anti-insulin-like growth factor receptor-1 (IGF1R) antibody wherein the variable region of the antibody is linked to any immunoglobulin constant region. In an embodiment, the light chain variable region is linked to a κ chain constant region. In an embodiment, the heavy chain variable region is linked to a γ1, γ2, γ3 or γ4 chain constant region. Any of the immunoglobulin variable regions set forth herein, in embodiments of the invention, can be linked to any of the foregoing constant regions.

In an embodiment of the invention, an IGF1R inhibitory agent that can be administered to a patient in a method according to the invention is AEW-541 (NVP-AEW-541; NVP-AEW-541-NX-7):

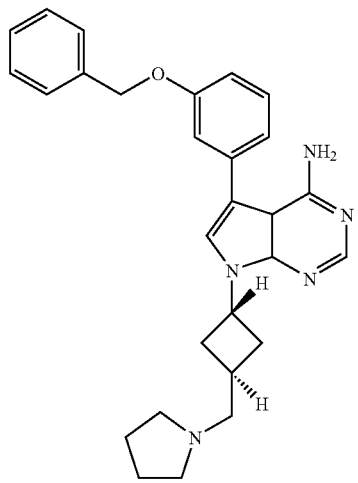

(Novartis; East Hanover, N.J.; see WO 2002/92599);

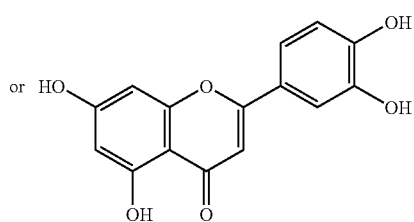

(WO 2003/39538).

In an embodiment of the invention, an IGF1R inhibitory agent that can be administered to a patient in a method according to the invention is any IGF1R anti-sense nucleic acid. For example, in an embodiment, the anti-sense IGF1R nucleic acid is ATL-1101 (Antisense Therapeutics Ltd; Australia). In an embodiment, the IGF1R anti-sense nucleic acid comprises any of the following nucleotide sequences: 5'-ATCTCTC-CGCTTCCTTTC-3' (SEQ ID NO: 99), 5'-ATCTCTCCGCT-TCCTTTC-3' (SEQ ID NO: 100), 5'-ATCTCTCCGCTTC-CTTTC-3' (SEQ ID NO: 101) or any IGF1R antisense nucleic acid set forth in any of US Published Patent Application No. US20030096769; Published International Application No. WO 2003/100059; Fogarty et al., Antisense Nucleic Acid Drug Dev. 2002 December; 12(6):369-77; White et al., J Invest Dermatol. 2002 June; 118(6):1003-7; White et al., Antisense Nucleic Acid Drug Dev. 2000 June; 10(3):195-203; or Wraight et al., Nat Biotechnol. 2000 May; 18(5):521-6.

In an embodiment of the invention, an IGF1R inhibitory agent that can be administered to a patient in a method according to the invention is an anti-IGF-I or II antibody; for example, any antibody disclosed in WO 2003/93317 or EP00492552.

The scope of the present invention includes any kinase inhibitor compound set forth in published international applications WO 2004/030627 or WO 2004/030625. In an embodiment, the kinase inhibitor is (±)-4-[2-(3-chloro-4-fluoro-phenyl)-2-hydroxy-ethylamino]-3-[6-(imidazol-1-yl)-4-methyl-1H-benzimidazol-2-yl]-1H-pyridin-2-one:

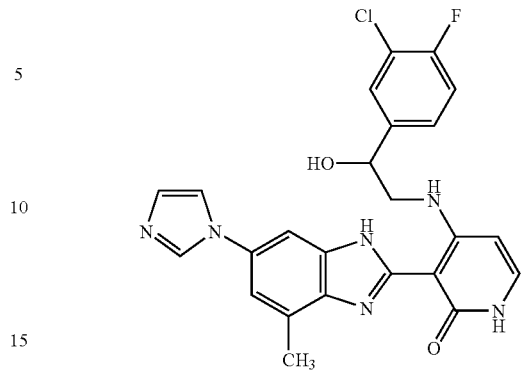

(optionally in combination with paclitaxel or with cetuximab).

In an embodiment of the invention, the IGR1R inhibitory agent is a soluble fragment of IGF1R (e.g., amino acids 30-902 of IGF1R) or siRNA (small interfering RNA) against IGF-1R.

In an embodiment, IGF1R comprises the amino acid sequence set forth under Genbank Accession No.: XM_052648 or NM_000612.

The present invention also includes embodiments wherein the patient receives both an IGF1R inhibitory agent in association with one or more other anti-cancer agents, including, but not limited to paclitaxel, thalidomide, docetaxel, gefitinib, temozolomide, lonafarnib, tipifarnib, letrozole, doxorubicin, cis-platin, oxaliplatin, camptothecan, topotecan, etoposide, vincristine, vinblastine, raloxifene, gemcitabine, retinoic acid, tamoxifen, trastuzumab, cetuximab or octreotide; or anti-cancer therapeutic procedures including, but not limited to, surgical tumorectomy or anti-cancer radiation therapy. The present invention further includes embodiment wherein two or more IGF1R inhibitory agents are administered in association with one another.

The term "in association" indicates that the components of the combinations of the invention can be formulated into a single composition for simultaneous delivery or formulated separately into two or more compositions (e.g., a kit). Furthermore, each component of a combination of the invention can be administered to a subject at a different time than when the other component is administered; for example, each administration may be given non-simultaneously at several intervals over a given period of time. Moreover, the separate components may be administered to a subject by the same or by a different route (e.g., orally, intravenously, intratumorally).

Generation of Antibodies

Any suitable method can be used to elicit an antibody with the desired biologic properties to inhibit IGF1R. It is desirable to prepare monoclonal antibodies (mAbs) from various mammalian hosts, such as mice, rodents, primates, humans, etc. Description of techniques for preparing such monoclonal antibodies may be found in, e.g., Stites, et al. (eds.) BASIC AND CLINICAL IMMUNOLOGY (4th ed.) Lange Medical Publications, Los Altos, Calif., and references cited therein; Harlow and Lane (1988) ANTIBODIES: A LABORATORY MANUAL CSH Press; Goding (1986) MONOCLONAL ANTIBODIES: PRINCIPLES AND PRACTICE (2d ed.) Academic Press, New York, N.Y. Thus, monoclonal antibodies may be obtained by a variety of techniques familiar to researchers skilled in the art. Typically, spleen cells from an animal immunized with a desired antigen are immortalized, commonly by fusion with a myeloma cell. See Kohler and Milstein (1976) Eur. J. Immunol. 6:511-519. Alternative methods of immortalization include transformation with Epstein Barr Virus, oncogenes, or retroviruses, or other methods known in the art. See, e.g., Doyle, et al. (eds. 1994 and periodic supplements) CELL AND TISSUE CULTURE: LABORATORY PROCEDURES, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) Science 246:1275-1281. Modified antibodies can be generated, for example, by introducing mutations in DNA encoding an immunoglobulin chain, for example, by use of conventional recombinant biological techniques.

Other suitable techniques involve selection of libraries of antibodies in phage or similar vectors. See, e.g., Huse et al., Science 246:1275-1281 (1989); and Ward et al., Nature 341:544-546 (1989). The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly U.S. Pat. No. 4,816,567; and Queen et al. (1989) Proc. Nat'l Acad. Sci. USA 86:10029-10033; or made in transgenic mice, see Mendez et al. (1997) Nature Genetics 15:146-156. Further methods for producing chimeric, humanized and human antibodies are well known in the art. See, e.g., U.S. Pat. No. 5,530,101, issued to Queen et al, U.S. Pat. No. 5,225,539, issued to Winter et al, U.S. Pat. No. 4,816,397 issued to Boss et al, all of which are incorporated by reference in their entirety.

Tumor Analysis

The methods of the present method comprise determining whether tumor cells comprising one or more of the following characteristics:
  (i) IRS-1 phosphorylation on tyrosine 896;
  (ii) IRS-1 phosphorylation on tyrosine 612;
  (iii) IRS-1 phosphorylation on any tyrosine;
  (iv) IGF-II expression;
  (v) IGF1R phosphorylation on any tyrosine; or
  (vi) expression of IGF1R.

Tumor cells can be assayed to determine whether any of these characteristics are present by any of several methods commonly known in the art. In an embodiment, IRS-1 or IGF1R tyrosine phosphorylation can be determine by western blot analysis with an anti-phosphotyrosine antibody. For example, anti-phosphotyrosine antibodies PY20, PT66 and P-Try-100 are commercially available from PerkinElmer Life and Analytical Sciences, Inc. (Boston, Mass.); and anti-phosphotyrosine antibody 4G10 is commercially available from Upstate Cell Signaling Solutions (Waltham, Mass.). Western blot analysis is a conventional method that is well known in the art. In an embodiment, IRS-1 or IGF1R tyrosine phosphorylation can be determine by an Enzyme linked immunosorbent assay (ELISA) or immunoprecipitation. In an embodiment, expression of IGF1R or IGF-II by tumor cells can, similarly, be determined by western blot analysis, immunoprecipitation or by ELISA. Any of several anti-IGF1R antibodies known in the art, for example, as described herein, can be used.

Many references are available to provide guidance in applying the above techniques (Kohler et al., Hybridoma Techniques (Cold Spring Harbor Laboratory, New York, 1980); Tijssen, Practice and Theory of Enzyme Immunoassays (Elsevier, Amsterdam, 1985); Campbell, Monoclonal Antibody Technology (Elsevier, Amsterdam, 1984); Hurrell, Monoclonal Hybridoma Antibodies: Techniques and Applications (CRC Press, Boca Raton, Fla., 1982); Zola, Monoclonal Antibodies: A Manual of Techniques, pp. 147-158 (CRC Press, Inc., 1987)).

In an embodiment of the invention, IGF-II expression by a tumor cell can be determined by IGF-II RNA detection. In an embodiment of the invention, IGF-II RNA is determined by northern blot analysis. Northern blot analysis is a conventional technique well known in the art and is described, for example, in Molecular Cloning, a Laboratory Manual, second edition, 1989, Sambrook, Fritch, Maniatis, Cold Spring Harbor Press, 10 Skyline Drive, Plainview, N.Y. 11803-2500.

Dosage

In an embodiment, an IGF1R inhibitory agent is administered to a patient at a "therapeutically effective dosage" or "therapeutically effective amount" which preferably inhibits a disease or condition (e.g., tumor growth) to any extent—preferably by at least about 20%, more preferably by at least about 40%, even more preferably by at least about 60%, and still more preferably by at least about 80%-100% relative to untreated subjects. In an embodiment of the invention, the term "therapeutically effective amount" or "therapeutically effective dosage" means that amount or dosage of an IGF1R inhibitory agent (e.g., an anti-IGF1R antibody or antigen-binding fragment thereof) that will elicit a biological or medical response of a tissue, system, subject or host that is being sought by the administrator (such as a researcher, doctor or veterinarian) which includes any measurable alleviation of the signs, symptoms and/or clinical indicia of cancer (e.g., tumor growth) and/or the prevention, slowing or halting of progression or metastasis of cancer to any degree. The ability of an IGF1R inhibitory agent to inhibit cancer can be evaluated in an animal model system predictive of efficacy in human tumors. Alternatively, efficacy can be evaluated by examining the ability of a treatment of the invention or any component thereof to inhibit tumor cell growth in vitro by assays well-known to the skilled practitioner. One of ordinary skill in the art would be able to determine such amounts based on such factors as the subject's size, the severity of the subject's symptoms, and the particular composition or route of administration selected.

A clinician may use any of several methods known in the art to measure the effectiveness of a particular dosage scheme of an IGF1R inhibitory agent. For example, tumor size can be determined in a non-invasive route, such as by X-ray, positron emission tomography (PET) scan, computed tomography (CT) scan or magnetic resonance imaging (MRI).

A cancer or a tumor cell is "responsive" to an IGF1R inhibitory agent if the agent can provide any measurable alleviation of the signs, symptoms and/or clinical indicia of cancer (e.g., tumor growth) and/or the prevention, slowing or halting of progression or metastasis of cancer to any degree.

Dosage regimens may be adjusted to provide the optimum desired response (e.g., a therapeutic response). For example, a dose may be administered, several divided doses may be administered over time or the dose may be proportionally reduced or increased as indicated by exigencies of the therapeutic situation. It is especially advantageous to formulate parenteral compositions in dosage unit form for ease of administration and uniformity of dosage.

A physician or veterinarian having ordinary skill in the art can readily determine and prescribe the effective amount of the pharmaceutical composition required. For example, the physician or veterinarian could start doses of an IGF1R inhibitory agent employed in the pharmaceutical composition at levels lower than that required in order to achieve the desired therapeutic effect and gradually increase the dosage until the desired effect is achieved. The effectiveness of a given dose or treatment regimen of IGF1R inhibitory agent can be determined, for example, by determining whether a tumor being treated in the subject shrinks or ceases to grow.

In an embodiment of the invention, administration of IGF1R inhibitory agent is by injection proximal to the site of the target (e.g., tumor). In an embodiment, a therapeutically effective daily dose of IGF1R inhibitory agent or pharmaceutical composition thereof is administered as two, three, four, five, six or more sub-doses administered separately at appropriate intervals throughout the day. In an embodiment, a "therapeutically effective" dosage of any anti-IGFR antibody (e.g., 19D12/15H12 LCF/HCA) is in the range of about 3 mg/kg (body weight) to about 20 mg/kg (e.g., 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg or 20 mg/kg) per day. In an embodiment, a "therapeutically effective dosage" of a chemotherapeutic agent (e.g., an IGF1R inhibitory agent) is whenever possible as set forth in the *Physicians' Desk Reference* 2003 (Thomson Healthcare; 57$^{th}$ edition (Nov. 1, 2002)) which is herein incorporated by reference. For example, in an embodiment of the invention, a therapeutically effective dosage of NVP-ADW-742 is about 1 mg/kg/day to about 50 mg/kg/day (e.g., 5 mg/kg/day, 10 mg/kg/day, 15 mg/kg/day, 20 mg/kg/day, 25 mg/kg/day, 30 mg/kg/day, 35 mg/kg/day, 40 mg/kg/day, 45 mg/kg/day).

Therapeutic Methods and Administration

An IGF1R inhibitory agent can be used to inhibit or reduce the growth or proliferation of any cell, such as a malignant cell, either in vitro (e.g., in cell culture) or in vivo (e.g., within the body of a subject suffering from a disease mediated by elevated expression or activity of IGF1R or by elevated expression of its ligand (e.g., IGF-I or IGF-II)). Such inhibition or reduction of growth or proliferation of a cell can be achieved by contacting the cell with the IGF1R inhibitory agent.

In an embodiment, an IGF1R inhibitory agent is for treating cancer in a patient that is characterized by one or more of the following characteristics: IRS-1 phosphorylation on tyrosine 896; (ii) IRS-1 phosphorylation on tyrosine 612; (iii) IRS-1 phosphorylation on any tyrosine; (iv) IGF-II expression; (v) IGF1R phosphorylation on any tyrosine; or (vi) expression of IGF1R. For example, in an embodiment, the cancer is bladder cancer, Wilm's cancer, bone cancer, prostate cancer, lung cancer, endometrial cancer, multiple myeloma, non-small cell lung cancer (NSCLC), colon cancer, rectal cancer, colorectal cancer, breast cancer (estrogen receptor $^+$ or estrogen receptor $^-$), cervical cancer, synovial sarcoma, ovarian cancer, pancreatic cancer, neuroblastoma, rhabdomyosarcoma, osteosarcoma, diarrhea associated with metastatic carcinoid or vasoactive intestinal peptide secreting tumor (e.g., VIPoma or Werner-Morrison syndrome).

In an embodiment, it is in initially determined if a prospective patient to be treated with an IGF1R inhibitory agent suffers from a variety of cancer that is commonly known to exhibit one of the following characteristics: (i) IRS-1 phosphorylation on tyrosine 896; (ii) IRS-1 phosphorylation on tyrosine 612; (iii) IRS-1 phosphorylation on any tyrosine; (iv) IGF-II expression; (v) IGF1R phosphorylation on any tyrosine; or (vi) expression of IGF1R. If the patient is determined to suffer from a cancer known to be characterized by one or more of the 6 characteristics set forth above, the patient is selected for treatment with an IGF1R inhibitory agent. A tumor type may be known to comprise any of the listed characteristics, for example, if such is established in scientific literature (e.g., periodic journals or textbooks) or if such is commonly known in the art by practitioners of ordinary skill or if such a characteristic has ever been observed in one or more patients or tumors, or if such can reasonably be inferred from experimental data (e.g., in vitro or in vivo data including animal data).

In an embodiment of the invention, a prospective patient's individual tumor is analyzed and it is determined whether the tumor exhibits one of more of the 6 characteristics: (i) IRS-1 phosphorylation on tyrosine 896; (ii) IRS-1 phosphorylation on tyrosine 612; (iii) IRS-1 phosphorylation on any tyrosine; (iv) IGF-II expression; (v) IGF1R phosphorylation on any tyrosine; or (vi) expression of IGF1R. In this embodiment, if the patient's tumor is determined to be characterized by one or more of the 6 characteristics set forth above, the patient is selected for treatment with an IGF1R inhibitory agent. In an embodiment, it is first determined whether the patient's tumor expresses the characteristic (i) IRS-1 phosphorylation on tyrosine 896 or (ii) IRS-1 phosphorylation on tyrosine 612; then, if such a characteristic is identified, it is determined whether the tumor comprises the characteristic (iv) IGF-II expression; if the patient's tumor is determined to express characteristic (i) or (ii) and characteristic (iv), then the patient is selected for treatment with an IGF1R inhibitory agent.

The cells from a particular patient's tumor can be obtained surgically, for example, by surgical biopsy. For example, a tumor biopsy can be taken by endoscopic biopsy, excisional or incisional biopsy or fine needle aspiration (FNA) biopsy.

The term "patient" or "subject" includes any organism, preferably an animal, more preferably a mammal (e.g., rat, mouse, dog, cat, rabbit) and most preferably a human.

As stated above, in an embodiment of the invention, where possible, an IGF1R inhibitory agent is administered to a subject in accordance with the Physicians' Desk Reference 2003 (Thomson Healthcare; 57th edition (Nov. 1, 2002)) or as set forth herein.

An IGF1R inhibitory agent can be administered by an invasive route such as by injection (see above). Administration by a non-invasive route (e.g., orally; for example, in a pill, capsule or tablet) is also within the scope of the present invention. In an embodiment of the invention, an anti-IGF1R antibody (e.g., 15H12/19D12 LCF/HCA), or pharmaceutical composition thereof, is administered intravenously, subcutaneously, intramuscularly, intraarterially or intratumorally.

An IGF1R inhibitory agent can be administered with medical devices known in the art. For example, a pharmaceutical composition of the invention can be administered by injection with a hypodermic needle.

The pharmaceutical compositions of the invention may also be administered with a needleless hypodermic injection device; such as the devices disclosed in U.S. Pat. No. 6,620,135; 6,096,002; 5,399,163; 5,383,851; 5,312,335; 5,064,413; 4,941,880; 4,790,824 or 4,596,556.

Examples of well-known implants and modules for administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Pharmaceutical Compositions

An IGF1R inhibitory agent can be incorporated into a pharmaceutical composition, along with a pharmaceutically acceptable carrier, suitable for administration to a subject in vivo. The scope of the present invention includes pharmaceutical compositions which are suitable to be administered to a subject by any route including, for example, oral, ocular, topical, pulmonary (inhalation), intratumoral injection, intravenous injection, subcutaneous injection or intramuscular injection.

For general information concerning formulations, see, e.g., Gilman, et al., (eds.) (1990), *The Pharmacological Bases of Therapeutics,* 8th Ed., Pergamon Press; A. Gennaro (ed.), *Remington's Pharmaceutical Sciences,* 18th Edition, (1990), Mack Publishing Co., Easton, Pa.; Avis, et al., (eds.) (1993) *Pharmaceutical Dosage Forms: Parenteral Medications* Dekker, New York; Lieberman, et al., (eds.) (1990) *Pharmaceutical Dosage Forms: Tablets* Dekker, New York; and Lieberman, et al., (eds.) (1990), *Pharmaceutical Dosage Forms: Disperse Systems* Dekker, New York, Kenneth A. Walters (ed.) (2002) *Dermatological and Transdermal Formulations (Drugs and the Pharmaceutical Sciences)*, Vol 119, Marcel Dekker.

Pharmaceutically acceptable carriers are conventional and very well known in the art. Examples include aqueous and nonaqueous carriers, stabilizers, antioxidants, solvents, dispersion media, coatings, antimicrobial agents, buffers, serum proteins, isotonic and absorption delaying agents, and the like that are physiologically compatible. Preferably, the carrier is suitable for injection into a subject's body.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Examples of pharmaceutically-acceptable antioxidants include: water soluble antioxidants such as ascorbic acid, cysteine hydrochloride, sodium bisulfate, sodium metabisulfite, sodium sulfite and the like; and oil-soluble antioxidants such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Prevention of the presence of microorganisms may be ensured both by sterilization procedures, and by the inclusion of various antimicrobial agents such as EDTA, EGTA, paraben, chlorobutanol, phenol sorbic acid, and the like.

Suitable buffers which may be included in the pharmaceutical compositions of the invention include L-histidine based buffers, phosphate based buffers (e.g., phosphate buffered saline, pH≅7), sorbate based buffers or glycine-based buffers.

Serum proteins which may be included in the pharmaceutical compositions of the invention may include human serum albumin.

Isotonic agents, such as sugars (e.g., sucrose), ethanol, polyalcohols (e.g., glycerol, propylene glycol, liquid polyethylene glycol, mannitol or sorbitol), sodium citrate or sodium chloride (e.g., buffered saline) may also be included in the pharmaceutical compositions of the invention. In an embodiment of the invention, the sugar, for example, glucose or sucrose is present at a high concentration (e.g., about 10-100 mg/ml, e.g., 50 mg/ml, 60 mg/ml or 70 mg/ml).

Prolonged absorption of an injectable pharmaceutical form may be brought about by the inclusion of agents which delay absorption such as aluminum monostearate and/or gelatin.

Dispersions can also be prepared in glycerol, liquid polyethylene glycols, and mixtures thereof and in oils.

Pharmaceutically acceptable carriers include sterile aqueous solutions or dispersions and sterile powders for the extemporaneous preparation of sterile injectable solutions or dispersions. The use of such media and agents for pharmaceutically active substances is well known in the art.

Sterile injectable solutions comprising an anti-IGF1R antibody can be prepared by incorporating the antibody or antigen-binding fragment thereof in the required amount in an appropriate solvent, optionally with one or a combination of ingredients enumerated above, as required, followed by sterilization microfiltration. Generally, dispersions are prepared by incorporating the antibody into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional, desired ingredient from a previously sterile-filtered solution thereof.

In an embodiment of the invention, an anti-IGF1R antibody of the invention is in a pharmaceutical formulation comprising a therapeutically effective amount of said antibody, a buffer and sucrose. For example, in an embodiment of the invention, the buffer is any one of phosphate buffer, citrate buffer, histidine buffer, glycine buffer or acetate buffer. The pharmaceutical formulation can be within any suitable pH range. In an embodiment of the invention, the pH is 5.0, 5.5, 6.0, 7.5, or between about 5.5 and about 6 or between about 5 and about 7.

An IGF1R inhibitory agent including an anti-IGF1R antibody or antigen-binding fragment thereof can be orally administered. Pharmaceutical compositions for oral administration may contain, in addition to the binding composition, additives such as starch (e.g., potato, maize or wheat starch or cellulose), starch derivatives (e.g., microcrystalline cellulose or silica), sugars (e.g., lactose), talc, stearate, magnesium carbonate or calcium phosphate. In order to ensure that oral compositions comprising an antibody or antigen-binding fragment of the invention are well tolerated by the patient's digestive system, mucus formers or resins may be included. It may also be desirable to improve tolerance by formulating the antibody or antigen-binding fragment in a capsule which is insoluble in the gastric juices. An exemplary pharmaceutical composition of this invention in the form of a capsule is prepared by filling a standard two-piece hard gelatin capsule with the antibody or antigen-binding fragment of the invention in powdered form, lactose, talc and magnesium stearate. Oral administration of immunoglobulins has been described (Foster, et al., (2001) Cochrane Database System rev. 3:CD001816)

An IGF1R inhibitory agent may also be included in a pharmaceutical composition for topical administration. Formulations suitable for topical administration include liquid or semi-liquid preparations suitable for penetration through the skin to the site where treatment is required, such as liniments, lotions, creams, ointments or pastes, and drops suitable for administration to the eye, ear or nose.

Drops may comprise sterile aqueous or oily solutions or suspensions and may be prepared by dissolving an IGF1R inhibitory agent in a suitable aqueous solution of a bactericidal and/or fungicidal agent and/or any other suitable preservative, and preferably including a surface active agent. The resulting solution may then be clarified by filtration.

Lotions according to the present invention include those suitable for application to the skin or eye. An eye lotion may comprise a sterile, aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing an IGF1R inhibitory agent in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

An IGF1R inhibitory agent may also be administered by inhalation. A suitable pharmaceutical composition for inhalation may be an aerosol. An exemplary pharmaceutical composition for inhalation of an antibody or antigen-binding fragment of the invention may include: an aerosol container with a capacity of 15-20 ml comprising the antibody or antigen-binding fragment of the invention, a lubricating agent, such as polysorbate 85 or oleic acid, dispersed in a propellant, such as freon, preferably in a combination of 1,2-dichlorotetrafluoroethane and difluorochloromethane. Preferably, the composition is in an appropriate aerosol container adapted for either intranasal or oral inhalation administration.

Kits and Articles of Manufacture

Kits and articles of manufacture of the present invention include an IGF1R inhibitory agent, preferably combined with a pharmaceutically acceptable carrier, in a pharmaceutical formulation, more preferably in a pharmaceutical dosage form such as a pill, a powder, an injectable liquid, a tablet, dispersible granules, a capsule, a cachet or a suppository. See for example, Gilman et al. (eds.) (1990), The Pharmacological Bases of Therapeutics, 8th Ed., Pergamon Press; and Remington's Pharmaceutical Sciences, supra, Easton, Pa.; Avis et al. (eds.) (1993) Pharmaceutical Dosage Forms: Parenteral Medications Dekker, New York; Lieberman et al. (eds.) (1990) Pharmaceutical Dosage Forms: Tablets Dekker, New York; and Lieberman et al. (eds.) (1990), Pharmaceutical Dosage Forms: Disperse Systems Dekker, New York.

The kits and articles of manufacture of the present invention also include information, for example in the form of a package insert or label, indicating that the target of the IGF1R inhibitory agent is IGF1R. The term "target" indicates that the agent reduces or inhibits ligand binding, kinase activity, expression or any other biological activity of IGF1R in any way. The insert or label may take any form, such as paper or on electronic media such as a magnetically recorded medium (e.g., floppy disk) or a CD-ROM.

The label or insert may also include other information concerning the pharmaceutical compositions and dosage forms in the kit or article of manufacture. Generally, such information aids patients and physicians in using the enclosed pharmaceutical compositions and dosage forms effectively and safely. For example, the following information regarding the IGF1R inhibitory agent may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references and patent information.

EXAMPLES

This section is intended to further describe the present invention and should not be construed to further limit the invention. Any composition or method set forth herein comprises part of the present invention.

In this example, the level of phosphorylation of IRS-1 in human lung tumor tissue was compared to that of normal tissue samples and found to be higher in tumor cells than in normal cells. Also, the in vivo efficacy of the anti-IGF1R antibody 19D12/15H12 LCF/HCA was correlated with the ability of the IGF-1 to cause IRS-1 phosphorylation. In addition, the level of IGF-II mRNA expression was evaluated in 56 different normal and cancerous ovarian and colorectal tissue samples and found to be high in several samples of tumor tissue.

Tumor lysate preparation. Tumor tissues were first weighed and pulverized into fine powder with a pre-chilled pulverizer on dry ice. Tumor powders were transferred into a tube, and 4.5× volume of the buffer A (i.e., 450 ul buffer A per 100 mg tissue) was added. The samples were sonicated for 30 seconds, 0.5× volume of buffer B (i.e., add 50 ul buffer B per 100 mg tissue powder) was added, and samples were spun for 13,000 rpm for 20 min at 4° C. after incubation on ice for 30 min. Supernatants were collected and protein concentrations of the lysates were determined by Bio-Rad assay.

Buffer A: 50 mM Hepes, pH 7.4, 150 mM NaCl, 5% Glycerol, 1.5 mM MgCl2, 2 mM Sodium Vanadate, 5 mM NaF, Protease inhibitors (2× concentrated C complete EDTA-free from Roche-cat #. 1 873 580), Phosphatase inhibitor Cocktail 1 (Sigma p2850), Phosphatase inhibitor Cocktail 2 (Sigma p5726).

Buffer B: Buffer A plus 10% Triton-100

Cell culture lysate preparation. Cells were washed in PBS once, lysed in buffer containing 50 mM Hepes, pH7.4, 150 mM NaCl, 10% glycerol, 1% Triton X-100, 1.5 mM MgCl2, 2 mM Na3VO4 and protease inhibitor cocktail (Complete™, Roche Diagnostics GmbH; Mannheim, Germany). Samples were spun for 13,000 rpm for 10 min at 4° C. after incubation on ice for 30 min. Supernatants were collected and protein concentrations of the lysates were determined by Bio-Rad assay.

Western analysis. Equal amounts of cell or tumor lysates were separated on a SDS-PAGE, transferred to nitrocellulose filters, probed with desired antibodies, and visualized by ECL (Amersham; Piscataway, N.J.). Antibodies for detecting IGFR and IRS-1 were from Santa Cruz Biotechnology (Santa Cruz, Calif.). Antibodies against phospho-IRS1[pY896] and phospho-IRS1[pY612] were from Biosource (Camarillo, Calif.).

IGF-II protein measurement. Cells from various cell lines were seeded in T-175 plates in medium containing 10% FBS. After cells were attached, medium was changed to serum free medium. Medium was collected, all debris was spun down, and the supernatants were lyophilized. Cells on the plates were trypsinized and counted. Water was added to each lyophilized supernatant sample (1 ml/2×10$^7$ cells). IGF-II was measured using the IGF-II ELISA kit from DSL (DSL-10-2600). IGF-II amounts were determined by the standard curve and reported as nanogram IGF-II per 1×10$^6$ cells.

IGF-II mRNA measurement. RNAs were made from tumor samples and cDNAs were synthesized. Expression of IGF-II was analyzed on 20 ng of cDNA sample in a Fluorogenic 5'-nuclease PCR assay with specific probes and primers using the ABI Prism 7700 Sequence Detection System (Applied Biosystems; Foster City, Calif.). CT numbers were normalized by determining Ubiquitin (reference gene) mRNA expression in all samples.

```
IGF2/forward:
AGGAGCTCGAGGCGTTCAG        (SEQ ID NO: 102)

IGF2/reverse:
GTCTTGGGTGGGTAGAGCAATC     (SEQ ID NO: 103)

probe:
AGGCCAAACGTCACCGTCCCC      (SEQ ID NO: 104)
```

Xenograft models in mice. Four to five million human tumor cells (H322, H838, A2780, ES2, MCF7, SW-527, SK-N-AS, SK-N-MC) in Matrigel were inoculated subcutaneously into each nude mouse. When the tumor size reached at least ~50 mm$^3$, 19D12/15H12 LCF/HCA treatment was initiated and continued with dosing two times per week. 19D12/15H12 LCF/HCA was injected into each nude mouse, intraperitoneally, at 0.004 mg/mouse, 0.02 mg/mouse, 0.1 mg/mouse or 0.5 mg/mouse. Tumor volumes were measured by Labcat.

IRS-1 phosphorylation level in human lung cancer and normal tissue samples. Twelve pairs of samples of normal and cancerous human lung cancerous tissue samples were obtained from patients. Cell lysates were prepared from the tissue samples and subjected to western blot analysis, staining with anti-phospho-IRS1[pY896] as described above. Total IRS-1 was also measured by staining with an anti-IRS antibody.

The western blot data generated in these experiments is set forth in FIG. 1. In 6 out of the 12 sample pairs evaluated (50%), greater phospho-IRS-1 levels were observed in tumor tissue samples than in the corresponding normal tissue sample.

Similar results were observed when the level of IRS-1 phosphorylation was measured in normal and cancerous colorectal tissue samples. The colorectal tissue samples were evaluated essentially identically to that way the lung tissue samples were evaluated.

Correlation of In vivo efficacy of 19D12/15H12 LCF/HCA with IRS-1 phosphorylation. To evaluate in vivo efficacy of 19D12/15H12 LCF/HCA antibody, nude mice bearing human tumor xenografts were administered the antibody or an isotype control, and tumor volume was evaluated over time as described above.

To evaluate IRS-1 phosphorylation in tumor cell lines, cell lines were grown in the presence of absence of 100 ng/ml IGF-I. Cell lysates of A2780, ES2, H322, H838 and SK-N-AS cells were then prepared and evaluate-d by western blot analysis as describe above.

The results of the in vivo efficacy experiments are set forth in FIG. 2. The 19D12/15H12 LCF/HCA antibody was found to be effective at inhibiting the growth of several types of tumors in vivo (e.g., non-small cell lung cancer, ovarian cancer, breast cancer, neuroblastoma).

Figure 3:
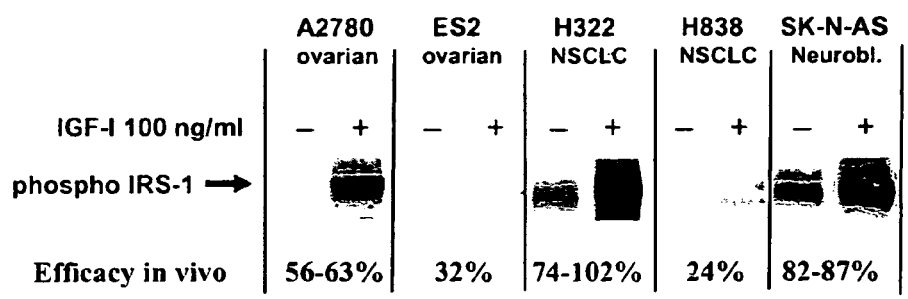
FIG. 3. In Vivo Efficacy of 19D12/15H12 LCF/HCA Correlates with Sensitivity of IRS-1 Phosphorylation to IGF-I. In the "−" and "+" lanes, the quantity of phosphorylated IRS-1, in each cell line evaluated, is shown in the absence and presence of IGF-I, respectively. The level of in vivo efficacy of 19D12/15H12 LCF/HCA at inhibiting growth of the indicated cell line (see FIG. 2) is also indicated.

The results of the experiments measuring basal and IGF-I stimulated IRS-1 phosphorylation in tumor cells are set forth in FIG. 3. The A2780, H322 and SK-N-AS cell lines evaluated exhibited the greatest basal and IGF-I stimulated IRS-1 phosphorylation.

The cell lines that were most sensitive, in vivo, to growth inhibition by 19D12/15H12 LCF/HCA (FIG. 2) were those that showed the greatest basal and IGF-I stimulated IRS-1 phosphorylation (FIG. 3).

Figure 4:
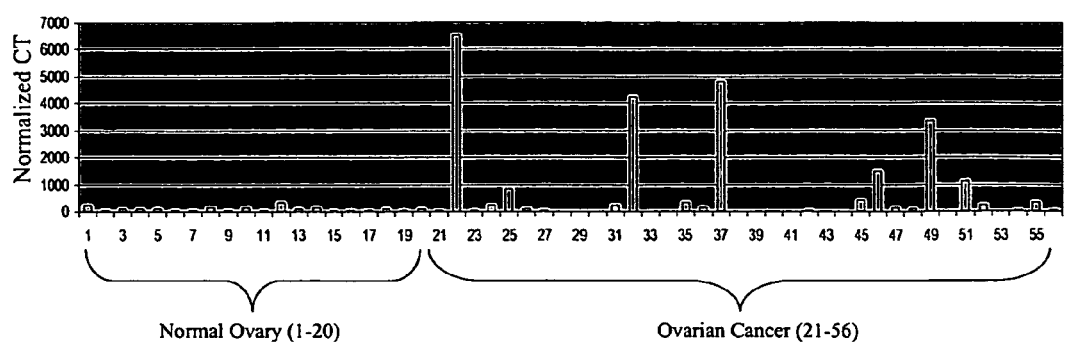
FIG. 4. Overexpression of IGF-II mRNA in Human Ovarian Tumor Samples. The normalized level of IGF-II mRNA expression observed in each of the 20 normal ovarian tissue samples and 36 cancerous ovarian tissue samples is shown.
Figure 5:
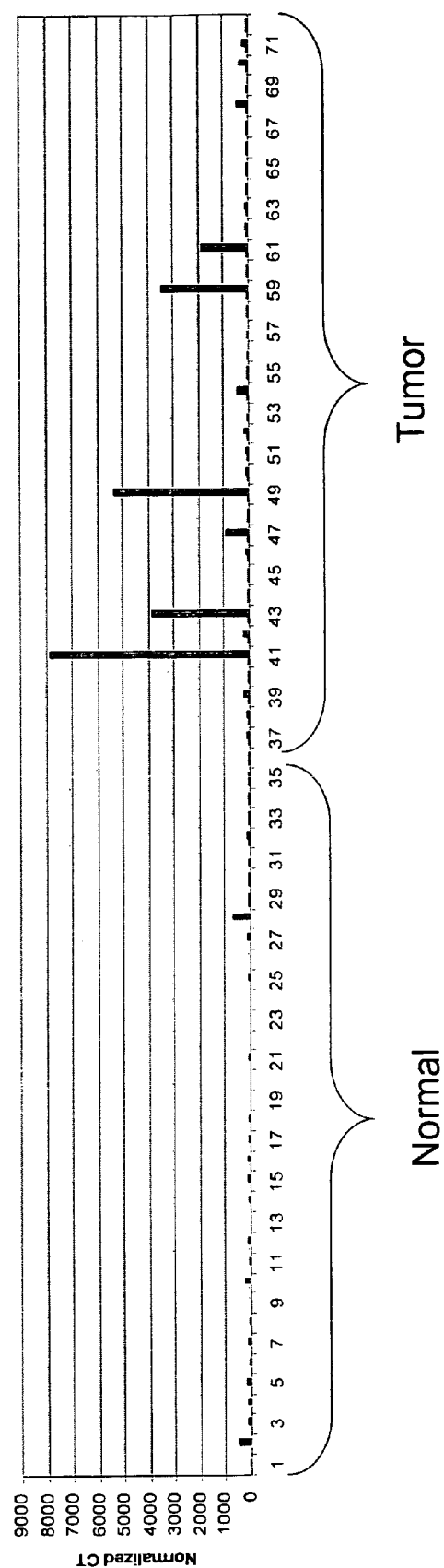
FIG. 5. Overexpression of IGF-II mRNA in Human Colorectal Tumor Samples. The normalized level of IGF-II mRNA expression observed in each of the 36 normal ovarian tissue samples and 36 cancerous colorectal tissue samples is shown.

IGF-II mRNA expression level in ovarian and colorectal tumor samples. Normal and cancerous ovarian and colorectal tissue samples were obtained from multiple cancer patients. The level of IGF-II mRNA expression was evaluated, by Taqman analysis, as described above. The level of IGF-II mRNA expression of each ovarian tissue sample is set forth in FIG. 4 and the level of IGF-II mRNA expression in each colorectal tissue sample is set forth in FIG. 5. In these experiments, 20% of ovarian tumor samples were found to overexpress IGF-II mRNA as compared to normal ovarian tissue samples. Fifty three percent of colorectal samples were found to overexpress IGF-II mRNA as compared with adjacent, normal colorectal samples.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, Genbank Accession Numbers and publications are cited throughout this application, the disclosures of which are incorporated herein by reference in their entireties.

We claim:

1. A method for treating a non-small cell lung tumor, an ovarian tumor, a neuroblastoma tumor or an osteosarcoma tumor in a mammalian patient wherein growth or survival of the tumor is mediated by IGF1R expression or activity said method comprising:
   (a) selecting a mammalian patient having a non-small cell lung tumor, an ovarian tumor, a neuroblastoma tumor or an osteosarcoma tumor expressing phosphorylated IRS-1 tyrosine 896 or phosphorylated IRS-1 tyrosine 612; and
   (b) administering to said mammalian patient a therapeutically effective amount of an isolated antibody that binds specifically to IGF1R comprising a light chain immunoglobulin variable domain comprising the amino acid sequence: EIVLTQSPGTLSVSPGERATLSCRASQSIGSSLHWYQQKPGQAPRLLIKYASQSLSGIPDRFSGSGSGTDFTLTISRLEPEDFAVYYCHQSSRLPHTFGQGTKVEIKRT (amino acids 20-128 of SEQ ID NO: 8); and a heavy chain immunoglobulin variable domain comprising the amino acid sequence: EVQLVQSGGGLVKPGGSLRLSCAASGFTFSSFAMHWVRQAPGKGLEWISVIDTRGATYYADSVKGRFTISRDNAKNSLYLQMNSLRAEDTAVYYCARLGNFYYGMDVWGQGTTVTVSS (amino acids 20-137 of SEQ ID NO: 10); wherein said antibody inhibits growth or survival of said tumor.

2. The method of claim 1 wherein the tumor is an osteosarcoma tumor.

3. The method of claim 2 wherein the antibody is a monoclonal antibody and the patient is a human.

4. The method of claim 2 wherein the antibody is a fully human monoclonal antibody and the patient is a human.

5. The method of claim 3 wherein said light chain immunoglobulin variable domain is conjugated to an immunoglobulin kappa constant domain and said heavy chain immunoglobulin variable domain is conjugated to an immunoglobulin gamma 1 constant domain.

6. The method of claim 4 wherein said light chain immunoglobulin variable domain is conjugated to an immunoglobulin kappa constant domain and said heavy chain immunoglobulin variable domain is conjugated to an immunoglobulin gamma 1 constant domain.

7. The method of claim 3 wherein said patient is administered the monoclonal antibody in association with one or more additional anti-cancer agents.

8. The method of claim 7 wherein the patient is administered said monoclonal antibody in association with one or more additional anti-cancer agents selected from the group consisting of: paclitaxel, thalidomide, docetaxel, gefitinib, temozolomide, lonafarnib, tipifarnib, letrozole, doxorubicin, cis-platin, oxaliplatin, camptothecin, topotecan, etoposide, vincristine, vinblastine, raloxifene, gemcitabine, retinoic acid, tamoxifen, trastuzumab, cetuximab and octreotide.

9. The method of claim 4 wherein said patient is administered the monoclonal antibody in association with one or more additional anti-cancer agents.

10. The method of claim 9 wherein the patient is administered said monoclonal antibody in association with one or more additional anti-cancer agents selected from the group consisting of: paclitaxel, thalidomide, docetaxel, gefitinib, temozolomide, lonafarnib, tipifarnib, letrozole, doxorubicin, cis-platin, oxaliplatin, camptothecin, topotecan, etoposide, vincristine, vinblastine, raloxifene, gemcitabine, retinoic acid, tamoxifen, trastuzumab, cetuximab and octreotide.

11. The method of claim 8 wherein the additional anti-cancer agent is paclitaxel.

12. The method of claim 8 wherein the additional anti-cancer agent is docetaxel.

13. The method of claim 8 wherein the additional anti-cancer agent is gefitinib.

14. The method of claim 8 wherein the additional anti-cancer agent is cis-platin.

15. The method of claim 8 wherein the additional anti-cancer agent is oxaliplatin.

16. The method of claim 8 wherein the additional anti-cancer agent is octreotide.

* * * * *

SEQUENCE LISTING

<160> NUMBER OF SEQ ID NOS: 105

<210> SEQ ID NO 1
<211> LENGTH: 384
<212> TYPE: DNA
<213> ORGANISM: Artificial Sequence
<220> FEATURE:
<223> OTHER INFORMATION: Modified 19D12/15H12 Light Chain-C
<220> FEATURE:
<221> NAME/KEY: CDS
<222> LOCATION: (1)..(384)

<400> SEQUENCE: 1

```
atg tcg cca tca caa ctc att ggg ttt ctg ctg ctc tgg gtt cca gcc      48
Met Ser Pro Ser Gln Leu Ile Gly Phe Leu Leu Leu Trp Val Pro Ala
1               5                   10                  15 tcc agg ggt gaa att gtg ctg act cag agc cca gac tct ctg tct gtg      96
Ser Arg Gly Glu Ile Val Leu Thr Gln Ser Pro Asp Ser Leu Ser Val
                20                  25                  30 act cca ggc gag aga gtc acc atc acc tgc cgg gcc agt cag agc att     144
Thr Pro Gly Glu Arg Val Thr Ile Thr Cys Arg Ala Ser Gln Ser Ile
            35                  40                  45 ggt agt agc tta cac tgg tac cag cag aaa cca ggt cag tct cca aag     192
Gly Ser Ser Leu His Trp Tyr Gln Gln Lys Pro Gly Gln Ser Pro Lys
        50                  55                  60 ctt ctc atc aag tat gca tcc cag tcc ctc tca ggg gtc ccc tcg agg     240
Leu Leu Ile Lys Tyr Ala Ser Gln Ser Leu Ser Gly Val Pro Ser Arg
65                  70                  75                  80 ttc agt ggc agt gga tct ggg aca gat ttc acc ctc acc atc agt agc     288
Phe Ser Gly Ser Gly Ser Gly Thr Asp Phe Thr Leu Thr Ile Ser Ser
                85                  90                  95 ctc gag gct gaa gat gct gca gcg tat tac tgt cat cag agt agt cgt     336
Leu Glu Ala Glu Asp Ala Ala Ala Tyr Tyr Cys His Gln Ser Ser Arg
                100                 105                 110 tta cct cac act ttc ggc caa ggg acc aag gtg gag atc aaa cgt acg     384
Leu Pro His Thr Phe Gly Gln Gly Thr Lys Val Glu Ile Lys Arg Thr
            115                 120                 125
```

<210> SEQ ID NO 2
<211> LENGTH: 128
<212> TYPE: PRT
<213> ORGANISM: Artificial Sequence
<220> FEATURE:
<223> OTHER INFORMATION: Synthetic Construct

<400> SEQUENCE: 2

```
Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Asp Ser Leu Ser Val
                20                  25                  30

Thr Pro Gly Glu Arg Val Thr Ile Thr Cys Arg Ala Ser Gln Ser Ile
            35                  40                  45

Gly Ser Ser Leu His Trp Tyr Gln Gln Lys Pro Gly Gln Ser Pro Lys
        50                  55                  60

Leu Leu Ile Lys Tyr Ala Ser Gln Ser Leu Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Glu Ala Glu Asp Ala Ala Ala Tyr Tyr Cys His Gln Ser Ser Arg
                100                 105                 110
```

```
Leu Pro His Thr Phe Gly Gln Gly Thr Lys Val Glu Ile Lys Arg Thr
        115                 120                 125

<210> SEQ ID NO 3
<211> LENGTH: 384
<212> TYPE: DNA
<213> ORGANISM: Artificial Sequence
<220> FEATURE:
<223> OTHER INFORMATION: Modified 19D12/15H12 Light Chain-D
<220> FEATURE:
<221> NAME/KEY: CDS
<222> LOCATION: (1)..(384)

<400> SEQUENCE: 3 atg tcg cca tca caa ctc att ggg ttt ctg ctg ctc tgg gtt cca gcc      48
Met Ser Pro Ser Gln Leu Ile Gly Phe Leu Leu Leu Trp Val Pro Ala
1               5                   10                  15 tcc agg ggt gaa att gtg ctg act cag agc cca gac tct ctg tct gtg      96
Ser Arg Gly Glu Ile Val Leu Thr Gln Ser Pro Asp Ser Leu Ser Val
            20                  25                  30 act cca ggc gag aga gtc acc atc acc tgc cgg gcc agt cag agc att     144
Thr Pro Gly Glu Arg Val Thr Ile Thr Cys Arg Ala Ser Gln Ser Ile
        35                  40                  45 ggt agt agc tta cac tgg tac cag cag aaa cca ggt cag tct cca aag     192
Gly Ser Ser Leu His Trp Tyr Gln Gln Lys Pro Gly Gln Ser Pro Lys
    50                  55                  60 ctt ctc atc aag tat gca tcc cag tcc ctc tca ggg gtc ccc tcg agg     240
Leu Leu Ile Lys Tyr Ala Ser Gln Ser Leu Ser Gly Val Pro Ser Arg
65                  70                  75                  80 ttc agt ggc agt gga tct ggg aca gat ttc acc ctc acc atc agt agc     288
Phe Ser Gly Ser Gly Ser Gly Thr Asp Phe Thr Leu Thr Ile Ser Ser
                85                  90                  95 ctc gag gct gaa gat ttc gca gtg tat tac tgt cat cag agt agt cgt     336
Leu Glu Ala Glu Asp Phe Ala Val Tyr Tyr Cys His Gln Ser Ser Arg
            100                 105                 110 tta cct cac act ttc ggc caa ggg acc aag gtg gag atc aaa cgt acg     384
Leu Pro His Thr Phe Gly Gln Gly Thr Lys Val Glu Ile Lys Arg Thr
        115                 120                 125

<210> SEQ ID NO 4
<211> LENGTH: 128
<212> TYPE: PRT
<213> ORGANISM: Artificial Sequence
<220> FEATURE:
<223> OTHER INFORMATION: Synthetic Construct

<400> SEQUENCE: 4

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Asp Ser Leu Ser Val
            20                  25                  30

Thr Pro Gly Glu Arg Val Thr Ile Thr Cys Arg Ala Ser Gln Ser Ile
        35                  40                  45

Gly Ser Ser Leu His Trp Tyr Gln Gln Lys Pro Gly Gln Ser Pro Lys
    50                  55                  60

Leu Leu Ile Lys Tyr Ala Ser Gln Ser Leu Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Glu Ala Glu Asp Phe Ala Val Tyr Tyr Cys His Gln Ser Ser Arg
            100                 105                 110
```

Leu Pro His Thr Phe Gly Gln Gly Thr Lys Val Glu Ile Lys Arg Thr
        115                 120                 125

<210> SEQ ID NO 5
<211> LENGTH: 384
<212> TYPE: DNA
<213> ORGANISM: Artificial Sequence
<220> FEATURE:
<223> OTHER INFORMATION: Modified 19D12/15H12 Light Chain-E
<220> FEATURE:
<221> NAME/KEY: CDS
<222> LOCATION: (1)..(384)

<400> SEQUENCE: 5

```
atg tcg cca tca caa ctc att ggg ttt ctg ctg ctc tgg gtt cca gcc      48
Met Ser Pro Ser Gln Leu Ile Gly Phe Leu Leu Leu Trp Val Pro Ala
1               5                   10                  15 tcc agg ggt gaa att gtg ctg act cag agc cca ggt acc ctg tct gtg      96
Ser Arg Gly Glu Ile Val Leu Thr Gln Ser Pro Gly Thr Leu Ser Val
            20                  25                  30 tct cca ggc gag aga gcc acc ctc tcc tgc cgg gcc agt cag agc att     144
Ser Pro Gly Glu Arg Ala Thr Leu Ser Cys Arg Ala Ser Gln Ser Ile
        35                  40                  45 ggt agt agc tta cac tgg tac cag cag aaa cca ggt cag gct cca agg     192
Gly Ser Ser Leu His Trp Tyr Gln Gln Lys Pro Gly Gln Ala Pro Arg
    50                  55                  60 ctt ctc atc aag tat gca tcc cag tcc ctc tca ggg atc ccc gat agg     240
Leu Leu Ile Lys Tyr Ala Ser Gln Ser Leu Ser Gly Ile Pro Asp Arg
65                  70                  75                  80 ttc agt ggc agt gga tct ggg aca gat ttc acc ctc acc atc agt aga     288
Phe Ser Gly Ser Gly Ser Gly Thr Asp Phe Thr Leu Thr Ile Ser Arg
                85                  90                  95 ctg gag cct gaa gat gct gca gcg tat tac tgt cat cag agt agt cgt     336
Leu Glu Pro Glu Asp Ala Ala Ala Tyr Tyr Cys His Gln Ser Ser Arg
            100                 105                 110 tta cct cac act ttc ggc caa ggg acc aag gtg gag atc aaa cgt aca     384
Leu Pro His Thr Phe Gly Gln Gly Thr Lys Val Glu Ile Lys Arg Thr
        115                 120                 125
```

<210> SEQ ID NO 6
<211> LENGTH: 128
<212> TYPE: PRT
<213> ORGANISM: Artificial Sequence
<220> FEATURE:
<223> OTHER INFORMATION: Synthetic Construct

<400> SEQUENCE: 6

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Gly Thr Leu Ser Val
            20                  25                  30

Ser Pro Gly Glu Arg Ala Thr Leu Ser Cys Arg Ala Ser Gln Ser Ile
        35                  40                  45

Gly Ser Ser Leu His Trp Tyr Gln Gln Lys Pro Gly Gln Ala Pro Arg
    50                  55                  60

Leu Leu Ile Lys Tyr Ala Ser Gln Ser Leu Ser Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Ala Ala Ala Tyr Tyr Cys His Gln Ser Ser Arg
            100                 105                 110

Leu Pro His Thr Phe Gly Gln Gly Thr Lys Val Glu Ile Lys Arg Thr
        115                 120                 125

<210> SEQ ID NO 7
<211> LENGTH: 384
<212> TYPE: DNA
<213> ORGANISM: Artificial Sequence
<220> FEATURE:
<223> OTHER INFORMATION: 19D12/15H12 Light Chain-F
<220> FEATURE:
<221> NAME/KEY: CDS
<222> LOCATION: (1)..(384)

<400> SEQUENCE: 7

```
atg tcg cca tca caa ctc att ggg ttt ctg ctg ctc tgg gtt cca gcc      48
Met Ser Pro Ser Gln Leu Ile Gly Phe Leu Leu Leu Trp Val Pro Ala
1               5                   10                  15 tcc agg ggt gaa att gtg ctg act cag agc cca ggt acc ctg tct gtg      96
Ser Arg Gly Glu Ile Val Leu Thr Gln Ser Pro Gly Thr Leu Ser Val
            20                  25                  30 tct cca ggc gag aga gcc acc ctc tcc tgc cgg gcc agt cag agc att     144
Ser Pro Gly Glu Arg Ala Thr Leu Ser Cys Arg Ala Ser Gln Ser Ile
        35                  40                  45 ggt agt agc tta cac tgg tac cag cag aaa cca ggt cag gct cca agg     192
Gly Ser Ser Leu His Trp Tyr Gln Gln Lys Pro Gly Gln Ala Pro Arg
    50                  55                  60 ctt ctc atc aag tat gca tcc cag tcc ctc tca ggg atc ccc gat agg     240
Leu Leu Ile Lys Tyr Ala Ser Gln Ser Leu Ser Gly Ile Pro Asp Arg
65                  70                  75                  80 ttc agt ggc agt gga tct ggg aca gat ttc acc ctc acc atc agt aga     288
Phe Ser Gly Ser Gly Ser Gly Thr Asp Phe Thr Leu Thr Ile Ser Arg
                85                  90                  95 ctg gag cct gaa gat ttc gca gtg tat tac tgt cat cag agt agt cgt     336
Leu Glu Pro Glu Asp Phe Ala Val Tyr Tyr Cys His Gln Ser Ser Arg
            100                 105                 110 tta cct cac act ttc ggc caa ggg acc aag gtg gag atc aaa cgt aca     384
Leu Pro His Thr Phe Gly Gln Gly Thr Lys Val Glu Ile Lys Arg Thr
        115                 120                 125
```

<210> SEQ ID NO 8
<211> LENGTH: 128
<212> TYPE: PRT
<213> ORGANISM: Artificial Sequence
<220> FEATURE:
<223> OTHER INFORMATION: Synthetic Construct

<400> SEQUENCE: 8

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Gly Thr Leu Ser Val
            20                  25                  30

Ser Pro Gly Glu Arg Ala Thr Leu Ser Cys Arg Ala Ser Gln Ser Ile
        35                  40                  45

Gly Ser Ser Leu His Trp Tyr Gln Gln Lys Pro Gly Gln Ala Pro Arg
    50                  55                  60

Leu Leu Ile Lys Tyr Ala Ser Gln Ser Leu Ser Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys His Gln Ser Ser Arg
            100                 105                 110

Leu Pro His Thr Phe Gly Gln Gly Thr Lys Val Glu Ile Lys Arg Thr
        115                 120                 125

<210> SEQ ID NO 9
<211> LENGTH: 411
<212> TYPE: DNA
<213> ORGANISM: Artificial Sequence
<220> FEATURE:
<223> OTHER INFORMATION: 19D12/15H12 heavy chain-A
<220> FEATURE:
<221> NAME/KEY: CDS
<222> LOCATION: (1)..(411)

<400> SEQUENCE: 9

```
atg gag ttt ggg ctg agc tgg gtt ttc ctt gtt gct ata tta aaa ggt     48
Met Glu Phe Gly Leu Ser Trp Val Phe Leu Val Ala Ile Leu Lys Gly
1               5                   10                  15 gtc cag tgt gag gtt cag ctg gtg cag tct ggg gga ggc ttg gta aag     96
Val Gln Cys Glu Val Gln Leu Val Gln Ser Gly Gly Gly Leu Val Lys
            20                  25                  30 cct ggg ggg tcc ctg aga ctc tcc tgt gca gcc tct gga ttc acc ttc    144
Pro Gly Gly Ser Leu Arg Leu Ser Cys Ala Ala Ser Gly Phe Thr Phe
        35                  40                  45 agt agc ttt gct atg cac tgg gtt cgc cag gct cca gga aaa ggt ctg    192
Ser Ser Phe Ala Met His Trp Val Arg Gln Ala Pro Gly Lys Gly Leu
    50                  55                  60 gag tgg ata tca gtt att gat act cgt ggt gcc aca tac tat gca gac    240
Glu Trp Ile Ser Val Ile Asp Thr Arg Gly Ala Thr Tyr Tyr Ala Asp
65                  70                  75                  80 tcc gtg aag ggc cga ttc acc atc tcc aga gac aat gcc aag aac tcc    288
Ser Val Lys Gly Arg Phe Thr Ile Ser Arg Asp Asn Ala Lys Asn Ser
                85                  90                  95 ttg tat ctt caa atg aac agc ctg aga gcc gag gac act gct gtg tat    336
Leu Tyr Leu Gln Met Asn Ser Leu Arg Ala Glu Asp Thr Ala Val Tyr
            100                 105                 110 tac tgt gca aga ctg ggg aac ttc tac tac ggt atg gac gtc tgg ggc    384
Tyr Cys Ala Arg Leu Gly Asn Phe Tyr Tyr Gly Met Asp Val Trp Gly
        115                 120                 125 caa ggg acc acg gtc acc gtc tcc tca                                411
Gln Gly Thr Thr Val Thr Val Ser Ser
    130                 135
```

<210> SEQ ID NO 10
<211> LENGTH: 137
<212> TYPE: PRT
<213> ORGANISM: Artificial Sequence
<220> FEATURE:
<223> OTHER INFORMATION: Synthetic Construct

<400> SEQUENCE: 10

Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
    50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser

```
                            85                  90                  95
Leu Tyr Leu Gln Met Asn Ser Leu Arg Ala Glu Asp Thr Ala Val Tyr
                100                 105                 110
Tyr Cys Ala Arg Leu Gly Asn Phe Tyr Tyr Gly Met Asp Val Trp Gly
            115                 120                 125
Gln Gly Thr Thr Val Thr Val Ser Ser
        130                 135

<210> SEQ ID NO 11
<211> LENGTH: 411
<212> TYPE: DNA
<213> ORGANISM: Artificial Sequence
<220> FEATURE:
<223> OTHER INFORMATION: Modified 19D12/15H12 heavy chain-B
<220> FEATURE:
<221> NAME/KEY: CDS
<222> LOCATION: (1)..(411)

<400> SEQUENCE: 11 atg gag ttt ggg ctg agc tgg gtt ttc ctt gtt gct ata tta aaa ggt      48
Met Glu Phe Gly Leu Ser Trp Val Phe Leu Val Ala Ile Leu Lys Gly
1               5                   10                  15 gtc cag tgt gag gtt cag ctg gtg cag tct ggg gga ggc ttg gta cag      96
Val Gln Cys Glu Val Gln Leu Val Gln Ser Gly Gly Gly Leu Val Gln
                20                  25                  30 ccc ggg ggg tcc ctg aga ctc tcc tgt gca gcc tct gga ttc acc ttc     144
Pro Gly Gly Ser Leu Arg Leu Ser Cys Ala Ala Ser Gly Phe Thr Phe
            35                  40                  45 agt agc ttt gct atg cac tgg gtt cgc cag gct cca gga aaa ggt ctg     192
Ser Ser Phe Ala Met His Trp Val Arg Gln Ala Pro Gly Lys Gly Leu
        50                  55                  60 gag tgg ata tca gtt att gat act cgt ggt gcc aca tac tat gca gac     240
Glu Trp Ile Ser Val Ile Asp Thr Arg Gly Ala Thr Tyr Tyr Ala Asp
65                  70                  75                  80 tcc gtg aag ggc cga ttc acc atc tcc aga gac aat gcc aag aac tcc     288
Ser Val Lys Gly Arg Phe Thr Ile Ser Arg Asp Asn Ala Lys Asn Ser
                85                  90                  95 ttg tat ctt caa atg aac agc ctg aga gcc gag gac act gct gtg tat     336
Leu Tyr Leu Gln Met Asn Ser Leu Arg Ala Glu Asp Thr Ala Val Tyr
                100                 105                 110 tac tgt gca aga ctg ggg aac ttc tac tac ggt atg gac gtc tgg ggc     384
Tyr Cys Ala Arg Leu Gly Asn Phe Tyr Tyr Gly Met Asp Val Trp Gly
            115                 120                 125 caa ggg acc acg gtc acc gtc tcc tca                                 411
Gln Gly Thr Thr Val Thr Val Ser Ser
        130                 135

<210> SEQ ID NO 12
<211> LENGTH: 137
<212> TYPE: PRT
<213> ORGANISM: Artificial Sequence
<220> FEATURE:
<223> OTHER INFORMATION: Synthetic Construct

<400> SEQUENCE: 12

Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val Gln
                20                  25                  30

Pro Gly Gly Ser Leu Arg Leu Ser Cys Ala Ala Ser Gly Phe Thr Phe
            35                  40                  45
```

Ser Ser Phe Ala Met His Trp Val Arg Gln Ala Pro Gly Lys Gly Leu
    50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
    130                 135

<210> SEQ ID NO 13
<211> LENGTH: 174
<212> TYPE: PRT
<213> ORGANISM: Artificial Sequence
<220> FEATURE:
<223> OTHER INFORMATION: immunoglobulin heavy chain variable region

<400> SEQUENCE: 13

Gly Arg Leu Gly Gln Ala Trp Arg Ser Leu Arg Leu Ser Cys Ala Ala
1               5                   10                  15

Ser Gly Phe Thr Phe Ser Asp Tyr Tyr Met Ser Trp Ile Arg Gln Ala
            20                  25                  30

Pro Gly Lys Gly Leu Glu Trp Val Ser Tyr Ile Ser Ser Gly Ser
        35                  40                  45

Thr Arg Asp Tyr Ala Asp Ser Val Lys Gly Arg Phe Thr Ile Ser Arg
    50                  55                  60

Asp Asn Ala Lys Asn Ser Leu Tyr Leu Gln Met Asn Ser Leu Arg Ala
65                  70                  75                  80

Glu Asp Thr Ala Val Tyr Tyr Cys Val Arg Asp Gly Val Glu Thr Thr
                85                  90                  95

Phe Tyr Tyr Tyr Tyr Gly Met Asp Val Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ser Cys Ala
                165                 170

<210> SEQ ID NO 14
<211> LENGTH: 124
<212> TYPE: PRT
<213> ORGANISM: Artificial Sequence
<220> FEATURE:
<223> OTHER INFORMATION: immunoglobulin heavy chain variable region

<400> SEQUENCE: 14

Val Gln Leu Leu Glu Ser Gly Gly Gly Leu Val Gln Pro Gly Gly Ser
1               5                   10                  15

Leu Arg Leu Ser Cys Thr Ala Ser Gly Phe Thr Phe Ser Ser Tyr Ala
            20                  25                  30

Met Asn Trp Val Arg Gln Ala Pro Gly Lys Gly Leu Glu Trp Val Ser
        35                  40                  45

Ala Ile Ser Gly Ser Gly Gly Thr Thr Phe Tyr Ala Asp Ser Val Lys
            50                  55                  60

Gly Arg Phe Thr Ile Ser Arg Asp Asn Ser Arg Thr Thr Leu Tyr Leu
 65                  70                  75                  80

Gln Met Asn Ser Leu Arg Ala Glu Asp Thr Ala Val Tyr Tyr Cys Ala
                 85                  90                  95

Lys Asp Leu Gly Trp Ser Asp Ser Tyr Tyr Tyr Tyr Gly Met Asp
             100                 105                 110

Val Trp Gly Gln Gly Thr Thr Val Thr Val Ser Ser
         115                 120

<210> SEQ ID NO 15
<211> LENGTH: 112
<212> TYPE: PRT
<213> ORGANISM: Artificial Sequence
<220> FEATURE:
<223> OTHER INFORMATION: immunoglobulin heavy chain variable region

<400> SEQUENCE: 15

Gly Pro Gly Leu Val Lys Pro Ser Glu Thr Leu Ser Leu Thr Cys Thr
1               5                  10                  15

Val Ser Gly Gly Ser Ile Ser Asn Tyr Tyr Trp Ser Trp Ile Arg Gln
             20                  25                  30

Pro Ala Gly Lys Gly Leu Glu Trp Ile Gly Arg Ile Tyr Thr Ser Gly
         35                  40                  45

Ser Pro Asn Tyr Asn Pro Ser Leu Lys Ser Arg Val Thr Met Ser Val
     50                  55                  60

Asp Thr Ser Lys Asn Gln Phe Ser Leu Lys Leu Asn Ser Val Thr Ala
 65                  70                  75                  80

Ala Asp Thr Ala Val Tyr Tyr Cys Ala Val Thr Ile Phe Gly Val Val
                 85                  90                  95

Ile Ile Phe Asp Tyr Trp Gly Gln Gly Thr Leu Val Thr Val Ser Ser
             100                 105                 110

<210> SEQ ID NO 16
<211> LENGTH: 125
<212> TYPE: PRT
<213> ORGANISM: Artificial Sequence
<220> FEATURE:
<223> OTHER INFORMATION: immunoglobulin heavy chain variable region

<400> SEQUENCE: 16

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ile Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Leu Gly Tyr Gly Asp Phe Tyr Tyr Tyr Tyr Gly Met
             100                 105                 110

Asp Val Trp Gly Gln Gly Thr Thr Val Thr Val Ser Ser

```
              115                 120                 125

<210> SEQ ID NO 17
<211> LENGTH: 113
<212> TYPE: PRT
<213> ORGANISM: Artificial Sequence
<220> FEATURE:
<223> OTHER INFORMATION: immunoglobulin heavy chain variable region

<400> SEQUENCE: 17

Pro Gly Leu Val Lys Pro Ser Glu Thr Leu Ser Leu Thr Cys Thr Val
1               5                   10                  15

Ser Gly Gly Ser Ile Ser Ser Tyr Tyr Trp Ser Trp Ile Arg Gln Pro
            20                  25                  30

Pro Gly Lys Gly Leu Glu Trp Ile Gly Tyr Ile Tyr Tyr Ser Gly Ser
        35                  40                  45

Thr Asn Tyr Asn Pro Ser Leu Lys Ser Arg Val Thr Ile Ser Val Asp
    50                  55                  60

Thr Ser Lys Asn Gln Phe Ser Leu Lys Leu Ser Ser Val Thr Ala Ala
65                  70                  75                  80

Asp Thr Ala Val Tyr Tyr Cys Ala Arg Thr Tyr Ser Ser Ser Phe Tyr
                85                  90                  95

Tyr Tyr Gly Met Asp Val Trp Gly Gln Gly Thr Thr Val Thr Val Ser
            100                 105                 110

Ser

<210> SEQ ID NO 18
<211> LENGTH: 122
<212> TYPE: PRT
<213> ORGANISM: Artificial Sequence
<220> FEATURE:
<223> OTHER INFORMATION: immunoglobulin heavy chain variable region

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Thr Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Thr Thr Val Ile Met Ser Trp Phe Asp Pro Trp
            100                 105                 110

Gly Gln Gly Thr Leu Val Thr Val Ser Ser
        115                 120

<210> SEQ ID NO 19
<211> LENGTH: 136
<212> TYPE: PRT
<213> ORGANISM: Artificial Sequence
<220> FEATURE:
<223> OTHER INFORMATION: immunoglobulin light chain variable region

<400> SEQUENCE: 19
```

```
Ala Ser Val Gly Asp Arg Val Thr Phe Thr Cys Arg Ala Ser Gln Asp
1               5                   10                  15

Ile Arg Arg Asp Leu Gly Trp Tyr Gln Gln Lys Pro Gly Lys Ala Pro
            20                  25                  30

Lys Arg Leu Ile Tyr Ala Ala Ser Arg Leu Gln Ser Gly Val Pro Ser
        35                  40                  45

Arg Phe Ser Gly Ser Gly Ser Gly Thr Glu Phe Thr Leu Thr Ile Ser
    50                  55                  60

Ser Leu Gln Pro Glu Asp Phe Ala Thr Tyr Tyr Cys Leu Gln His Asn
65              70                  75                  80

Asn Tyr Pro Arg Thr Phe Gly Gln Gly Thr Glu Val Glu Ile Ile Arg
            85                  90                  95

Thr Val Ala Ala Pro Ser Val Phe Ile Phe Pro Pro Ser Asp Glu Gln
            100                 105                 110

Leu Lys Ser Gly Thr Ala Ser Val Val Cys Leu Leu Asn Asn Phe Tyr
        115                 120                 125

Pro Arg Glu Ala Lys Val Gln Trp
        130                 135

<210> SEQ ID NO 20
<211> LENGTH: 107
<212> TYPE: PRT
<213> ORGANISM: Artificial Sequence
<220> FEATURE:
<223> OTHER INFORMATION: immunoglobulin light chain variable region

<400> SEQUENCE: 20

Asp Ile Gln Met Thr Gln Phe Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu His Arg Gly Val Pro Ser Arg Phe Ser Gly
    50                  55                  60

Ser Gly Ser Gly Thr Glu Phe Thr Leu Thr Ile Ser Ser Leu Gln Pro
65              70                  75                  80

Glu Asp Phe Ala Thr Tyr Tyr Cys Leu Gln His Asn Ser Tyr Pro Cys
            85                  90                  95

Ser Phe Gly Gln Gly Thr Lys Leu Glu Ile Lys
            100                 105

<210> SEQ ID NO 21
<211> LENGTH: 100
<212> TYPE: PRT
<213> ORGANISM: Artificial Sequence
<220> FEATURE:
<223> OTHER INFORMATION: immunoglobulin light chain variable region

<400> SEQUENCE: 21

Ser Ser Leu Ser Ala Ser Val Gly Asp Arg Val Thr Phe Thr Cys Arg
1               5                   10                  15

Ala Ser Gln Asp Ile Arg Arg Asp Leu Gly Trp Tyr Gln Gln Lys Pro
            20                  25                  30

Gly Lys Ala Pro Lys Arg Leu Ile Tyr Ala Ala Ser Arg Leu Gln Ser
        35                  40                  45

Gly Val Pro Ser Arg Phe Ser Gly Ser Gly Ser Gly Thr Glu Phe Thr
    50                  55                  60
```

```
Leu Thr Ile Ser Ser Leu Gln Pro Glu Asp Phe Ala Thr Tyr Tyr Cys
 65                  70                  75                  80

Leu Gln His Asn Asn Tyr Pro Arg Thr Phe Gly Gln Gly Thr Glu Val
                 85                  90                  95

Glu Ile Ile Arg
            100

<210> SEQ ID NO 22
<211> LENGTH: 107
<212> TYPE: PRT
<213> ORGANISM: Artificial Sequence
<220> FEATURE:
<223> OTHER INFORMATION: immunoglobulin light chain variable region

<400> SEQUENCE: 22

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Ser Asp
                 20                  25                  30

Leu Gly Trp Phe Gln Gln Lys Pro Gly Lys Ala Pro Lys Arg Leu Ile
             35                  40                  45

Tyr Ala Ala Ser Lys Leu His Arg Gly Val Pro Ser Arg Phe Ser Gly
 50                  55                  60

Ser Gly Ser Gly Thr Glu Phe Thr Leu Thr Ile Ser Arg Leu Gln Pro
 65                  70                  75                  80

Glu Asp Phe Ala Thr Tyr Tyr Cys Leu Gln His Asn Ser Tyr Pro Leu
                 85                  90                  95

Thr Phe Gly Gly Gly Thr Lys Val Glu Ile Lys
            100                 105

<210> SEQ ID NO 23
<211> LENGTH: 92
<212> TYPE: PRT
<213> ORGANISM: Artificial Sequence
<220> FEATURE:
<223> OTHER INFORMATION: immunoglobulin light chain variable region

<400> SEQUENCE: 23

Gly Asp Arg Val Thr Ile Thr Cys Arg Ala Ser Gln Ser Ile Ser Thr
  1               5                  10                  15

Phe Leu Asn Trp Tyr Gln Gln Lys Pro Gly Lys Ala Pro Lys Leu Leu
                 20                  25                  30

Ile His Val Ala Ser Ser Leu Gln Gly Gly Val Pro Ser Arg Phe Ser
             35                  40                  45

Gly Ser Gly Ser Gly Thr Asp Phe Thr Leu Thr Ile Ser Ser Leu Gln
         50                  55                  60

Pro Glu Asp Phe Ala Thr Tyr Tyr Cys Gln Gln Ser Tyr Asn Ala Pro
 65                  70                  75                  80

Leu Thr Phe Gly Gly Gly Thr Lys Val Glu Ile Lys
                 85                  90

<210> SEQ ID NO 24
<211> LENGTH: 91
<212> TYPE: PRT
<213> ORGANISM: Artificial Sequence
<220> FEATURE:
<223> OTHER INFORMATION: immunoglobulin light chain variable region

<400> SEQUENCE: 24
```

```
Arg Ala Thr Leu Ser Cys Arg Ala Ser Gln Ser Val Arg Gly Arg Tyr
1               5                   10                  15

Leu Ala Trp Tyr Gln Gln Lys Pro Gly Gln Ala Pro Arg Leu Leu Ile
            20                  25                  30

Tyr Gly Ala Ser Ser Arg Ala Thr Gly Ile Pro Asp Arg Phe Ser Gly
        35                  40                  45

Ser Gly Ser Gly Thr Asp Phe Thr Leu Thr Ile Ser Arg Leu Glu Pro
    50                  55                  60

Glu Asp Phe Ala Val Phe Tyr Cys Gln Gln Tyr Gly Ser Ser Pro Arg
65              70                  75                  80

Thr Phe Gly Gln Gly Thr Lys Val Glu Ile Lys
                85                  90
```

<210> SEQ ID NO 25
<211> LENGTH: 236
<212> TYPE: PRT
<213> ORGANISM: Artificial Sequence
<220> FEATURE:
<223> OTHER INFORMATION: light chain immunoglobulin

<400> SEQUENCE: 25

```
Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
    50                  55                  60

Ala Pro Lys Arg Leu Ile Tyr Ala Ala Ser Ser Leu Gln Ser Gly Val
65              70                  75                  80

Pro Ser Arg Phe Ser Gly Ser Gly Ser Gly Thr Glu Phe Thr Leu Thr
            85                  90                  95

Ile Ser Ser Leu Gln Pro Glu Asp Phe Ala Thr Tyr Tyr Cys Leu Gln
            100                 105                 110

His Asn Ser Tyr Pro Trp Thr Phe Gly Gln Gly Thr Lys Val Glu Ile
            115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 26
<211> LENGTH: 236
<212> TYPE: PRT
<213> ORGANISM: Artificial Sequence
<220> FEATURE:

<223> OTHER INFORMATION: light chain immunoglobulin

<400> SEQUENCE: 26

```
Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Phe Thr Cys Arg Ala Ser
        35                  40                  45

Gln Asp Ile Arg Arg Asp Leu Gly Trp Tyr Gln Gln Lys Pro Gly Lys
    50                  55                  60

Ala Pro Lys Arg Leu Ile Tyr Ala Ala Ser Arg Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

His Asn Asn Tyr Pro Arg Thr Phe Gly Gln Gly Thr Glu Val Glu Ile
        115                 120                 125

Ile Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 27
<211> LENGTH: 236
<212> TYPE: PRT
<213> ORGANISM: Artificial Sequence
<220> FEATURE:
<223> OTHER INFORMATION: light chain immunoglobulin

<400> SEQUENCE: 27

```
Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
    50                  55                  60

Ala Pro Lys Arg Leu Ile Tyr Ala Ala Ser Ser Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110
```

His Asn Ser Tyr Pro Tyr Thr Phe Gly Gln Gly Thr Lys Leu Glu Ile
            115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 28
<211> LENGTH: 236
<212> TYPE: PRT
<213> ORGANISM: Artificial Sequence
<220> FEATURE:
<223> OTHER INFORMATION: light chain immunoglobulin

<400> SEQUENCE: 28

Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Phe Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
    50                  55                  60

Ala Pro Lys Arg Leu Ile Tyr Ala Ala Ser Arg Leu His Arg Gly Val
65                  70                  75                  80

Pro Ser Arg Phe Ser Gly Ser Gly Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

His Asn Ser Tyr Pro Cys Ser Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 29
<211> LENGTH: 473
<212> TYPE: PRT
<213> ORGANISM: Artificial Sequence
<220> FEATURE:
<223> OTHER INFORMATION: heavy chain immunoglobulin

<400> SEQUENCE: 29

```
Met Glu Phe Gly Leu Ser Trp Val Phe Leu Val Ala Ile Ile Lys Gly
1               5                   10                  15

Val Gln Cys Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Tyr Tyr Met Ser Trp Ile Arg Gln Ala Pro Gly Lys Gly Leu
    50                  55                  60

Glu Trp Val Ser Tyr Ile Ser Ser Gly Ser Thr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Val Leu Arg Phe Leu Glu Trp Leu Leu Tyr Tyr
        115                 120                 125

Tyr Tyr Tyr Tyr Gly Met Asp Val Trp Gly Gln Gly Thr Thr Val Thr
    130                 135                 140

Val Ser Ser Ala Ser Thr Lys Gly Pro Ser Val Phe Pro Leu Ala Pro
145                 150                 155                 160

Cys Ser Arg Ser Thr Ser Glu Ser Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Asn Phe Gly
    210                 215                 220

Thr Gln Thr Tyr Thr Cys Asn Val Asp His Lys Pro Ser Asn Thr Lys
225                 230                 235                 240

Val Asp Lys Thr Val Glu Arg Lys Cys Cys Val Glu Cys Pro Pro Cys
                245                 250                 255

Pro Ala Pro Pro Val Ala Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Gln Phe Asn Trp Tyr
    290                 295                 300

Val Asp Gly Val Glu Val His Asn Ala Lys Thr Lys Pro Arg Glu Glu
305                 310                 315                 320

Gln Phe Asn Ser Thr Phe Arg Val Val Ser Val Leu Thr Val Val His
                325                 330                 335

Gln Asp Trp Leu Asn Gly Lys Glu Tyr Lys Cys Lys Val Ser Asn Lys
            340                 345                 350

Gly Leu Pro Ala Pro Ile Glu Lys Thr Ile Ser Lys Thr Lys Gly Gln
        355                 360                 365
```

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
            405                 410                 415

Tyr Lys Thr Thr Pro Pro Met Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 30
<211> LENGTH: 470
<212> TYPE: PRT
<213> ORGANISM: Artificial Sequence
<220> FEATURE:
<223> OTHER INFORMATION: heavy chain immunoglobulin

<400> SEQUENCE: 30

Met Glu Phe Gly Leu Ser Trp Val Phe Leu Val Ala Ile Ile Lys Gly
1               5                   10                  15

Val Gln Cys Gln Ala Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Tyr Tyr Met Ser Trp Ile Arg Gln Ala Pro Gly Lys Gly Leu
    50                  55                  60

Glu Trp Val Ser Tyr Ile Ser Ser Ser Gly Ser Thr Arg Asp Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Val Arg Asp Gly Val Glu Thr Thr Phe Tyr Tyr Tyr Tyr
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Gln Phe Asn Trp Tyr Val Asp Gly
            290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
            355                 360                 365

Pro Gln Val Tyr Thr Leu Pro Pro Ser Arg Glu Glu Met Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
            450                 455                 460

Ser Leu Ser Pro Gly Lys
465                 470

<210> SEQ ID NO 31
<211> LENGTH: 470
<212> TYPE: PRT
<213> ORGANISM: Artificial Sequence
<220> FEATURE:
<223> OTHER INFORMATION: heavy chain immunoglobulin

<400> SEQUENCE: 31

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Ala Ile Ser Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Gly Tyr Ser Ser Gly Trp Tyr Tyr Tyr Tyr Tyr
            115                 120                 125

Tyr Gly Met Asp Val Trp Gly Gln Gly Thr Thr Val Thr Val Ser Ser
            130                 135                 140

```
Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
            165                 170                 175

Phe Pro Glu Pro Val Thr Val Ser Trp Asn Ser Gly Ala Leu Thr Ser
        180                 185                 190

Gly Val His Thr Phe Pro Ala Val Leu Gln Ser Ser Gly Leu Tyr Ser
    195                 200                 205

Leu Ser Ser Val Val Thr Val Pro Ser Ser Asn Phe Gly Thr Gln Thr
210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
            245                 250                 255

Pro Val Ala Gly Pro Ser Val Phe Leu Phe Pro Pro Lys Pro Lys Asp
        260                 265                 270

Thr Leu Met Ile Ser Arg Thr Pro Glu Val Thr Cys Val Val Val Asp
    275                 280                 285

Val Ser His Glu Asp Pro Glu Val Gln Phe Asn Trp Tyr Val Asp Gly
290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
            325                 330                 335

Leu Asn Gly Lys Glu Tyr Lys Cys Lys Val Ser Asn Lys Gly Leu Pro
        340                 345                 350

Ala Pro Ile Glu Lys Thr Ile Ser Lys Thr Lys Gly Gln Pro Arg Glu
    355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Met Leu Asp Ser Asp Gly Ser Phe Phe Leu Tyr Ser Lys
        420                 425                 430

Leu Thr Val Asp Lys Ser Arg Trp Gln Gln Gly Asn Val Phe Ser Cys
    435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 32
<211> LENGTH: 470
<212> TYPE: PRT
<213> ORGANISM: Artificial Sequence
<220> FEATURE:
<223> OTHER INFORMATION: heavy chain immunoglobulin

<400> SEQUENCE: 32

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30
```

-continued

Pro Gly Gly Ser Leu Arg Leu Ser Cys Thr Ala Ser Gly Phe Thr Phe
            35                  40                  45

Ser Ser Tyr Ala Met Asn Trp Val Arg Gln Ala Pro Gly Lys Gly Leu
    50                  55                  60

Glu Trp Val Ser Ala Ile Ser Gly Ser Gly Gly Thr Thr Phe Tyr Ala
65                  70                  75                  80

Asp Ser Val Lys Gly Arg Phe Thr Ile Ser Arg Asp Asn Ser Arg Thr
                85                  90                  95

Thr Leu Tyr Leu Gln Met Asn Ser Leu Arg Ala Glu Asp Thr Ala Val
            100                 105                 110

Tyr Tyr Cys Ala Lys Asp Leu Gly Trp Ser Asp Ser Tyr Tyr Tyr Tyr
            115                 120                 125

Tyr Gly Met Asp Val Trp Gly Gln Gly Thr Thr Val Thr Val Ser Ser
            130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
            195                 200                 205

Leu Ser Ser Val Val Thr Val Pro Ser Ser Asn Phe Gly Thr Gln Thr
            210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Gln Phe Asn Trp Tyr Val Asp Gly
290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
            355                 360                 365

Pro Gln Val Tyr Thr Leu Pro Pro Ser Arg Glu Glu Met Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

```
Ser Val Met His Glu Ala Leu His Asn His Tyr Thr Gln Lys Ser Leu
    450                 455                 460

Ser Leu Ser Pro Gly Lys
465                 470

<210> SEQ ID NO 33
<211> LENGTH: 470
<212> TYPE: PRT
<213> ORGANISM: Artificial Sequence
<220> FEATURE:
<223> OTHER INFORMATION: immunoglobulin heavy chain of 2.12.1 fx

<400> SEQUENCE: 33

Met Glu Phe Gly Leu Ser Trp Val Phe Leu Val Ala Ile Ile Lys Gly
1               5                   10                  15

Val Gln Cys Gln Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Asp Tyr Tyr Met Ser Trp Ile Arg Gln Ala Pro Gly Lys Gly Leu
    50                  55                  60

Glu Trp Val Ser Tyr Ile Ser Ser Ser Gly Ser Thr Arg Asp Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Asp Gly Val Glu Thr Thr Phe Tyr Tyr Tyr Tyr
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val His Gln Asp Trp
                325                 330                 335
```

```
Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
            355                 360                 365

Pro Gln Val Tyr Thr Leu Pro Pro Ser Arg Glu Glu Met Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
            450                 455                 460

Ser Leu Ser Pro Gly Lys
465                 470

<210> SEQ ID NO 34
<211> LENGTH: 125
<212> TYPE: PRT
<213> ORGANISM: Artificial Sequence
<220> FEATURE:
<223> OTHER INFORMATION: mature immunoglobulin heavy chain variable
      region of 2.12.1 fx

<400> SEQUENCE: 34

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Arg Asp Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Gly Val Glu Thr Thr Phe Tyr Tyr Tyr Tyr Gly Met
            100                 105                 110

Asp Val Trp Gly Gln Gly Thr Thr Val Thr Val Ser Ser
        115                 120                 125

<210> SEQ ID NO 35
<211> LENGTH: 236
<212> TYPE: PRT
<213> ORGANISM: Artificial Sequence
<220> FEATURE:
<223> OTHER INFORMATION: immunoglobulin light chain of 2.12.1 fx

<400> SEQUENCE: 35

Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
```

```
                  35                  40                  45
Gln Asp Ile Arg Arg Asp Leu Gly Trp Tyr Gln Gln Lys Pro Gly Lys
 50                  55                  60

Ala Pro Lys Arg Leu Ile Tyr Ala Ala Ser Arg Leu Gln Ser Gly Val
65                  70                  75                  80

Pro Ser Arg Phe Ser Gly Ser Gly Ser Gly Thr Glu Phe Thr Leu Thr
                 85                  90                  95

Ile Ser Ser Leu Gln Pro Glu Asp Phe Ala Thr Tyr Tyr Cys Leu Gln
             100                 105                 110

His Asn Asn Tyr Pro Arg Thr Phe Gly Gln Gly Thr Lys Val Glu Ile
             115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 36
<211> LENGTH: 108
<212> TYPE: PRT
<213> ORGANISM: Artificial Sequence
<220> FEATURE:
<223> OTHER INFORMATION: mature immunoglobulin light chain variable
      region of 2.12.1 fx

<400> SEQUENCE: 36

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Asp Ile Arg Arg Asp
             20                  25                  30

Leu Gly Trp Tyr Gln Gln Lys Pro Gly Lys Ala Pro Lys Arg Leu Ile
         35                  40                  45

Tyr Ala Ala Ser Arg Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Arg
                 85                  90                  95

Thr Phe Gly Gln Gly Thr Lys Val Glu Ile Lys Arg
            100                 105

<210> SEQ ID NO 37
<211> LENGTH: 112
<212> TYPE: PRT
<213> ORGANISM: Artificial Sequence
<220> FEATURE:
<223> OTHER INFORMATION: humanized 7C10 immunoglobulin light chain
      variable region; version 1
```

-continued

```
<400> SEQUENCE: 37

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Gln Trp Tyr Leu Gln Lys Pro Gly Gln Ser
        35                  40                  45

Pro Gln Leu Leu Ile Tyr Lys Val Ser Asn Arg Leu Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110

<210> SEQ ID NO 38
<211> LENGTH: 112
<212> TYPE: PRT
<213> ORGANISM: Artificial Sequence
<220> FEATURE:
<223> OTHER INFORMATION: humanized 7C10 immunoglobulin light chain
      variable region; version 2

<400> SEQUENCE: 38

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Gln Trp Tyr Leu Gln Lys Pro Gly Gln Ser
        35                  40                  45

Pro Gln Leu Leu Ile Tyr Lys Val Ser Asn Arg Leu Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110

<210> SEQ ID NO 39
<211> LENGTH: 117
<212> TYPE: PRT
<213> ORGANISM: Artificial Sequence
<220> FEATURE:
<223> OTHER INFORMATION: humanized 7C10 immunoglobulin heavy chain
      variable region; version 1

<400> SEQUENCE: 39

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Gly Gly
            20                  25                  30

Tyr Leu Trp Asn Trp Ile Arg Gln Pro Pro Gly Lys Gly Leu Glu Trp
        35                  40                  45

Met Gly Tyr Ile Ser Tyr Asp Gly Thr Asn Asn Tyr Lys Pro Ser Leu
    50                  55                  60

Lys Asp Arg Ile Thr Ile Ser Arg Asp Thr Ser Lys Asn Gln Phe Ser
```

```
                65                  70                  75                  80
Leu Lys Leu Ser Ser Val Thr Ala Ala Asp Thr Ala Val Tyr Tyr Cys
                    85                  90                  95

Ala Arg Tyr Gly Arg Val Phe Phe Asp Tyr Trp Gly Gln Gly Thr Leu
                100                 105                 110

Val Thr Val Ser Ser
        115

<210> SEQ ID NO 40
<211> LENGTH: 117
<212> TYPE: PRT
<213> ORGANISM: Artificial Sequence
<220> FEATURE:
<223> OTHER INFORMATION: humanized 7C10 immunoglobulin heavy chain
      variable region; version 2

<400> SEQUENCE: 40

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Gly Gly
                20                  25                  30

Tyr Leu Trp Asn Trp Ile Arg Gln Pro Pro Gly Lys Gly Leu Glu Trp
            35                  40                  45

Ile Gly Tyr Ile Ser Tyr Asp Gly Thr Asn Asn Tyr Lys Pro Ser Leu
    50                  55                  60

Lys Asp Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Tyr Gly Arg Val Phe Phe Asp Tyr Trp Gly Gln Gly Thr Leu
                100                 105                 110

Val Thr Val Ser Ser
        115

<210> SEQ ID NO 41
<211> LENGTH: 117
<212> TYPE: PRT
<213> ORGANISM: Artificial Sequence
<220> FEATURE:
<223> OTHER INFORMATION: humanized 7C10 immunoglobulin heavy chain
      variable region; version 3

<400> SEQUENCE: 41

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Gly Gly
                20                  25                  30

Tyr Leu Trp Asn Trp Ile Arg Gln Pro Pro Gly Lys Gly Leu Glu Trp
            35                  40                  45

Ile Gly Tyr Ile Ser Tyr Asp Gly Thr Asn Asn Tyr Lys Pro Ser Leu
    50                  55                  60

Lys Asp Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Tyr Gly Arg Val Phe Phe Asp Tyr Trp Gly Gln Gly Thr Leu
                100                 105                 110

Val Thr Val Ser Ser
```

```
<210> SEQ ID NO 42
<211> LENGTH: 130
<212> TYPE: PRT
<213> ORGANISM: Artificial Sequence
<220> FEATURE:
<223> OTHER INFORMATION: A12 immunoglobulin heavy chain variable region

<400> SEQUENCE: 42

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Leu Arg Phe Leu Glu Trp Ser Thr Gln Asp His Tyr
            100                 105                 110

Tyr Tyr Tyr Tyr Met Asp Val Trp Gly Lys Gly Thr Thr Val Thr Val
        115                 120                 125

Ser Ser
    130

<210> SEQ ID NO 43
<211> LENGTH: 109
<212> TYPE: PRT
<213> ORGANISM: Artificial Sequence
<220> FEATURE:
<223> OTHER INFORMATION: A12 immunoglobulin light chain variable region

<400> SEQUENCE: 43

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Asn Ser Asp Asn Arg
                85                  90                  95

Leu Ile Phe Gly Gly Gly Thr Lys Leu Thr Val Leu Ser
            100                 105

<210> SEQ ID NO 44
<211> LENGTH: 119
<212> TYPE: PRT
<213> ORGANISM: Artificial Sequence
<220> FEATURE:
<223> OTHER INFORMATION: 1A immunoglobulin heavy chain variable region
<220> FEATURE:
<221> NAME/KEY: MISC_FEATURE
```

```
<222> LOCATION: (1)..(119)
<223> OTHER INFORMATION: Possible mutations: R30, S30, N31, S31, Y94,
      H94, D104, E104.

<400> SEQUENCE: 44

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Arg Asn Tyr
            20                  25                  30

Ala Met Tyr Trp Val Arg Gln Ala Pro Gly Lys Gly Leu Glu Trp Val
        35                  40                  45

Ser Ala Ile Gly Ser Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Ala Pro Asn Trp Gly Ser Asp Ala Phe Asp Ile Trp Gly Gln Gly
            100                 105                 110

Thr Met Val Thr Val Ser Ser
            115

<210> SEQ ID NO 45
<211> LENGTH: 107
<212> TYPE: PRT
<213> ORGANISM: Artificial Sequence
<220> FEATURE:
<223> OTHER INFORMATION: 1A immunoglobulin light chain variable region
<220> FEATURE:
<221> NAME/KEY: MISC_FEATURE
<222> LOCATION: (1)..(107)
<223> OTHER INFORMATION: possible mutations: P96, I96, P100, Q100, R103,
      K103, V104, L104, D105, E105

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Pro Gly Thr Lys Val Asp Ile Lys
            100                 105

<210> SEQ ID NO 46
<211> LENGTH: 251
<212> TYPE: PRT
<213> ORGANISM: Artificial Sequence
<220> FEATURE:
<223> OTHER INFORMATION: single chain fv 8A1

<400> SEQUENCE: 46

Glu Val Gln Leu Val Gln Ser Gly Ala Glu Val Lys Lys Pro Gly Glu
1               5                   10                  15
```

```
Ser Leu Thr Ile Ser Cys Lys Gly Pro Gly Tyr Asn Phe Phe Asn Tyr
            20                  25                  30

Trp Ile Gly Trp Val Arg Gln Met Pro Gly Lys Gly Leu Glu Trp Met
        35                  40                  45

Gly Ile Ile Tyr Pro Thr Asp Ser Asp Thr Arg Tyr Ser Pro Ser Phe
    50                  55                  60

Gln Gly Gln Val Thr Ile Ser Val Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Ile Arg Tyr Cys Pro Gly Arg Cys Tyr Ser Gly Tyr
                100                 105                 110

Tyr Gly Met Asp Val Trp Gly Gln Gly Thr Met Val Thr Val Ser Ser
            115                 120                 125

Gly Gly Gly Gly Ser Gly Gly Gly Ser Gly Gly Gly Gly Ser Ser
        130                 135                 140

Glu Leu Thr Gln Asp Pro Ala Val Ser Val Ala Leu Gly Gln Thr Val
145                 150                 155                 160

Arg Ile Thr Cys Gln Gly Asp Ser Leu Arg Ser Tyr Tyr Ala Ser Trp
                165                 170                 175

Tyr Gln Gln Lys Pro Gly Gln Ala Pro Val Leu Val Ile Tyr Gly Lys
            180                 185                 190

Asn Asn Arg Pro Ser Gly Ile Pro Asp Arg Phe Ser Gly Ser Ser Ser
                195                 200                 205

Gly Asn Thr Ala Ser Leu Thr Ile Thr Gly Ala Gln Ala Glu Asp Glu
        210                 215                 220

Ala Asp Tyr Tyr Cys Asn Ser Arg Asp Ser Ser Gly Asn His Val Val
225                 230                 235                 240

Phe Gly Gly Gly Thr Lys Leu Thr Val Leu Gly
                245                 250

<210> SEQ ID NO 47
<211> LENGTH: 245
<212> TYPE: PRT
<213> ORGANISM: Artificial Sequence
<220> FEATURE:
<223> OTHER INFORMATION: single chain fv 9A2

<400> SEQUENCE: 47

Gln Val Gln Leu Val Gln Ser Gly Ala Glu Val Arg Lys Pro Gly Ala
1               5                   10                  15

Ser Val Lys Val Ser Cys Lys Thr Ser Gly Tyr Thr Phe Arg Asn Tyr
            20                  25                  30

Asp Ile Asn Trp Val Arg Gln Ala Pro Gly Gln Gly Leu Glu Trp Met
        35                  40                  45

Gly Arg Ile Ser Gly His Tyr Gly Asn Thr Asp His Ala Gln Lys Phe
    50                  55                  60

Gln Gly Arg Phe Thr Met Thr Lys Asp Thr Ser Thr Ser Thr Ala Tyr
65                  70                  75                  80

Met Glu Leu Arg Ser Leu Thr Phe Asp Thr Ala Val Tyr Tyr Cys
                85                  90                  95

Ala Arg Ser Gln Trp Asn Val Asp Tyr Trp Gly Arg Gly Thr Leu Val
                100                 105                 110

Thr Val Ser Ser Gly Gly Gly Gly Ser Gly Gly Gly Ser Gly Gly
            115                 120                 125
```

```
Gly Gly Ser Ala Leu Asn Phe Met Leu Thr Gln Pro His Ser Val Ser
            130                 135                 140

Glu Ser Pro Gly Lys Thr Val Thr Ile Ser Cys Thr Arg Ser Ser Gly
145                 150                 155                 160

Ser Ile Ala Ser Asn Tyr Val Gln Trp Tyr Gln Gln Arg Pro Gly Ser
                165                 170                 175

Ser Pro Thr Thr Val Ile Phe Glu Asp Asn Arg Arg Pro Ser Gly Val
            180                 185                 190

Pro Asp Arg Phe Ser Gly Ser Ile Asp Thr Ser Ser Asn Ser Ala Ser
        195                 200                 205

Leu Thr Ile Ser Gly Leu Lys Thr Glu Asp Glu Ala Asp Tyr Tyr Cys
    210                 215                 220

Gln Ser Phe Asp Ser Thr Asn Leu Val Val Phe Gly Gly Gly Thr Lys
225                 230                 235                 240

Val Thr Val Leu Gly
                245

<210> SEQ ID NO 48
<211> LENGTH: 245
<212> TYPE: PRT
<213> ORGANISM: Artificial Sequence
<220> FEATURE:
<223> OTHER INFORMATION: single chain fv 11A4

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ser Pro Tyr Ser Ser Arg Trp Tyr Ser Phe Asp Pro Trp Gly
            100                 105                 110

Gln Gly Thr Met Val Thr Val Ser Ser Gly Gly Gly Ser Gly Gly
        115                 120                 125

Gly Gly Ser Gly Gly Gly Gly Ser Ala Leu Ser Tyr Glu Leu Thr Gln
    130                 135                 140

Pro Pro Ser Val Ser Val Ser Pro Gly Gln Thr Ala Thr Ile Thr Cys
145                 150                 155                 160

Ser Gly Asp Asp Leu Gly Asn Lys Tyr Val Ser Trp Tyr Gln Gln Lys
                165                 170                 175

Pro Gly Gln Ser Pro Val Leu Val Ile Tyr Gln Asp Thr Lys Arg Pro
            180                 185                 190

Ser Gly Ile Pro Glu Arg Phe Ser Gly Ser Asn Ser Gly Asn Ile Ala
        195                 200                 205

Thr Leu Thr Ile Ser Gly Thr Gln Ala Val Asp Glu Ala Asp Tyr Tyr
    210                 215                 220

Cys Gln Val Trp Asp Thr Gly Thr Val Val Phe Gly Gly Gly Thr Lys
225                 230                 235                 240
```

```
Leu Thr Val Leu Gly
            245

<210> SEQ ID NO 49
<211> LENGTH: 251
<212> TYPE: PRT
<213> ORGANISM: Artificial Sequence
<220> FEATURE:
<223> OTHER INFORMATION: single chain fv 7A4

<400> SEQUENCE: 49

Glu Val Gln Leu Val Gln Ser Gly Ala Glu Val Lys Lys Pro Gly Glu
1               5                   10                  15

Ser Leu Thr Ile Ser Cys Lys Gly Ser Gly Tyr Asn Phe Phe Asn Tyr
            20                  25                  30

Trp Ile Gly Trp Val Arg Gln Met Pro Gly Lys Asp Leu Glu Trp Met
        35                  40                  45

Gly Ile Ile Tyr Pro Thr Asp Ser Asp Thr Arg Tyr Ser Pro Ser Phe
    50                  55                  60

Gln Gly Gln Val Thr Ile Ser Val Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Ile Arg Tyr Cys Pro Gly Arg Cys Tyr Ser Gly Tyr
            100                 105                 110

Tyr Gly Met Asp Val Trp Gly Gln Gly Thr Met Val Thr Val Ser Ser
            115                 120                 125

Gly Gly Gly Ser Ser Gly Gly Gly Ser Gly Gly Gly Ser Ser
        130                 135                 140

Glu Leu Thr Gln Asp Pro Ala Val Ser Val Ala Leu Gly Gln Thr Val
145                 150                 155                 160

Arg Ile Thr Cys Arg Gly Asp Ser Leu Arg Asn Tyr Tyr Ala Ser Trp
                165                 170                 175

Tyr Gln Gln Lys Pro Gly Gln Ala Pro Val Leu Val Ile Tyr Gly Lys
            180                 185                 190

Asn Asn Arg Pro Ser Gly Ile Pro Asp Arg Phe Ser Gly Ser Ser Ser
        195                 200                 205

Gly Asn Thr Ala Ser Leu Thr Ile Thr Gly Ala Gln Ala Glu Asp Glu
    210                 215                 220

Ala Asp Tyr Tyr Cys Asn Ser Arg Asp Ser Ser Gly Asn His Met Val
225                 230                 235                 240

Phe Gly Gly Gly Thr Lys Leu Thr Val Leu Gly
                245                 250

<210> SEQ ID NO 50
<211> LENGTH: 249
<212> TYPE: PRT
<213> ORGANISM: Artificial Sequence
<220> FEATURE:
<223> OTHER INFORMATION: single chain fv 11A1

<400> SEQUENCE: 50

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Phe
            20                  25                  30

Ala Met His Trp Val Arg Gln Ile Pro Gly Lys Gly Leu Glu Trp Leu
        35                  40                  45
```

Ser Gly Leu Arg His Asp Gly Ser Thr Ala Tyr Tyr Ala Gly Ser Val
             50                  55                  60

Lys Gly Arg Phe Thr Ile Ser Arg Asp Asn Ser Arg Asn Thr Val Tyr
 65                  70                  75                  80

Leu Gln Met Asn Ser Leu Arg Ala Glu Asp Thr Ala Thr Tyr Tyr Cys
                 85                  90                  95

Val Thr Gly Ser Gly Ser Gly Pro His Ala Phe Pro Val Trp Gly
            100                 105                 110

Lys Gly Thr Leu Val Thr Val Ser Ser Gly Gly Gly Ser Gly Gly
            115                 120                 125

Gly Gly Ser Gly Gly Gly Ser Ala Leu Ser Tyr Val Leu Thr Gln
        130                 135                 140

Pro Pro Ser Ala Ser Gly Thr Pro Gly Gln Arg Val Thr Ile Ser Cys
145                 150                 155                 160

Ser Gly Ser Asn Ser Asn Ile Gly Thr Tyr Thr Val Asn Trp Phe Gln
                165                 170                 175

Gln Leu Pro Gly Thr Ala Pro Lys Leu Leu Ile Tyr Ser Asn Asn Gln
            180                 185                 190

Arg Pro Ser Gly Val Pro Asp Arg Phe Ser Gly Ser Lys Ser Gly Thr
        195                 200                 205

Ser Ala Ser Leu Ala Ile Ser Gly Leu Gln Ser Glu Asp Glu Ala Asp
210                 215                 220

Tyr Tyr Cys Ala Ala Trp Asp Asp Ser Leu Asn Gly Pro Val Phe Gly
225                 230                 235                 240

Gly Gly Thr Lys Val Thr Val Leu Gly
                245

<210> SEQ ID NO 51
<211> LENGTH: 251
<212> TYPE: PRT
<213> ORGANISM: Artificial Sequence
<220> FEATURE:
<223> OTHER INFORMATION: single chain fv 7A6

<400> SEQUENCE: 51

Glu Val Gln Leu Val Gln Ser Gly Ala Glu Val Lys Lys Pro Gly Glu
 1               5                  10                  15

Ser Leu Thr Ile Ser Cys Lys Gly Ser Gly Tyr Asn Phe Asn Tyr
                 20                  25                  30

Trp Ile Gly Trp Val Arg Gln Met Pro Gly Lys Gly Leu Glu Trp Met
             35                  40                  45

Gly Ile Ile Tyr Pro Thr Asp Ser Asp Thr Arg Tyr Ser Pro Ser Phe
         50                  55                  60

Gln Gly Gln Val Thr Ile Ser Val Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Ser Ile Arg Tyr Cys Pro Gly Gly Arg Cys Tyr Ser Gly Tyr
            100                 105                 110

Tyr Gly Met Asp Val Trp Gly Gln Gly Thr Leu Val Thr Val Ser Ser
            115                 120                 125

Gly Gly Gly Gly Ser Gly Gly Gly Ser Gly Gly Gly Ser Ser
        130                 135                 140

Glu Leu Thr Gln Asp Pro Ala Val Ser Val Ala Leu Gly Gln Thr Val
145                 150                 155                 160

-continued

```
Arg Ile Thr Cys Gln Gly Asp Ser Leu Arg Ser Tyr Tyr Thr Asn Trp
                165                 170                 175
Phe Gln Gln Lys Pro Gly Gln Ala Pro Leu Leu Val Val Tyr Ala Lys
            180                 185                 190
Asn Lys Arg Pro Ser Gly Ile Pro Asp Arg Phe Ser Gly Ser Ser Ser
        195                 200                 205
Gly Asn Thr Ala Ser Leu Thr Ile Thr Gly Ala Gln Ala Glu Asp Glu
    210                 215                 220
Ala Asp Tyr Tyr Cys Asn Ser Arg Asp Ser Ser Gly Asn His Val Val
225                 230                 235                 240
Phe Gly Gly Gly Thr Lys Leu Thr Val Leu Gly
                245                 250
```

<210> SEQ ID NO 52
<211> LENGTH: 5
<212> TYPE: PRT
<213> ORGANISM: Artificial Sequence
<220> FEATURE:
<223> OTHER INFORMATION: CDR

<400> SEQUENCE: 52

```
Ser Tyr Trp Met His
1               5
```

<210> SEQ ID NO 53
<211> LENGTH: 17
<212> TYPE: PRT
<213> ORGANISM: Artificial Sequence
<220> FEATURE:
<223> OTHER INFORMATION: CDR

<400> SEQUENCE: 53

```
Glu Ile Asn Pro Ser Asn Gly Arg Thr Asn Tyr Asn Glu Lys Phe Lys
1               5                   10                  15
Arg
```

<210> SEQ ID NO 54
<211> LENGTH: 15
<212> TYPE: PRT
<213> ORGANISM: Artificial Sequence
<220> FEATURE:
<223> OTHER INFORMATION: CDR

<400> SEQUENCE: 54

```
Gly Arg Pro Asp Tyr Tyr Gly Ser Ser Lys Trp Tyr Phe Asp Val
1               5                   10                  15
```

<210> SEQ ID NO 55
<211> LENGTH: 16
<212> TYPE: PRT
<213> ORGANISM: Artificial Sequence
<220> FEATURE:
<223> OTHER INFORMATION: CDR

<400> SEQUENCE: 55

```
Arg Ser Ser Gln Ser Ile Val His Ser Asn Val Asn Thr Tyr Leu Glu
1               5                   10                  15
```

<210> SEQ ID NO 56
<211> LENGTH: 7
<212> TYPE: PRT
<213> ORGANISM: Artificial Sequence
<220> FEATURE:

```
<223> OTHER INFORMATION: CDR

<400> SEQUENCE: 56

Lys Val Ser Asn Arg Phe Ser
1               5

<210> SEQ ID NO 57
<211> LENGTH: 9
<212> TYPE: PRT
<213> ORGANISM: Artificial Sequence
<220> FEATURE:
<223> OTHER INFORMATION: CDR

<400> SEQUENCE: 57

Phe Gln Gly Ser His Val Pro Pro Thr
1               5

<210> SEQ ID NO 58
<211> LENGTH: 123
<212> TYPE: PRT
<213> ORGANISM: Artificial Sequence
<220> FEATURE:
<223> OTHER INFORMATION: heavy chain immunoglobulin variable region

<400> SEQUENCE: 58

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Glu Ile Asn Pro Ser Asn Gly Arg Thr Asn Tyr Asn Gln Lys Phe
        50                  55                  60

Gln Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Phe
                85                  90                  95

Ala Arg Gly Arg Pro Asp Tyr Tyr Gly Ser Ser Lys Trp Tyr Phe Asp
            100                 105                 110

Val Trp Gly Gln Gly Thr Thr Val Thr Val Ser
        115                 120

<210> SEQ ID NO 59
<211> LENGTH: 118
<212> TYPE: PRT
<213> ORGANISM: Artificial Sequence
<220> FEATURE:
<223> OTHER INFORMATION: heavy chain immunoglobulin variable region

<400> SEQUENCE: 59

Gln Val Gln Phe Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Leu Met His Trp Ile Lys Gln Arg Pro Gly Arg Gly Leu Glu Trp Ile
            35                  40                  45

Gly Arg Ile Asp Pro Asn Asn Val Val Thr Lys Phe Asn Glu Lys Phe
        50                  55                  60

Lys Ser Lys Ala Thr Leu Thr Val Asp Lys Pro Ser Ser Thr Ala Tyr
65                  70                  75                  80
```

```
Met Glu Leu Ser Ser Leu Thr Ser Glu Asp Ser Ala Val Tyr Tyr Cys
                85                  90                  95

Ala Arg Tyr Ala Tyr Cys Arg Pro Met Asp Tyr Trp Gly Gln Gly Thr
            100                 105                 110

Thr Val Thr Val Ser Ser
        115
```

<210> SEQ ID NO 60
<211> LENGTH: 123
<212> TYPE: PRT
<213> ORGANISM: Artificial Sequence
<220> FEATURE:
<223> OTHER INFORMATION: heavy chain immunoglobulin variable region

<400> SEQUENCE: 60

```
Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Lys Arg Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Phe
                85                  90                  95

Ala Arg Gly Arg Pro Asp Tyr Tyr Gly Ser Ser Lys Trp Tyr Phe Asp
            100                 105                 110

Val Trp Gly Ala Gly Thr Thr Val Thr Val Ser
        115                 120
```

<210> SEQ ID NO 61
<211> LENGTH: 120
<212> TYPE: PRT
<213> ORGANISM: Artificial Sequence
<220> FEATURE:
<223> OTHER INFORMATION: heavy chain immunoglobulin variable region

<400> SEQUENCE: 61

```
Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Phe
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Gly Thr His Tyr Asn Glu Lys Phe
    50                  55                  60

Lys Gly Lys Ala Thr Phe Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Gly His Ser Tyr Tyr Phe Tyr Asp Gly Asp Tyr Trp Gly Gln
            100                 105                 110

Gly Thr Ser Val Thr Val Ser Ser
        115                 120
```

<210> SEQ ID NO 62

```
<211> LENGTH: 120
<212> TYPE: PRT
<213> ORGANISM: Artificial Sequence
<220> FEATURE:
<223> OTHER INFORMATION: heavy chain immunoglobulin variable region

<400> SEQUENCE: 62

Gln Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Ser Ser
            20                  25                  30

Trp Ile His Trp Ala Lys Gln Arg Pro Gly Gln Gly Leu Glu Trp Ile
        35                  40                  45

Gly Glu Ile His Pro Asn Ser Gly Asn Thr Asn Tyr Asn Glu Lys Phe
    50                  55                  60

Lys Gly Lys Ala Thr Leu Thr Val Asp Thr Ser Ser Thr Ala Tyr
65                  70                  75                  80

Val Asp Leu Ser Ser Leu Thr Ser Glu Asp Ser Ala Val Tyr Tyr Cys
                85                  90                  95

Ala Arg Trp Arg Tyr Gly Ser Pro Tyr Tyr Phe Asp Tyr Trp Gly Gln
            100                 105                 110

Gly Thr Thr Leu Thr Val Ser Ser
        115                 120

<210> SEQ ID NO 63
<211> LENGTH: 120
<212> TYPE: PRT
<213> ORGANISM: Artificial Sequence
<220> FEATURE:
<223> OTHER INFORMATION: heavy chain immunoglobulin variable region

<400> SEQUENCE: 63

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Arg Gly Leu Glu Trp Ile
        35                  40                  45

Gly Arg Ile Asp Pro Asn Ser Gly Gly Thr Lys Tyr Asn Glu Lys Phe
    50                  55                  60

Lys Ser Lys Ala Thr Leu Thr Val Asp Lys Pro Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Asp Tyr Tyr Gly Ser Ser Tyr Phe Asp Tyr Trp Gly Gln
            100                 105                 110

Gly Thr Thr Leu Thr Val Ser Ser
        115                 120

<210> SEQ ID NO 64
<211> LENGTH: 123
<212> TYPE: PRT
<213> ORGANISM: Artificial Sequence
<220> FEATURE:
<223> OTHER INFORMATION: heavy chain immunoglobulin variable region

<400> SEQUENCE: 64

Gln Val Gln Leu Val Gln Ser Gly Ala Glu Val Val Lys Pro Gly Ala
1               5                   10                  15
```

```
Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
            35                  40                  45

Gly Glu Ile Asn Pro Ser Asn Gly Arg Thr Asn Tyr Asn Gln Lys Phe
 50                  55                  60

Gln Gly Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Phe
                85                  90                  95

Ala Arg Gly Arg Pro Asp Tyr Tyr Gly Ser Ser Lys Trp Tyr Phe Asp
            100                 105                 110

Val Trp Gly Gln Gly Thr Thr Val Thr Val Ser
            115                 120

<210> SEQ ID NO 65
<211> LENGTH: 124
<212> TYPE: PRT
<213> ORGANISM: Artificial Sequence
<220> FEATURE:
<223> OTHER INFORMATION: heavy chain immunoglobulin variable region

<400> SEQUENCE: 65

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
            35                  40                  45

Gly Glu Ile Asn Pro Ser Asn Gly Arg Thr Asn Tyr Asn Glu Lys Phe
 50                  55                  60

Lys Arg Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Phe
                85                  90                  95

Ala Arg Gly Arg Pro Asp Tyr Tyr Gly Ser Ser Lys Trp Tyr Phe Asp
            100                 105                 110

Val Trp Gly Ala Gly Thr Thr Val Thr Val Ser Ser
            115                 120

<210> SEQ ID NO 66
<211> LENGTH: 124
<212> TYPE: PRT
<213> ORGANISM: Artificial Sequence
<220> FEATURE:
<223> OTHER INFORMATION: heavy chain immunoglobulin variable region

<400> SEQUENCE: 66

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
            35                  40                  45

Gly Glu Ile Asn Pro Ser Asn Gly Arg Thr Asn Tyr Asn Gln Lys Phe
 50                  55                  60

Gln Gly Lys Ala Thr Leu Thr Val Asp Lys Ser Ser Ser Thr Ala Tyr
 65                  70                  75                  80
```

Met Gln Leu Ser Ser Leu Thr Ser Glu Asp Ser Ala Val Tyr Tyr Phe
            85                  90                  95

Ala Arg Gly Arg Pro Asp Tyr Tyr Gly Ser Ser Lys Trp Tyr Phe Asp
            100                 105                 110

Val Trp Gly Gln Gly Thr Thr Val Thr Val Ser Ser
            115                 120

<210> SEQ ID NO 67
<211> LENGTH: 120
<212> TYPE: PRT
<213> ORGANISM: Artificial Sequence
<220> FEATURE:
<223> OTHER INFORMATION: heavy chain immunoglobulin variable region

<400> SEQUENCE: 67

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Arg Gly Leu Glu Trp Ile
            35                  40                  45

Gly Arg Ile Asp Pro Asn Ser Gly Gly Thr Lys Tyr Asn Glu Lys Phe
        50                  55                  60

Lys Ser Lys Ala Thr Leu Thr Val Asp Lys Pro Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Tyr Asp Tyr Tyr Gly Ser Ser Tyr Phe Asp Tyr Trp Gly Gln
            100                 105                 110

Gly Thr Thr Val Thr Val Ser Ser
        115                 120

<210> SEQ ID NO 68
<211> LENGTH: 117
<212> TYPE: PRT
<213> ORGANISM: Artificial Sequence
<220> FEATURE:
<223> OTHER INFORMATION: heavy chain immunoglobulin variable region

<400> SEQUENCE: 68

Gln Ile Gln Leu Gln Gln Ser Gly Pro Glu Leu Val Arg Pro Gly Ala
1               5                   10                  15

Ser Val Lys Ile Ser Cys Lys Ala Ser Gly Tyr Thr Phe Thr Asp Tyr
            20                  25                  30

Tyr Ile His Trp Val Lys Gln Arg Pro Gly Glu Gly Leu Glu Trp Ile
            35                  40                  45

Gly Trp Ile Tyr Pro Gly Ser Gly Asn Thr Lys Tyr Asn Glu Lys Phe
        50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Phe Cys
            85                  90                  95

Ala Arg Gly Gly Lys Phe Ala Met Asp Tyr Trp Gly Gln Gly Thr Ser
            100                 105                 110

Val Thr Val Ser Ser
        115

```
<210> SEQ ID NO 69
<211> LENGTH: 124
<212> TYPE: PRT
<213> ORGANISM: Artificial Sequence
<220> FEATURE:
<223> OTHER INFORMATION: heavy chain immunoglobulin variable region

<400> SEQUENCE: 69

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Glu Ile Asn Pro Ser Asn Gly Arg Thr Asn Tyr Asn Glu Lys Phe
        50                  55                  60

Lys Arg Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Phe
                85                  90                  95

Ala Arg Gly Arg Pro Asp Tyr Tyr Gly Ser Ser Lys Tyr Phe Asp
            100                 105                 110

Val Trp Gly Ala Gly Thr Thr Val Thr Val Ser Ser
        115                 120

<210> SEQ ID NO 70
<211> LENGTH: 120
<212> TYPE: PRT
<213> ORGANISM: Artificial Sequence
<220> FEATURE:
<223> OTHER INFORMATION: heavy chain immunoglobulin variable region

<400> SEQUENCE: 70

Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Tyr Ile Asn Trp Met Lys Gln Lys Pro Gly Gln Gly Leu Glu Trp Ile
            35                  40                  45

Gly Trp Ile Asp Pro Gly Ser Gly Asn Thr Lys Tyr Asn Glu Lys Phe
        50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Thr Ala Val Tyr Phe Cys
                85                  90                  95

Ala Arg Glu Lys Thr Thr Tyr Tyr Ala Met Asp Tyr Trp Gly Gln
            100                 105                 110

Gly Thr Ser Val Thr Val Ser Ala
        115                 120

<210> SEQ ID NO 71
<211> LENGTH: 115
<212> TYPE: PRT
<213> ORGANISM: Artificial Sequence
<220> FEATURE:
<223> OTHER INFORMATION: heavy chain immunoglobulin variable region

<400> SEQUENCE: 71

Val Gln Leu Gln Gln Ser Gly Ala Glu Leu Met Lys Pro Gly Ala Ser
1               5                   10                  15
```

Val Lys Ile Ser Cys Lys Ala Ser Gly Tyr Thr Phe Ser Asp Tyr Trp
            20                  25                  30

Ile Glu Trp Val Lys Gln Arg Pro Gly His Gly Leu Glu Trp Ile Gly
            35                  40                  45

Glu Ile Leu Pro Gly Ser Gly Ser Thr Asn Tyr His Glu Arg Phe Lys
            50                  55                  60

Gly Lys Ala Thr Phe Thr Ala Asp Thr Ser Ser Ser Thr Ala Tyr Met
65                  70                  75                  80

Gln Leu Asn Ser Leu Thr Ser Glu Asp Ser Gly Val Tyr Tyr Cys Leu
                85                  90                  95

His Gly Asn Tyr Asp Phe Asp Gly Trp Gly Gln Gly Thr Thr Leu Thr
            100                 105                 110

Val Ser Ser
        115

<210> SEQ ID NO 72
<211> LENGTH: 120
<212> TYPE: PRT
<213> ORGANISM: Artificial Sequence
<220> FEATURE:
<223> OTHER INFORMATION: heavy chain immunoglobulin variable region

<400> SEQUENCE: 72

Gln Val Gln Leu Leu Glu Ser Gly Ala Glu Leu Met Lys Pro Gly Ala
1               5                   10                  15

Ser Val Lys Ile Ser Cys Lys Ala Thr Gly Tyr Thr Phe Ser Ser Phe
            20                  25                  30

Trp Ile Glu Trp Val Lys Gln Arg Pro Gly His Gly Leu Glu Trp Ile
            35                  40                  45

Gly Glu Ile Leu Pro Gly Ser Gly Gly Thr His Tyr Asn Glu Lys Phe
            50                  55                  60

Lys Gly Lys Ala Thr Phe Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Gly His Ser Tyr Tyr Phe Tyr Asp Gly Asp Tyr Trp Gly Gln
            100                 105                 110

Gly Thr Ser Val Thr Val Ser Ser
        115                 120

<210> SEQ ID NO 73
<211> LENGTH: 113
<212> TYPE: PRT
<213> ORGANISM: Artificial Sequence
<220> FEATURE:
<223> OTHER INFORMATION: light  chain immunoglobulin variable region

<400> SEQUENCE: 73

Asp Val Leu Met Thr Gln Ile Pro Val Ser Leu Pro Val Ser Leu Gly
1               5                   10                  15

Asp Gln Ala Ser Ile Ser Cys Arg Ser Ser Gln Ile Ile Val His Asn
            20                  25                  30

Asn Gly Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
            50                  55                  60

Asp Arg Phe Ser Gly Ser Gly Ser Gly Thr Asp Phe Thr Leu Lys Ile

```
                65                  70                  75                  80
Ser Arg Val Glu Ala Glu Asp Leu Gly Val Tyr Tyr Cys Phe Gln Gly
                    85                  90                  95

Ser His Val Pro Phe Thr Phe Gly Ser Gly Thr Lys Leu Glu Ile Lys
            100                 105                 110

Arg

<210> SEQ ID NO 74
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 74

Asp Val Leu Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 75
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 75

Asp Val Leu Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 76
<211> LENGTH: 113
```

<212> TYPE: PRT
<213> ORGANISM: Artificial Sequence
<220> FEATURE:
<223> OTHER INFORMATION: light chain immunoglobulin variable region

<400> SEQUENCE: 76

```
Asp Val Leu Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg
```

<210> SEQ ID NO 77
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 77

```
Asp Val Leu Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg
```

<210> SEQ ID NO 78
<211> LENGTH: 113
<212> TYPE: PRT
<213> ORGANISM: Artificial Sequence
<220> FEATURE:
<223> OTHER INFORMATION: light chain immunoglobulin variable region
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid

```
<400> SEQUENCE: 78

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Xaa Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Xaa Thr Phe Gly Gly Gly Thr Lys Leu Glu Ile Lys
            100                 105                 110

Arg

<210> SEQ ID NO 79
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 79

Asp Val Val Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 80
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 80

Asp Val Val Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60
```

```
Asp Arg Phe Ser Gly Ser Gly Ala Gly Thr Asp Phe Thr Leu Arg Ile
 65                  70                  75                  80

Ser Arg Val Glu Ala Glu Asp Leu Gly Ile Tyr Tyr Cys Phe Gln Gly
                 85                  90                  95

Ser His Val Pro Pro Thr Phe Gly Gly Gly Thr Lys Leu Glu Ile Lys
            100                 105                 110

Arg

<210> SEQ ID NO 81
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 81

Asp Val Leu Met Thr Gln Thr Pro Leu Ser Leu Pro Val Ser Leu Gly
  1               5                  10                  15

Asp Pro Ala Ser Ile Ser Cys Arg Ser Ser Gln Ser Ile Val His Ser
                 20                  25                  30

Asn Val Asn Thr Tyr Leu Glu Trp Tyr Leu Gln Lys Pro Gly Gln Ser
             35                  40                  45

Pro Arg Leu Leu Ile Tyr Lys Val Ser Asn Arg Phe Ser Gly Val Pro
     50                  55                  60

Asp Arg Phe Ser Gly Ser Gly Ala Gly Thr Asp Phe Thr Leu Arg Ile
 65                  70                  75                  80

Ser Arg Val Glu Ala Glu Asp Leu Gly Ile Tyr Tyr Cys Phe Gln Gly
                 85                  90                  95

Ser His Val Pro Pro Thr Phe Gly Gly Gly Thr Lys Leu Glu Ile Lys
            100                 105                 110

Arg

<210> SEQ ID NO 82
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 82

Asp Val Leu Met Thr Gln Ile Pro Val Ser Leu Pro Val Ser Leu Gly
  1               5                  10                  15

Asp Gln Ala Ser Ile Ser Cys Arg Ser Ser Gln Ile Ile Val His Asn
                 20                  25                  30

Asn Gly Asn Thr Tyr Leu Glu Trp Tyr Leu Gln Lys Pro Gly Gln Ser
             35                  40                  45

Pro Gln Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Phe Thr Phe Gly Ser Gly Thr Lys Leu Glu Ile Lys
            100                 105                 110

Arg
```

```
<210> SEQ ID NO 83
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 83

Asp Val Leu Met Thr Gln Thr Pro Leu Ser Leu Pro Val Ser Leu Gly
1               5                   10                  15

Asp Gln Ala Ser Ile Ser Cys Arg Phe Ser Gln Ser Ile Val His Ser
            20                  25                  30

Asn Gly Asn Thr Tyr Leu Glu Trp Tyr Leu Gln Lys Ser Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Arg Thr Phe Gly Gly Gly Thr Lys Leu Glu Ile Lys
            100                 105                 110

Arg

<210> SEQ ID NO 84
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 84

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg

<210> SEQ ID NO 85
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 85

Asp Val Val Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
```

```
                    20                  25                  30
Asn Val Asn Thr Tyr Leu Glu Trp Tyr Leu Gln Lys Pro Gly Gln Ser
                35                  40                  45
Pro Lys Leu Leu Ile Tyr Lys Val Ser Asn Arg Phe Ser Gly Val Pro
         50                  55                  60
Asp Arg Phe Ser Gly Ser Gly Ala Gly Thr Asp Phe Thr Leu Arg Ile
 65                  70                  75                  80
Ser Arg Val Glu Ala Glu Asp Leu Gly Ile Tyr Tyr Cys Phe Gln Gly
                 85                  90                  95
Ser His Val Pro Pro Thr Phe Gly Gly Gly Thr Lys Leu Glu Ile Lys
                100                 105                 110
Arg

<210> SEQ ID NO 86
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 86

Glu Leu Val Met Thr Gln Thr Pro Leu Ser Leu Pro Val Ser Leu Gly
 1               5                  10                  15
Asp Gln Ala Ser Ile Ser Cys Arg Ser Ser Gln Thr Ile Val His Ser
                20                  25                  30
Asn Gly Asp Thr Tyr Leu Asp Trp Phe Leu Gln Lys Pro Gly Gln Ser
                35                  40                  45
Pro Lys Leu Leu Ile Tyr Lys Val Ser Asn Arg Phe Ser Gly Val Pro
         50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Leu Gly Val Tyr Tyr Cys Phe Gln Gly
                 85                  90                  95
Ser His Val Pro Pro Thr Phe Gly Gly Gly Thr Lys Leu Glu Ile Lys
                100                 105                 110
Arg

<210> SEQ ID NO 87
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 87

Asp Val Leu Met Thr Gln Thr Pro Leu Ser Leu Pro Val Ser Leu Gly
 1               5                  10                  15
Asp Pro Ala Ser Ile Ser Cys Arg Ser Ser Gln Ser Ile Val His Ser
                20                  25                  30
Asn Val Asn Thr Tyr Leu Glu Trp Tyr Leu Gln Lys Pro Gly Gln Ser
                35                  40                  45
Pro Lys Leu Leu Ile Tyr Lys Val Ser Asn Arg Phe Ser Gly Val Pro
         50                  55                  60
Asp Arg Phe Ser Gly Ser Gly Ala Gly Thr Asp Phe Thr Leu Arg Ile
 65                  70                  75                  80
Ser Arg Val Glu Ala Glu Asp Leu Gly Ile Tyr Tyr Cys Phe Gln Gly
                 85                  90                  95
```

-continued

Ser His Val Pro Pro Thr Phe Gly Gly Gly Thr Lys Leu Glu Ile Lys
                100                 105                 110

Arg

<210> SEQ ID NO 88
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 88

Asp Val Val Met Thr Gln Thr Pro Leu Ser Leu Pro Val Ser Leu Gly
1               5                   10                  15

Asp Pro Ala Ser Ile Ser Cys Arg Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
                100                 105                 110

Arg

<210> SEQ ID NO 89
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 89

Asp Val Leu Met Thr Gln Thr Pro Val Ser Leu Ser Val Ser Leu Gly
1               5                   10                  15

Asp Gln Ala Ser Ile Ser Cys Arg Ser Ser Gln Ser Ile Val His Ser
            20                  25                  30

Thr Gly Asn Thr Tyr Leu Glu Trp Tyr Leu Gln Lys Pro Gly Gln Ser
        35                  40                  45

Pro Lys Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ala
                85                  90                  95

Ser His Ala Pro Arg Thr Phe Gly Gly Gly Thr Lys Leu Glu Ile Lys
                100                 105                 110

Arg

<210> SEQ ID NO 90
<211> LENGTH: 113
<212> TYPE: PRT
<213> ORGANISM: Artificial Sequence
<220> FEATURE:
<223> OTHER INFORMATION: light chain immunoglobulin variable region

```
<400> SEQUENCE: 90

Asp Val Leu Met Thr Gln Thr Pro Leu Ser Leu Pro Val Ser Leu Gly
1               5                   10                  15

Asp Gln Ala Ser Ile Ser Cys Lys Ser Ser Gln Ser Ile Val His Ser
            20                  25                  30

Ser Gly Asn Thr Tyr Phe Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Ile Pro Phe Thr Phe Gly Ser Gly Thr Lys Leu Glu Ile Lys
                100                 105                 110

Arg

<210> SEQ ID NO 91
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 91

Asp Ile Glu Leu Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
                100                 105                 110

Arg

<210> SEQ ID NO 92
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 92

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
```

```
                50                  55                  60
Asp Arg Phe Ser Gly Ser Gly Ser Gly Thr Asp Phe Thr Leu Arg Ile
 65                  70                  75                  80

Ser Arg Val Glu Ala Glu Asp Leu Gly Ile Tyr Tyr Cys Phe Gln Gly
                 85                  90                  95

Ser His Val Pro Pro Thr Phe Gly Gly Gly Thr Lys Leu Glu Ile Lys
                100                 105                 110

Arg

<210> SEQ ID NO 93
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 93

Asp Val Val Met Thr Gln Thr Pro Leu Ser Leu Pro Val Ser Leu Gly
  1               5                  10                  15

Asp Pro Ala Ser Ile Ser Cys Arg Ser Ser Gln Ser Ile Val His Ser
                 20                  25                  30

Asn Val Asn Thr Tyr Leu Glu Trp Tyr Leu Gln Lys Pro Gly Gln Ser
             35                  40                  45

Pro Arg Leu Leu Ile Tyr Lys Val Ser Asn Arg Phe Ser Gly Val Pro
 50                  55                  60

Asp Arg Phe Ser Gly Ser Gly Ala Gly Thr Asp Phe Thr Leu Arg Ile
 65                  70                  75                  80

Ser Arg Val Glu Ala Glu Asp Leu Gly Ile Tyr Tyr Cys Phe Gln Gly
                 85                  90                  95

Ser His Val Pro Pro Thr Phe Gly Gly Gly Thr Lys Leu Glu Ile Lys
                100                 105                 110

Arg

<210> SEQ ID NO 94
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 94

Asp Val Leu Met Thr Gln Thr Pro Leu Ser Leu Pro Val Ser Leu Gly
  1               5                  10                  15

Asp Gln Ala Ser Ile Ser Cys Arg Ser Ser Gln Ser Ile Val His Ser
                 20                  25                  30

Asn Val Asn Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Arg Ile
 65                  70                  75                  80

Ser Arg Val Glu Ala Glu Asp Leu Gly Ile Tyr Tyr Cys Phe Gln Gly
                 85                  90                  95

Ser His Val Pro Pro Thr Phe Gly Gly Gly Thr Lys Leu Glu Ile Lys
                100                 105                 110

Arg
```

<210> SEQ ID NO 95
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 95

```
Asp Val Val Met Thr Gln Thr Pro Leu Ser Leu Pro Val Ser Leu Gly
1               5                   10                  15

Asp Pro Ala Ser Ile Ser Cys Arg Ser Ser Gln Ser Ile Val His Ser
            20                  25                  30

Asn Val Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

Arg
```

<210> SEQ ID NO 96
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 96

```
Asp Val Leu Met Thr Gln Thr Pro Leu Ser Leu Pro Val Ser Leu Gly
1               5                   10                  15

Asp Gln Ala Ser Ile Ser Cys Arg Ser Asn Gln Thr Ile Leu Leu Ser
            20                  25                  30

Asp Gly Asp Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

Arg
```

<210> SEQ ID NO 97
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 97

```
Asp Val Leu Met Thr Gln Thr Pro Leu Ser Leu Pro Val Ser Leu Gly
1               5                   10                  15
```

Asp Gln Ala Ser Ile Ser Cys Arg Ser Ser Gln Thr Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Thr Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Thr His Ala Pro Tyr Thr Phe Gly Gly Gly Thr Lys Leu Glu Ile Lys
                100                 105                 110

Arg

<210> SEQ ID NO 98
<211> LENGTH: 113
<212> TYPE: PRT
<213> ORGANISM: Artificial Sequence
<220> FEATURE:
<223> OTHER INFORMATION: light chain immunoglobulin variable region

<400> SEQUENCE: 98

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Ser Ile Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Gln Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
                100                 105                 110

Arg

<210> SEQ ID NO 99
<211> LENGTH: 14
<212> TYPE: DNA
<213> ORGANISM: Artificial Sequence
<220> FEATURE:
<223> OTHER INFORMATION: primer

<400> SEQUENCE: 99
ctccgcttcc tttc                                                           14

<210> SEQ ID NO 100
<211> LENGTH: 18
<212> TYPE: DNA
<213> ORGANISM: Artificial Sequence
<220> FEATURE:
<223> OTHER INFORMATION: anti-sense

<400> SEQUENCE: 100
atctctccgc ttcctttc                                                       18

<210> SEQ ID NO 101

```
<211> LENGTH: 18
<212> TYPE: DNA
<213> ORGANISM: Artificial Sequence
<220> FEATURE:
<223> OTHER INFORMATION: anti-sense

<400> SEQUENCE: 101
atctctccgc ttcctttc                                                 18

<210> SEQ ID NO 102
<211> LENGTH: 19
<212> TYPE: DNA
<213> ORGANISM: Artificial Sequence
<220> FEATURE:
<223> OTHER INFORMATION: primer

<400> SEQUENCE: 102
aggagctcga ggcgttcag                                                19

<210> SEQ ID NO 103
<211> LENGTH: 22
<212> TYPE: DNA
<213> ORGANISM: Artificial Sequence
<220> FEATURE:
<223> OTHER INFORMATION: primer

<400> SEQUENCE: 103
gtcttgggtg ggtagagcaa tc                                            22

<210> SEQ ID NO 104
<211> LENGTH: 21
<212> TYPE: DNA
<213> ORGANISM: Artificial Sequence
<220> FEATURE:
<223> OTHER INFORMATION: primer

<400> SEQUENCE: 104
aggccaaacg tcaccgtccc c                                             21

<210> SEQ ID NO 105
<211> LENGTH: 109
<212> TYPE: PRT
<213> ORGANISM: Artificial Sequence
<220> FEATURE:
<223> OTHER INFORMATION: A12 immunoglobulin light chain variable region

<400> SEQUENCE: 105

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Thr Trp Tyr Gln Gln Lys Pro Gly Gln Ala Pro Ile Leu Val Ile Tyr
        35                  40                  45

Gly Glu Asn Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Gly Ser Gly Gln His
                85                  90                  95

Leu Val Phe Gly Gly Gly Thr Lys Leu Thr Val Leu Gly
            100                 105
```